United States Patent
Florence et al.

(10) Patent No.: US 10,494,425 B2
(45) Date of Patent: Dec. 3, 2019

(54) ANTI-AMYLOID-BETA ANTIBODIES

(71) Applicant: RPEPTIDE, LLC, Bogart, GA (US)

(72) Inventors: Quentin Florence, Loganville, GA (US); Nanda Menon, Athens, GA (US); William Moffitt, Alexandria, VA (US); Bill Lunsford, III, Athens, GA (US)

(73) Assignee: rPeptide, LLC, Bogart, GA (US)

( * ) Notice: Subject to any disclaimer, the term of this patent is extended or adjusted under 35 U.S.C. 154(b) by 0 days.

(21) Appl. No.: 15/552,614

(22) PCT Filed: Feb. 23, 2016

(86) PCT No.: PCT/US2016/019064
§ 371 (c)(1),
(2) Date: Aug. 22, 2017

(87) PCT Pub. No.: WO2016/137947
PCT Pub. Date: Sep. 1, 2016

(65) Prior Publication Data
US 2018/0051072 A1 Feb. 22, 2018

Related U.S. Application Data

(60) Provisional application No. 62/198,790, filed on Jul. 30, 2015, provisional application No. 62/120,138, filed on Feb. 24, 2015.

(51) Int. Cl.
| | |
|---|---|
| *C07K 16/18* | (2006.01) |
| *G01N 33/68* | (2006.01) |
| *A61K 39/395* | (2006.01) |
| *A61P 25/28* | (2006.01) |
| *A61K 39/00* | (2006.01) |

(52) U.S. Cl.
CPC ......... *C07K 16/18* (2013.01); *G01N 33/6896* (2013.01); *A61K 39/3955* (2013.01); *A61K 2039/505* (2013.01); *A61P 25/28* (2018.01); *C07K 2317/24* (2013.01); *C07K 2317/34* (2013.01); *C07K 2317/565* (2013.01); *C07K 2317/92* (2013.01); *G01N 2800/2821* (2013.01); *G01N 2800/52* (2013.01)

(58) Field of Classification Search
CPC .......... C07K 16/18; C07K 2317/24; C07K 2317/34; C07K 2317/56; C07K 2317/565; C07K 2317/92; G01N 33/6896; G01N 2800/2821; G01N 2800/52; A61K 39/3955
See application file for complete search history.

(56) References Cited

U.S. PATENT DOCUMENTS

| | | | | |
|---|---|---|---|---|
| 8,859,501 B2 * | 10/2014 | Nordstrom | ............. | C07K 16/18 514/17.7 |
| 2010/0068137 A1 | 3/2010 | Chang et al. | | |
| 2011/0200595 A1 | 8/2011 | Gerdes et al. | | |
| 2012/0177664 A1 * | 7/2012 | Yokoseki | ............... | C07K 16/18 424/172.1 |
| 2013/0164278 A1 | 6/2013 | Pfeifer et al. | | |
| 2015/0037328 A1 | 2/2015 | Liu et al. | | |

FOREIGN PATENT DOCUMENTS

WO 2009100953 A2 8/2009

OTHER PUBLICATIONS

Alberts et al. Molecular Biology of the Cell, 3rd Edition, 1994, pp. 1216-1220. (Year: 1994).*
Kuby J, editor, Immunology, Third Edition, 1997, pp. 131-134. (Year: 1997).*
Padlan et al. Proc Natl Acad Sci USA, 1989; 86:5938-5942. (Year: 1989).*
Paul We, editor, Fundamental Immunology, Third Edition, 1993, pp. 292-295. (Year: 1993).*
Rudikoff et al. Proc Natl Acad Sci USA, 1982; 79(6):1979-1983. (Year: 1982).*
Christensen et al. Brain Res. 2009, 1301, 116-125. (Year: 2009).*
UniProtKB-A4GKU8 (Apr. 17, 2007) www.uniprot.org/uniprot/A4GKU8.
UniProtKB-W3REZ6 (Mar. 19, 2014) www.uniprot.org/uniprot/W3REZ6.
Yankner et al., "Beta Amyloid 7E7 (BA1101)," Science Physiol. Rev J. Biol. Chem Neurobiology of Aging (Jan. 1, 2015); www.rpeptide.com/_code/_dyn_images/products/data-sheet/BA-1101-Beta-Amyloid-7E7-Antibody_2.pdf.
Stine et al., "In vitro characterization of conditions for amyloid-beta peptide oligomerization and fibrillogenesis" Journal of Biochemistry (Mar. 28, 2003); 278(13):11612-11622.

* cited by examiner

*Primary Examiner* — Kimberly Ballard
(74) *Attorney, Agent, or Firm* — Fox Rothschild LLP

(57) ABSTRACT

The present invention relates, in part, to isolated antibodies that specifically interact with and show measurable binding affinity to an epitope of the amyloid-beta (Aβ) protein. Such antibodies may be used for the modulation of Aβ activity and/or aggregation or amyloidosis, to study the effects of the Aβ protein on cell function and, in certain embodiments, for the treatment and/or prevention of a disease or condition associated with Aβ activity, aggregation, and/or amyloidosis.

32 Claims, 16 Drawing Sheets
Specification includes a Sequence Listing.

ANTI-AMYLOID-BETA ANTIBODIES

CROSS-REFERENCE TO RELATED APPLICATIONS

This application claims priority to U.S. provisional application Ser. No. 62/198,790, filed Jul. 30, 2015 and U.S. provisional application Ser. No. 62/120,138, filed Feb. 24, 2015, the disclosures of which are incorporated herein by reference in their entirety.

FIELD OF THE INVENTION

The present invention relates, in part, to isolated antibodies and fragments thereof that specifically interact with and show measurable binding affinity to an epitope of the amyloid-beta protein. Such antibodies may be used for the modulation of amyloid-beta activity or aggregation, to study its effects on cell function and, in certain embodiments, for the treatment, prevention, diagnosis and/or monitoring of a disease or condition associated with such proteins.

BACKGROUND OF THE INVENTION

Alzheimer's disease (AD) is a progressive neurodegenerative disorder characterized by the formation of plaques and neurofibrillary tangles in the brain. While the mechanisms of the cause and progression of the disease are poorly understood, over time it results in loss of cognitive abilities and neuronal loss in several regions of the brain. The plaques are believed to be formed from deposits of amyloid beta (Aβ) peptide and are widely believed to be linked to such disease symptoms, though the causative contribution of such plaques to the disease is not well-understood.

Aβ peptides are formed from the amyloid precursor protein (APP) by proteolytic processing. This processing is effected by the cooperative activity of several proteases, namely α-, β- and γ-secretase, which results in a number of fragments of differing length. The fragments found in the plaques include mostly those having a length of 40 or 42 amino acids (Aβ40, Aβ42—defined below). These proteins tend to polymerize in an aqueous environment. Thus, they may be present in a variety of different molecular forms (e.g. monomers, dimers, oligomers, etc.). A simple correlation of the deposition of insoluble protein with the occurrence or progression of dementia disorders such as, for example, Alzheimer's disease, has proved to be unconvincing (Terry et al., Ann. Neurol. 30: 572-580, 1991; Dickson et al., Neurobiol. Aging 16: 285-298, 1995). In contrast, the loss of synapses and cognitive perception seems to correlate better with soluble forms of Aβ(1-42) (Lue et al., Am. J. Pathol. 155: 853-862, 1999; McLean et al., Ann. Neurol. 46: 860-866, 1999).

There exists a tremendous, unmet therapeutic need for the development of biologics useful in the study, diagnosis, prognosis, and/or treatment in Alzheimer's disease. In particular, there is a need for the development of biologics that bind the soluble form of the Aβ fragments, particularly Aβ40 and Aβ42. Such a need is particularly evident in view of the lack of understanding of this disease after decades of research. Such Aβ binding proteins will allow for the elucidation of the biological properties of the proteins and other biological factors responsible for this debilitating disease. The need is also evident from increasing longevity of the general population and, with this increase, an associated rise in the number of patients annually diagnosed with Alzheimer's disease or related disorders. Aβ binding proteins will allow for proper diagnosis and/or prognosis of Alzheimer's disease in a patient experiencing symptoms thereof, a diagnosis which can only be confirmed upon autopsy at the present time. Ideally, such biologics may also be used in the prevention and/or treatment of such a disease.

SUMMARY OF THE INVENTION

In certain aspects, the present invention relates to isolated antibodies or fragments thereof that specifically interact with and/or show measurable binding affinity to an epitope of the amyloid-beta (herein "Aβ") protein, including its isoforms having amino acids 1-40 and/or 1-42. In certain preferred embodiments, the isolated antibodies or fragments thereof specifically interact with and/or show measurable binding affinity to an epitope of a soluble form of the Aβ40 and/or Aβ42 peptides.

In certain embodiments, the epitope is a linear epitope having the sequence VHHQKLVFFAEDV (SEQ ID NO: 3), which reside at residues 12-24 of the Aβ 1-40 and 1-42 isoforms. In further embodiments, the anti-Aβ antibodies bind to such an epitope under conditions where at least the asparagine residue at position 27 of the Aβ(1-40) or Aβ(1-42) has not undergone deamidation. In even further embodiments, the anti-Aβ antibodies bind to such an epitope when the amyloid beta protein is in a monomeric form.

In certain embodiments, the epitope is a linear or conformational epitope having (or within) the sequence AEFRHDSGYEVHHQKLVFFAE (SEQ ID NO: 4), which reside at residues 2-22 of the Aβ (1-40) and Aβ (1-42) isoforms. In further embodiments, the anti-Aβ antibodies bind to such an epitope under conditions where at least the asparagine residue at position 27 of the Aβ(1-40) or Aβ(1-42) has not undergone deamidation. In even further embodiments, the anti-Aβ antibodies bind to such an epitope when the amyloid beta protein is in an oligomeric form. In even further embodiments, the anti-Aβ antibodies bind to such an epitope when the amyloid beta protein is in an aggregated tetrameric form.

Antibodies of the present invention (collectively referred to as anti-amyloid-beta antibodies or anti-Aβ antibodies) may include the entire antibody, a fragment or substantially homologous fragment of the monoclonal antibody 7E7, any such fragment or substantially homologous fragment including but not limited to one, two, three, four, five or all six CDRs (as determined by either the Kabat and/or Chothia methodology, as described herein, as for example each of three CDRs from the variable light chain and/or each of three CDRs from the variable heavy chain) from the variable light chain and/or the variable heavy chain of the monoclonal antibody 7E7. Antibodies of the present invention may include the entire antibody, a fragment or substantially homologous fragment of the monoclonal antibody 6C2, any such fragment or substantially homologous fragment including but not limited to one, two, three, four, five or all six CDRs (as determined by either the Kabat and/or Chothia methodology, as described herein, as for example each of three CDRs from the variable light chain and/or each of three CDRs from the variable heavy chain) from the variable light chain and/or the variable heavy chain of the monoclonal antibody 6C2. Any such entire antibody, antibody fragment, or substantially homologous fragment (such as, but not limited to, a substantially homologous fragment containing one or more conservative amino acid substitutions) may be derived from the 7E7 antibody. Additionally, any such entire antibody, antibody fragment, or substantially homologous fragment (such as, but not limited to, a substantially homologous fragment containing one or more conservative amino acid substitutions) may be derived from the 6C2 antibody. Thus, fragments or substantially homologous fragments may include one or a portion of the variable light and heavy chain sequences or CDR regions of 7E7 and/or 6C2, or may be substantially homologous to such sequences. Any such antibody may take the form of a human monoclonal antibody, a humanized antibody, a chimeric antibody, an affinity matured antibody, a mutated antibody or any such antibody generated by methodology as known in the art.

Light and heavy chain CDRs of 7E7 are as follows:

7E7

A. Peptide—light chain—RSGQSLVHRNGNTYLH (SEQ ID NO:7) (CDR1—Chothia and Kabat Methods), KVSNRFS (SEQ ID NO:8) (CDR2—Chothia and Kabat Methods), and SQSTHVPFT (SEQ ID NO:9) (CDR3—Chothia and Kabat Methods);

B. Peptide—heavy chain—GFTFTDY (SEQ ID NO:10) (CDR1—Chothia Method), RNKTKRYT (SEQ ID NO: 11) (CDR2—Chothia Method), and DDPYARFAY (SEQ ID NO: 12) (CDR3—Chothia Method);

C. Peptide—heavy chain—DYYMS (SEQ ID NO: 13) (CDR1—Kabat Method), FIRNKTKRYTTEYSASVKG (SEQ ID NO: 14) (CDR2—Kabat Method), and DDPYARFAY (SEQ ID NO: 12) (CDR3—Kabat Method);

D. Nucleic acid—light chain—AGATCTGGTCAGAGCCTTGTACACAGAAATGGAAACACCTATTTACAT (SEQ ID NO: 17) (CDR1—Chothia and Kabat Methods), AAAGTTTCCAACCGATTTTCT (SEQ ID NO:18) (CDR2—Chothia and Kabat Methods), and TCTCAAAGTACACATGTTCCATTCACG (SEQ ID NO: 19) (CDR3—Chothia and Kabat Methods);

E. Nucleic acid—heavy chain—GGGTTCACCTTCACTGACTAC (SEQ ID NO: 20) (CDR1—Chothia Method), AGAAACAAAACTAAACGTTACACA (SEQ ID NO:21) (CDR2—Chothia Method), and GATGATCCGTACGCACGGTTTGCTTAC (SEQ ID NO:22) (CDR3—Chothia Method); and F. Nucleic acid—heavy chain—GACTACTACATGAGC (SEQ ID NO:23) (CDR1—Kabat Method), TTTATTAGAAACAAAACTAAACGTTACACAACA-GAATACA GTGCATCTGTGAAGGGT (SEQ ID NO:24) (CDR2—Kabat Method), and GATGATCCGTACGCACGGTTTGCTTAC (SEQ ID NO:22) (CDR3—Kabat Method).

Light and heavy chain CDRs of 6C2 are as follows:

6C2

A. Peptide—light chain—KSSQSLLDSDGKTYLN (SEQ ID NO:28) (CDR1—Chothia and Kabat Methods), LVSKLDS (SEQ ID NO:29) (CDR2—Chothia and Kabat Methods), and WQGTHFPWT (SEQ ID NO:30) (CDR3—Chothia and Kabat Methods);

B. Peptide—heavy chain—GYSFTGY (SEQ ID NO:31) (CDR1—Chothia Method), NPYNGH (SEQ ID NO:32) (CDR2—Chothia Method), and SDS (CDR3—Chothia Method);

C. Peptide—heavy chain—GYFLS (SEQ ID NO:33) (CDR1—Kabat Method), RINPYNGHTFYNQKFKD (SEQ ID NO:34) (CDR2—Kabat Method), and SDS (CDR3—Kabat Method);

D. Nucleic acid—light chain—AAGTCAAGTCAGAGCCTCTTA GATAGTGATGGAAAGACATATTTGAAT (SEQ ID NO:35) (CDR1—Chothia and Kabat Methods), CTGGTGTCTAAACTGGACTCT (SEQ ID NO:36) (CDR2—Chothia and Kabat Methods), and TGGCAAGGTACACATTTTCCGTGGACG (SEQ ID NO:37) (CDR3—Chothia and Kabat Methods);

E. Nucleic acid—heavy chain—GGTTACTCATTTACTGGCTAC (SEQ ID NO:38) (CDR1—Chothia Method), AATCCTTACAATGGTCAT (SEQ ID NO: 39) (CDR2—Chothia Method), and TCTGACTCT (CDR3—Chothia Method); and F. Nucleic acid—heavy chain—GGCTACTTTTTGAGC (SEQ ID NO:40) (CDR1—Kabat Method), CGTATTAATCCTTACAATGGTCATACTTTCTAC AACCAGAAGTTCAAGGACAAG (SEQ ID NO:41) (CDR2—Kabat Method), and TCTGACTCT (CDR3—Kabat Method).

Another embodiment of the invention relates to a hybridoma which produces or secretes any such anti-beta antibody disclosed herein, including but not limited to hybridoma h7E7, which produces mAb 7E7, and the hybridoma h6C2, which produces the 6C2 mAb. As used herein, the terms "h7E7" and "h6C2" refer to hybridomas which produce the mAbs 7E7 and 6C2, respectively. The former was deposited with the American Type Culture Collection (ATCC, Manassas, Va.) on Feb. 24, 2015 (said deposit as described herein). The latter was deposited with the American Type Culture Collection (ATCC, Manassas, Va.) on Jun. 16, 2015 (said deposit as described herein). Another embodiment of the invention relates to a human monoclonal antibody, a humanized antibody, a chimeric antibody, affinity matured antibody, mutated antibody or any such antibody as known in the art which comprises the variable light chain, the variable heavy chain, or both the variable light chain and variable heavy chain of the 7E7 mAb (secreted from h7E7), including but not limited to the entire respective variable light or heavy chain, a fragment thereof or a substantially homologous fragment thereof from 7E7, any such fragment or substantially homologous fragment including but not limited to one, two, three, four, five or all six CDRs (as determined by either the Kabat and/or Chothia methodology, as described herein, as for example each of three CDRs from the variable light chain and/or each of three CDRs from the variable heavy chain) from the variable light chain and/or the variable heavy chain of the monoclonal antibody 7E7. An additional embodiment of the invention relates to a human monoclonal antibody, a humanized antibody, a chimeric antibody, affinity matured antibody, mutated antibody or any such antibody as known in the art which comprises the variable light chain, the variable heavy chain, or both the variable light chain and variable heavy chain of the 6C2 mAb (secreted from h6C2), including but not limited to the entire respective variable light or heavy chain, a fragment thereof or a substantially homologous fragment thereof from 6C2, any such fragment or substantially homologous fragment including but not limited to one, two, three, four, five or all six CDRs (as determined by either the Kabat and/or Chothia methodology, as described herein, as for example each of three CDRs from the variable light chain and/or each of three CDRs from the variable heavy chain) from the variable light chain and/or the variable heavy chain of the monoclonal antibody 6C2. Again, any such fragments may include one or a portion of the variable light and heavy chain sequences or CDR regions of 7E7 and/or 6C2, or may be substantially homologous to such sequences. Again, any such antibody may take the form of a human monoclonal antibody, a humanized antibody, a chimeric antibody, an affinity matured antibody, a mutated antibody or any such antibody generated by methodology as known in the art associated with improving the efficacy and/or safety of any such antibody, especially as related to administration to humans.

In certain aspects, the antibodies or portion of the anti-Aβ antibodies of the present invention are encoded in an isolated nucleic acid molecule, which includes (or encodes) one or more of the foregoing sequences, fragments, or homologues thereof. The nucleic acid molecule may encode the variable heavy chain and/or light chain and/or CDRs, including fragments thereof, of monoclonal antibodies 7E7 and/or 6C2. Such nucleic acid sequences may be cloned into an expression vector and inserted into a recombinant host cell. To this end, the present invention includes each of the isolated nucleic acids, the recombinant expression vectors encoding such isolated nucleic acids and host cell expressing such vectors.

Anti-Aβ antibodies of the present invention that incorporate one or more of the foregoing sequences, including substantially homologous variants thereof, may be provided as monoclonal antibodies, chimeric antibodies, humanized antibodies, human monoclonal antibodies, affinity matured antibodies, mutated antibodies, or other antibody variants known in the art.

The present invention also relates to treatment methods using one or a combination of the anti-Aβ antibodies of the present invention alone or in a pharmaceutical composition. One embodiment of a treatment method includes treating, preventing, or reducing one or more symptoms associated with Alzheimer's disease by administering to the mammal an effective amount of at least one anti-Aβ antibody of the present invention. In further embodiments, the treatment methods of the present invention include modulation of amyloid-beta aggregation and plaque formation in the brain or central nervous system of the subject, or otherwise treating amyloidosis in the subject. To this end, the treatments methods of the present invention may include any disease state characterized or otherwise associated with plaque formation that includes an amyloid-beta isomer, particularly Aβ(1-40) and/or Aβ(1-42) isoforms. In certain aspects, the present invention includes (1) the preparation of a pharmaceutical or diagnostic composition for prophylactic and therapeutic treatment of Alzheimer's disease, or any disease associated with the aggregation of amyloid-beta protein and/or amyloidosis, (2) monitoring the progression of such a disease, and/or a (3) establishing a risk or a prognosis of a subject at risk for the disease.

Additionally, the present invention includes diagnostic assays, drug screen assays, and the like for diagnosing in a bodily fluid of a patient or subject the presence of a soluble Aβ protein, an aggregation of Aβ proteins, or amyloidosis, particularly those including at least the isoforms having amino acids 1-40 and/or 1-42. Anti-Aβ antibodies of the present invention may also be used as a molecular tool to study the activity of amyloid-beta in an amyloid-beta expressing cell and/or the impact of amyloid-beta aggregation or amyloidosis to the cell, central nervous system, and subject.

In conjunction with such embodiments, the present invention also includes a kit for detecting amyloid-beta protein that includes (1) an antibody or a fragment thereof, capable of specifically binding in vitro to an epitope of an amyloid-beta protein (in certain aspects, an soluble, monomeric amyloid-beta isoform having amino acids 1-40 or 1-42; in other embodiments an oligomeric, including a tetrameric, isoform); and, (2) a reagent that binds, directly, or indirectly, to said antibody or the fragment thereof.

One of skill in the art will readily appreciate that the foregoing is not necessarily limiting to the invention and that additional embodiments and advantages of the present invention are readily available based on the disclosure provided herein.

To aid in the understanding of the invention, the following non-limiting definitions are provided:

As used herein, the term "epitope" refers to a site on an antigen to which B and/or T cells respond or a site on a molecule against which an antibody can or will be produced and/or to which an antibody can or will bind. For example, an epitope can be recognized by an antibody defining the epitope. An epitope can be either a "linear epitope" (where a primary amino acid primary sequence comprises the epitope; typically at least 3 contiguous amino acid residues, and more usually, at least 5, and up to about 8 to about 10 amino acids in a unique sequence) or a "conformational epitope" (an epitope wherein the primary, contiguous amino acid sequence is not the sole defining component of the epitope). A conformational epitope may comprise an increased number of amino acids relative to a linear epitope, as this conformational epitope recognizes a three-dimensional structure of the peptide or protein. For example, when a protein molecule folds to form a three dimensional structure, certain amino acids and/or the polypeptide backbone forming the conformational epitope become juxtaposed enabling the antibody to recognize the epitope. Methods of determining conformation of epitopes include but are not limited to, for example, x-ray crystallography, two-dimensional nuclear magnetic resonance spectroscopy and site-directed spin labeling and electron paramagnetic resonance spectroscopy. See, for example, Epitope Mapping Protocols in Methods in Molecular Biology, Vol. 66, Glenn E. Morris, Ed. (1996), the disclosure of which is incorporated in its entirety herein by reference.

As used herein, the terms "isolated" and "purified" are as used within the art, namely the state in which antibodies/specific binding members, nucleic acid molecules and such are found. Antibodies/specific binding members and nucleic acid molecules will be free or substantially free of material with which they are naturally associated such as other polypeptides or nucleic acids with which they are found in their natural environment, or the environment in which they are prepared (e.g. cell culture) when such preparation is by recombinant DNA technology (practiced in vitro) or in vivo. "Isolated" and "purified" covers any form containing the identified and characterized component(s) of the present invention following removal from that initial environment. Examples, but certainly not limitations, include pharmaceutical formulations, formulation with diluents, antibodies/specific binding members, nucleic acid molecules and portions thereof which have been modified (e.g., antibody glycosylation) either in vitro or in vivo and removed from that environment.

The terms "subject" or "patient" is meant to include any member of the Phylum Chordata, including, without limitation, humans and other primates, including nonhuman primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like.

The term "treating" or "treatment" of a disease refers to executing a protocol, which may include administering one or more drugs to a subject (human or otherwise), in an effort to alleviate signs or symptoms of the disease. Alleviation can occur prior to signs or symptoms of the disease appearing, as well as after their appearance. Thus, "treating" or "treatment" includes "preventing" or "prevention" or "reducing" signs or symptoms of disease. In addition, "treating" or "treatment" does not require complete alleviation of signs or symptoms, does not require a cure, and specifically includes protocols which have only a marginal positive effect on the subject.

As used herein, the terms "effective amount" or "pharmaceutically effective amount" of antibody, as provided herein, refers to a nontoxic but sufficient amount of the active ingredient in order to provide the desired biological result. An appropriate "effective" amount in any individual case may be determined by one of ordinary skill in the art using routine experimentation.

As used herein, the terms "pharmaceutically acceptable" or "pharmacologically acceptable" mean a material may be administered to an individual in a drug delivery device along with the formulated biological agent without causing any undesirable biological effects or interacting in a deleterious manner with any of the components of the composition in which it is contained (e.g., a "pharmaceutically acceptable composition").

As used herein, the phrases "physiologically acceptable carrier" and "pharmaceutically acceptable carrier" which may be interchangeably used refer to a carrier, diluent, and excipient that do not cause significant irritation to an organism and do not abrogate the biological activity and properties of the administered compound. An adjuvant is included under these phrases.

As used herein, the term "excipient" refers to an inert substance added to a pharmaceutical composition to further facilitate administration of an active ingredient.

By "specifically binding," it is generally meant that a binding molecule, e.g., an antibody, binds to an epitope via its antigen-binding domain, and that the binding entails some complementarity between the antigen-binding domain and the epitope. According to this definition, an antibody is said to "specifically bind" to an epitope when it binds to that epitope, via its antigen-binding domain more readily than it would bind to a random, unrelated epitope. A skilled artisan understands that an antibody can specifically bind to, or specifically recognize an isolated polypeptide comprising, or consisting of, amino acid residues corresponding to a linear portion of a noncontiguous epitope. The term "specificity" is used herein to qualify the relative affinity by which a certain antibody binds to a certain epitope. For example, antibody "A" can be deemed to have a higher specificity for a given epitope than antibody "B," or antibody "A" can be said to bind to epitope "C" with a higher specificity than it has for related epitope "D."

As used herein, the term "affinity" refers to a measure of the strength of the binding of an individual epitope with the CDR of a binding molecule, e.g., an immunoglobulin molecule; see, e.g., Harlow et al, Antibodies: A Laboratory Manual, Cold Spring Harbor Laboratory Press, 2nd ed. (1988) at pages 27-28. The affinity of an antibody for an antigen can be determined experimentally using any suitable method; see, for example, Berzofsky et al, "Antibody-Antigen Interactions" In Fundamental Immunology, Paul, W. E., Ed., Raven Press New York, N.Y. (1984), Kuby, Janis Immunology, W. H. Freeman and Company New York, N.Y. (1992), and methods described herein. General techniques for measuring the affinity of an antibody for an antigen include ELISA, RIA, and surface plasmon resonance. The measured affinity of a particular antibody-antigen interaction can vary if measured under different conditions, e.g., salt concentration, pH. Thus, measurements of affinity and other antigen-binding parameters, e.g., ¾, $IC_{50}$, are preferably made with standardized solutions of antibody and antigen, and a standardized buffer.

As used herein, "conservatively modified variants" or "conservative amino acid substitution" or the like refers to substitutions of amino acids are known to those of skill in this art and may be made generally without altering the biological activity of the resulting molecule. Those of skill in this art recognize that, in general, single amino acid substitutions in non-essential regions of a polypeptide do not substantially alter biological activity (see, e.g., Watson, et al., Molecular Biology of the Gene, The Benjamin/Cummings Pub. Co., p. 224 (4th Edition 1987)). Such exemplary substitutions are preferably made in accordance with those set forth below as follows: (original residue)/[conservative substitution]: (Ala)/[Gly, Ser]; (Arg)/[Lys, His] (Asn)/[Gln, His]; (Asp)/[Glu, Asn]; (Cys)/[Ser, Ala]; (Gln)/[Asn]; (Glu)/[Asp, Gin]; (Gly)/[Ala]; (His)/[Asn, Gin]; (Ile)/[Leu, Val]; (Leu)/[Ile, Val]; (Lys)/[Arg, His]; (Met)/[Leu, Ile, Tyr]; (Phe)/[Tyr, Met, Leu]; (Pro)/[Ala]; (Ser)/[Thr]; (Thr)/[Ser]; (Trp)/[Tyr, Phe]; (Tyr)/[Trp, Phe]; (Val)/[Ile, Leu].

Testing was performed (and results provided) in triplicate for each composition. (y-axis=OD$_{450\ nm}$).

Figure 11:
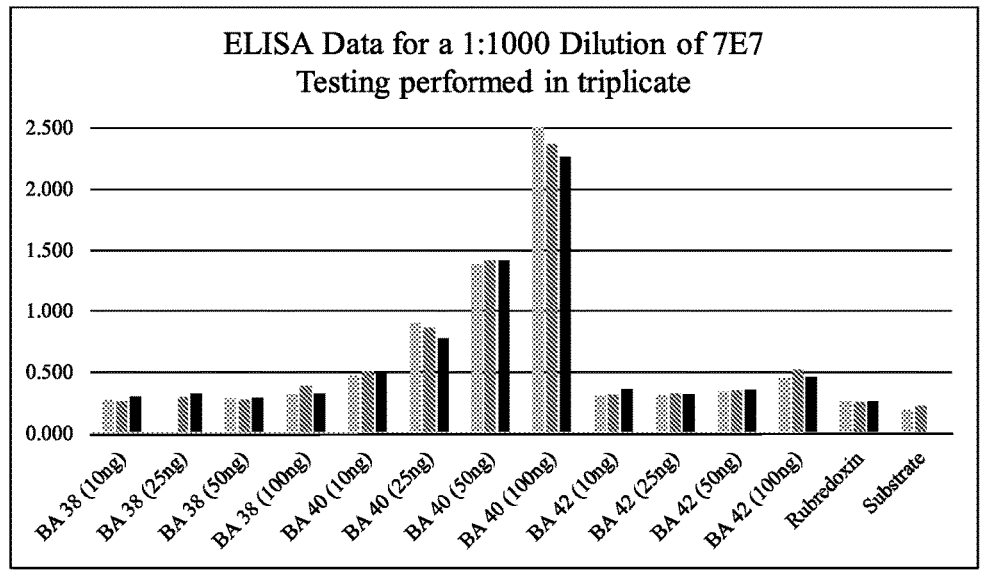

FIG. 11 provides a graphic illustration of the ELISA data for mAb 7E7 on rub-Aβ 1-38, rub-Aβ 1-40, and rub-Aβ 1-42 under varying peptide concentrations at a dilution of 1:1,000. Testing was performed (and results provided) in triplicate for each dilution. (y-axis=OD$_{450\ nm}$).

Figure 12:
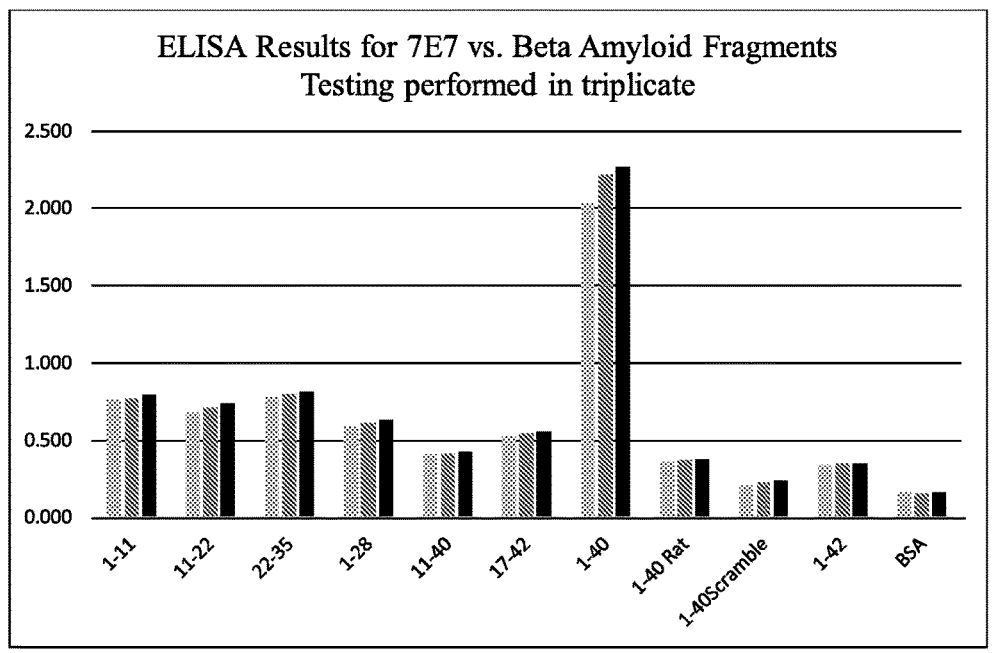

FIG. 12 provides a graphic illustration of the ELISA data for mAb 7E7 on varying fragments of the Aβ peptide. Testing was performed (and results provided) in triplicate for each composition. (y-axis=OD$_{450\ nm}$).

Figure 13:
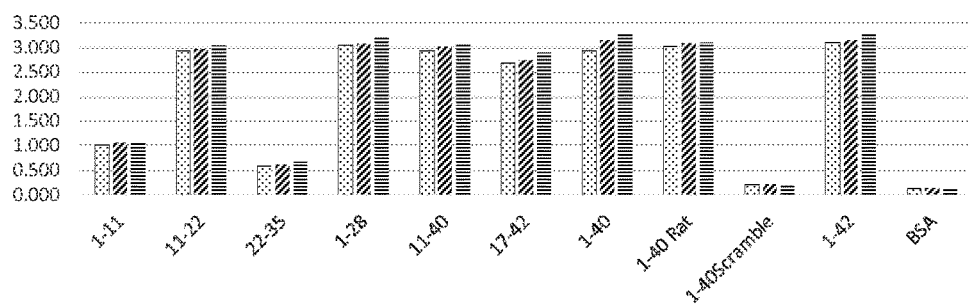

FIG. 13 provides a graphic illustration of the ELISA data for positive control mAb 4G8 on varying fragments of the Aβ peptide. Testing was performed (and results provided) in triplicate for each composition. (y-axis=OD$_{450\ nm}$).

Figure 14:
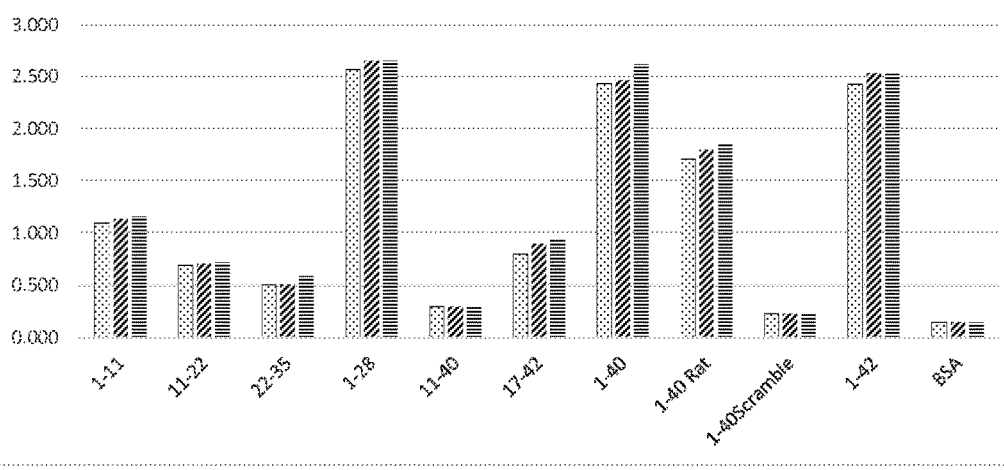

FIG. 14 provides a graphic illustration of the ELISA data for positive control mAb 6E10 on varying fragments of the Aβ peptide. Testing was performed (and results provided) in triplicate for each composition. (y-axis=OD$_{450\ nm}$).

Figure 15:
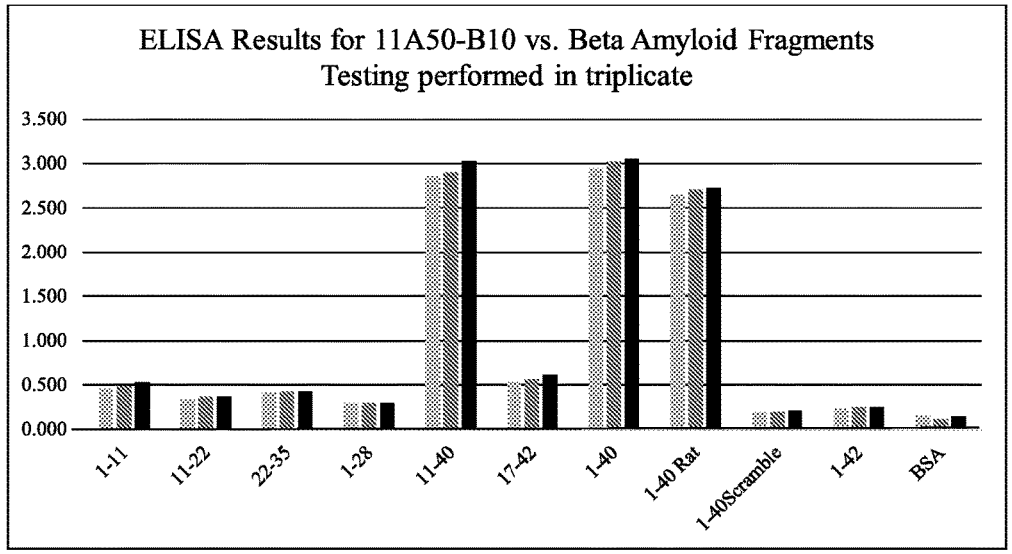

FIG. 15 provides a graphic illustration of the ELISA data for positive control mAb 11A50-B10 on varying fragments of the Aβ peptide. Testing was performed (and results provided) in triplicate for each composition. (y-axis=OD$_{450\ nm}$).

Figure 16:
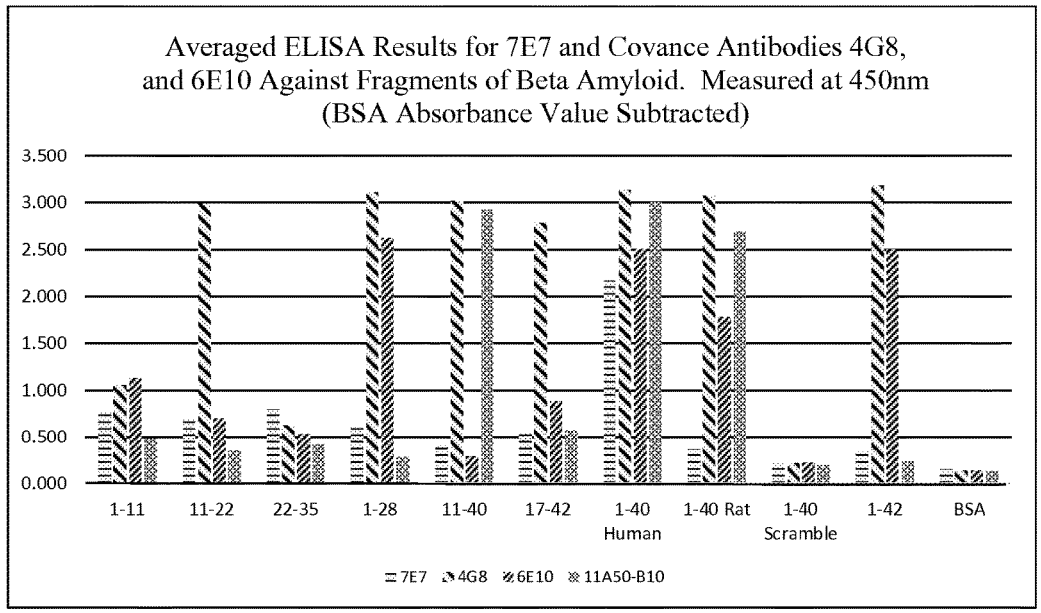

FIG. 16 provides a graphic illustration comparing the data from FIGS. 12-15. (y-axis=OD$_{450\ nm}$).

Figure 17:
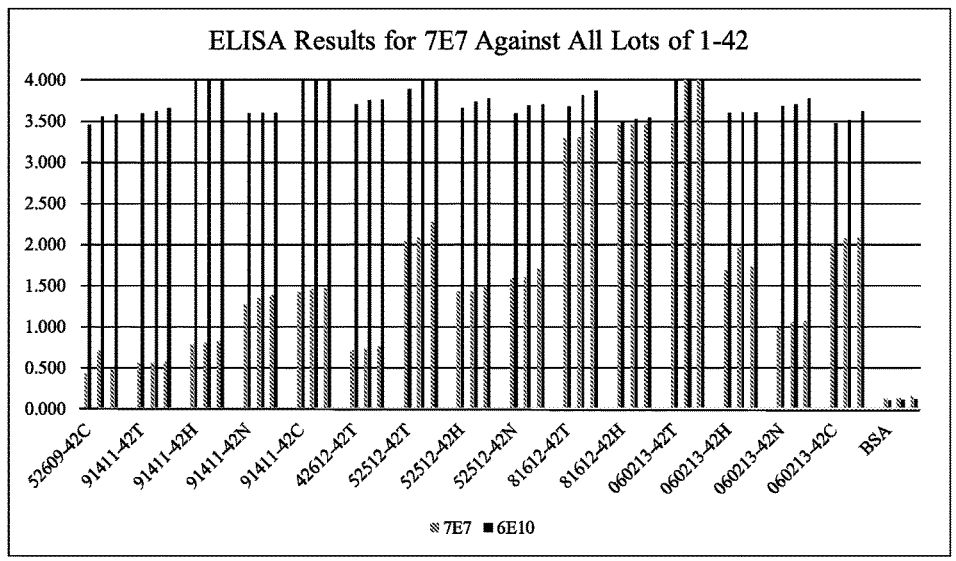

FIG. 17 provides a graphic illustration of ELISA data for binding of 7E7 to varying lots of Aβ 1-42. (y-axis=OD$_{450\ nm}$).

Figure 18:
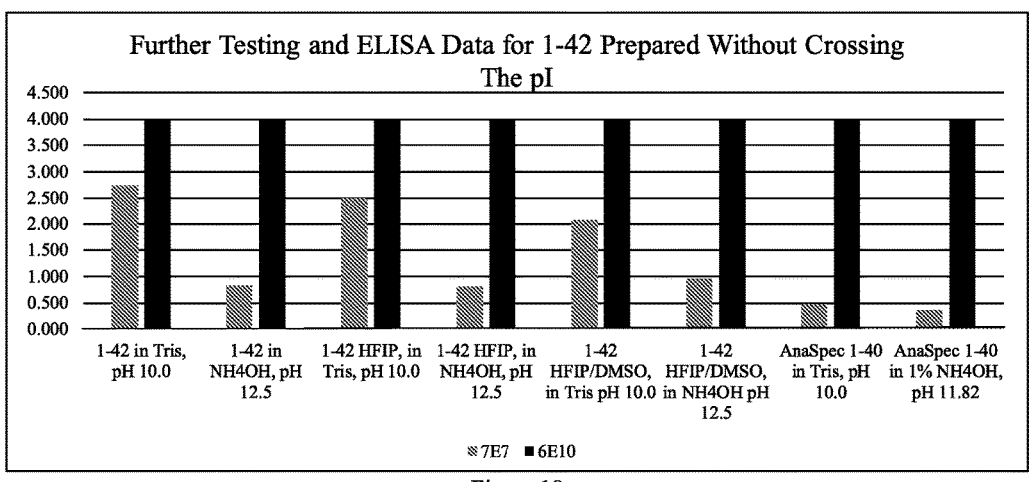

FIG. 18 provides a graphic illustration of ELISA data for 7E7 and 6E10 using Aβ (1-42) prepared without crossing the isoelectric point. (y-axis=OD$_{450\ nm}$).

Figure 19:
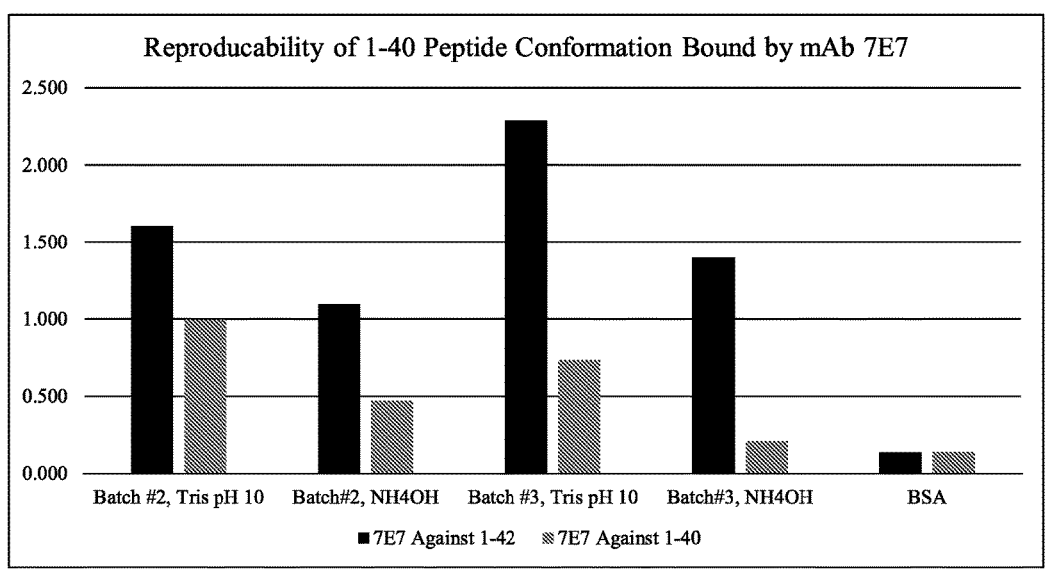

FIG. 19 provides the reproducibility of 7E7 binding to Aβ (1-40) and Aβ (1-42) in varying binding conditions where Aβ was prepared without crossing the isoelectric point. (y-axis=OD$_{450\ nm}$).

Figure 20:
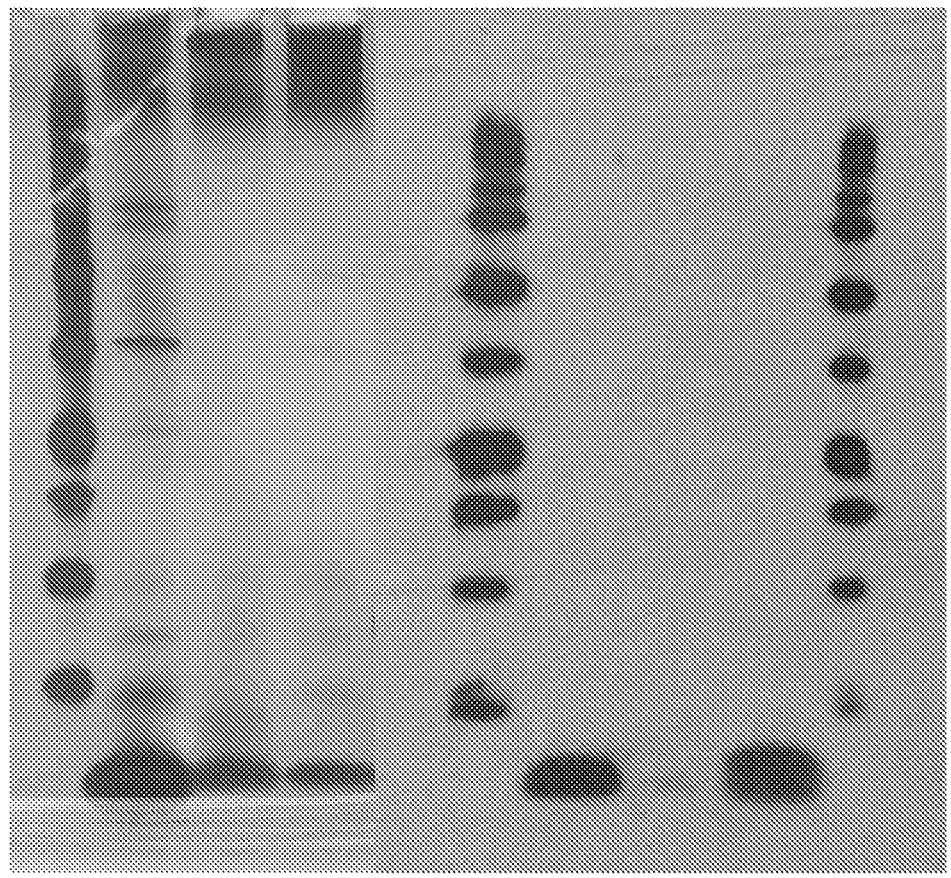

FIG. 20 illustrates a silver stained Bio-Rad 12% Bis-Tris Criterion XT Precast Gel of 7E7 on the left, and on the right is the corresponding western blot of the same samples with 7E7 as the primary antibody.

Figure 21:
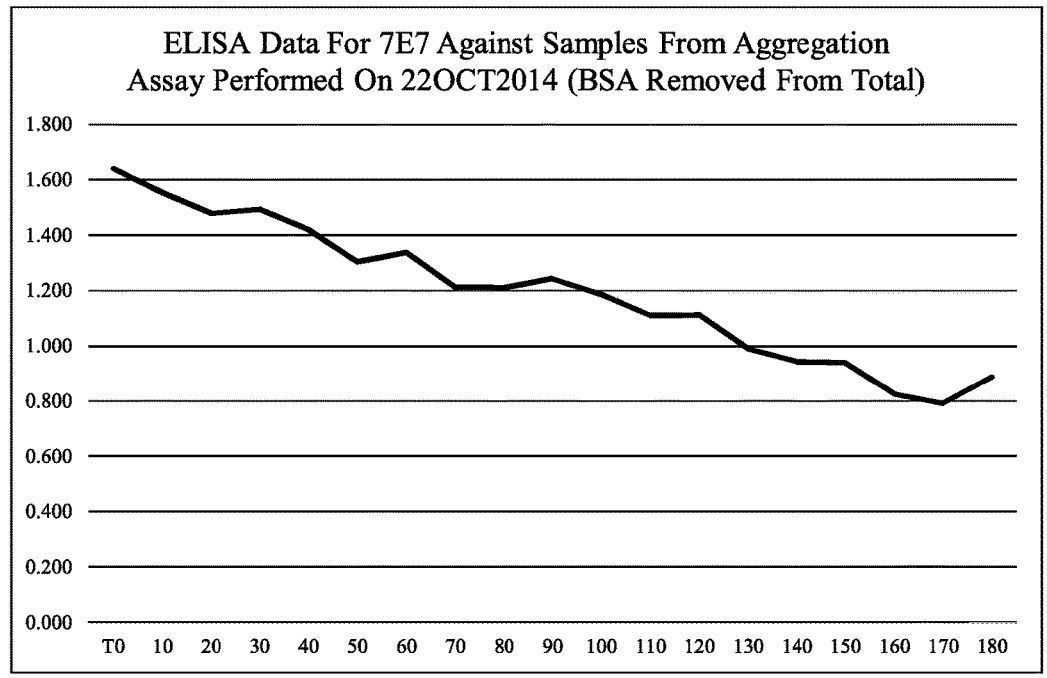

FIG. 21 provides a graphic illustration of the trend from ELISA data of 7E7 against samples that were obtained during an assay which forces aggregation of 1-42. The values on the X-Axis represent time (in minutes). (y-axis=OD$_{450\ nm}$).

Figure 22:
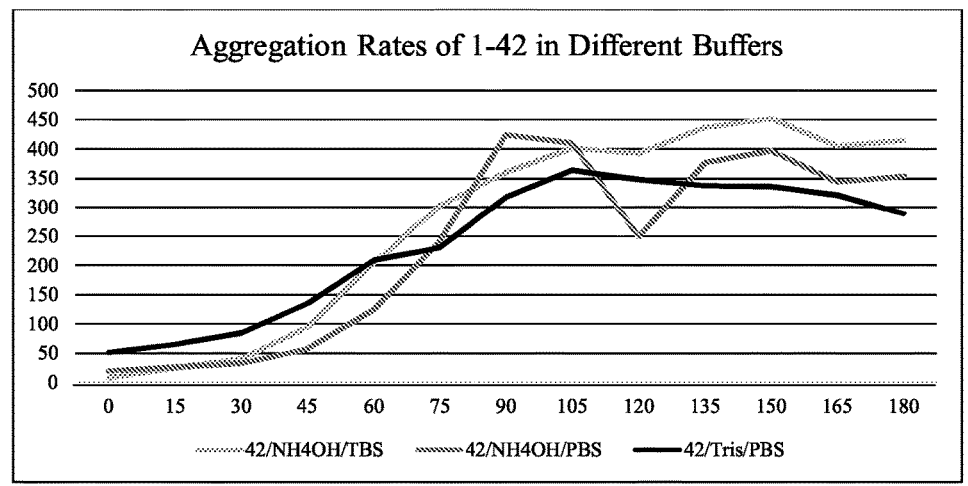

FIG. 22 provides a graphic illustration of Thioflavin T results from the same aggregation assay as in FIG. 21 using varying buffers.

Figure 23:
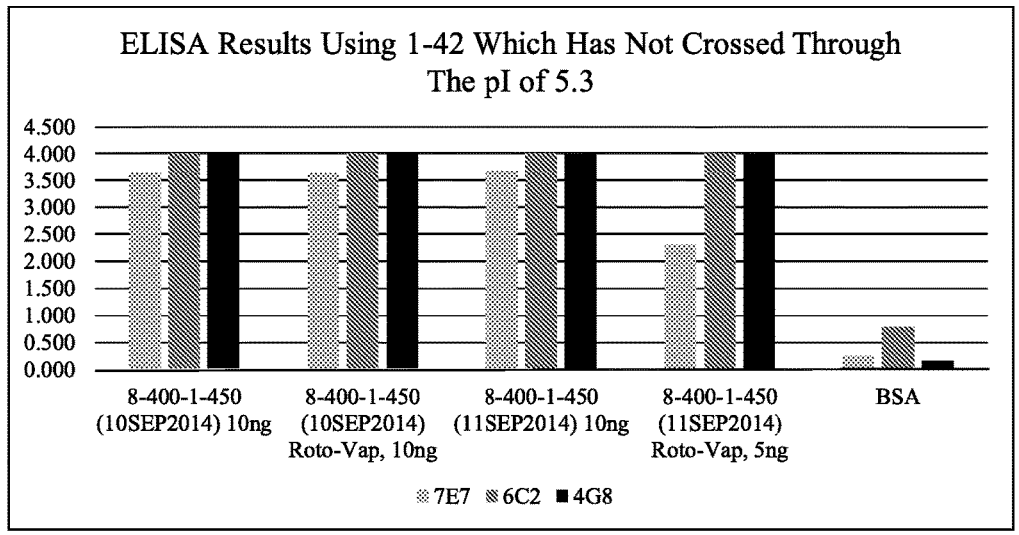

FIG. 23 provides a graphic illustration of ELISA results with 7E7 and 6C2 tested against 1-42 prepared in the same manner as described herein, with 4G8 acting as a control. (y-axis=OD$_{450\ nm}$).

Figure 24:
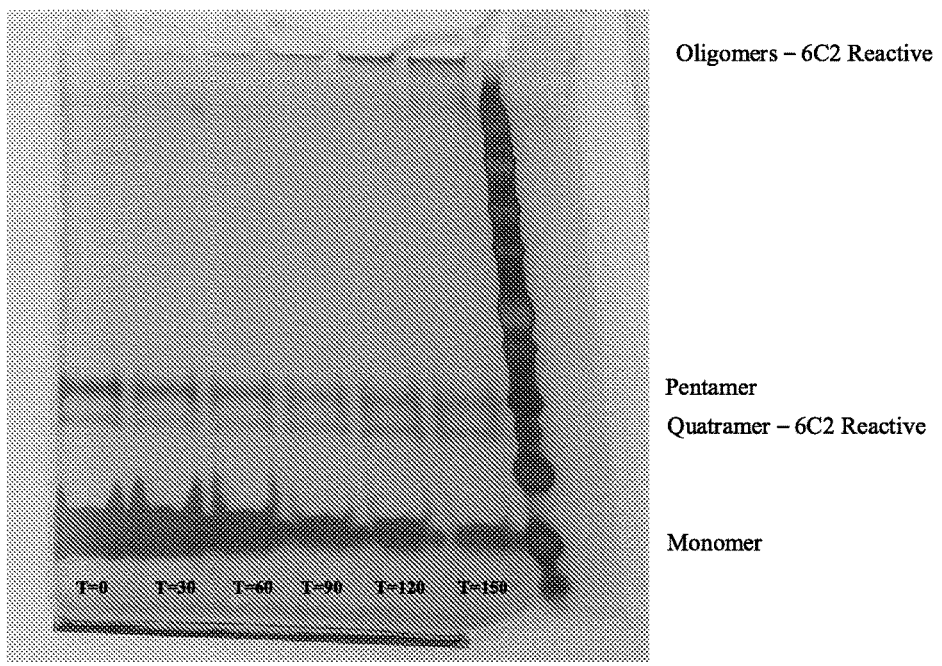

FIG. 24 provides SDS-PAGE gel results containing samples from an Aβ aggregation assay of Aβ (1-42) with 6C2 mAb.

Figure 25:
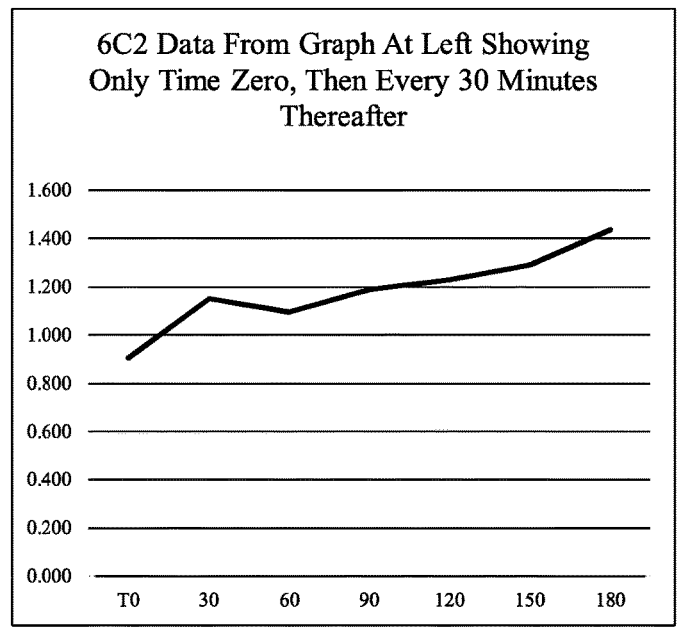

FIG. 25 provides graphic illustration of the ELISA results with 6C2 illustrating that the ELISA data gathered from testing it against aggregating Aβ (1-42) samples was similar to the curve generated from the Thioflavin T samples. (y-axis=OD$_{450\ nm}$).

Figure 26:
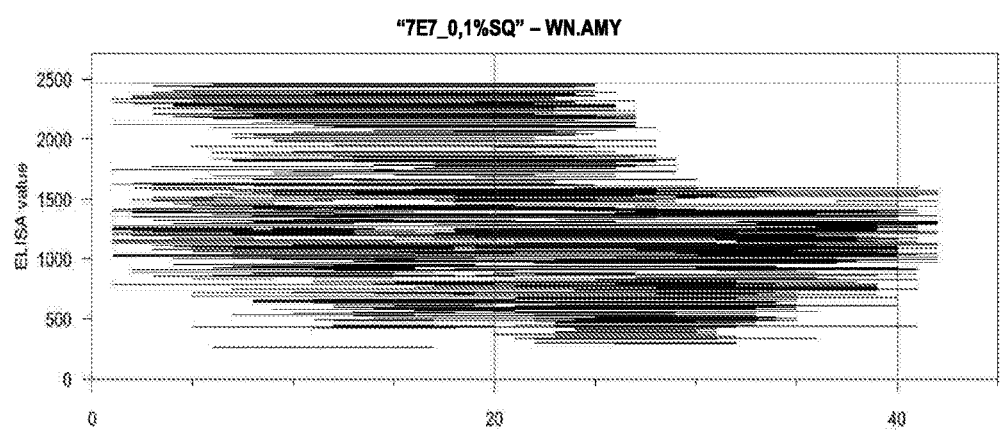

FIG. 26 illustrates the binding affinity results of 7E7, showing no clear cutoff point that preserves a common core essential for binding of the antibody.

Figure 27:
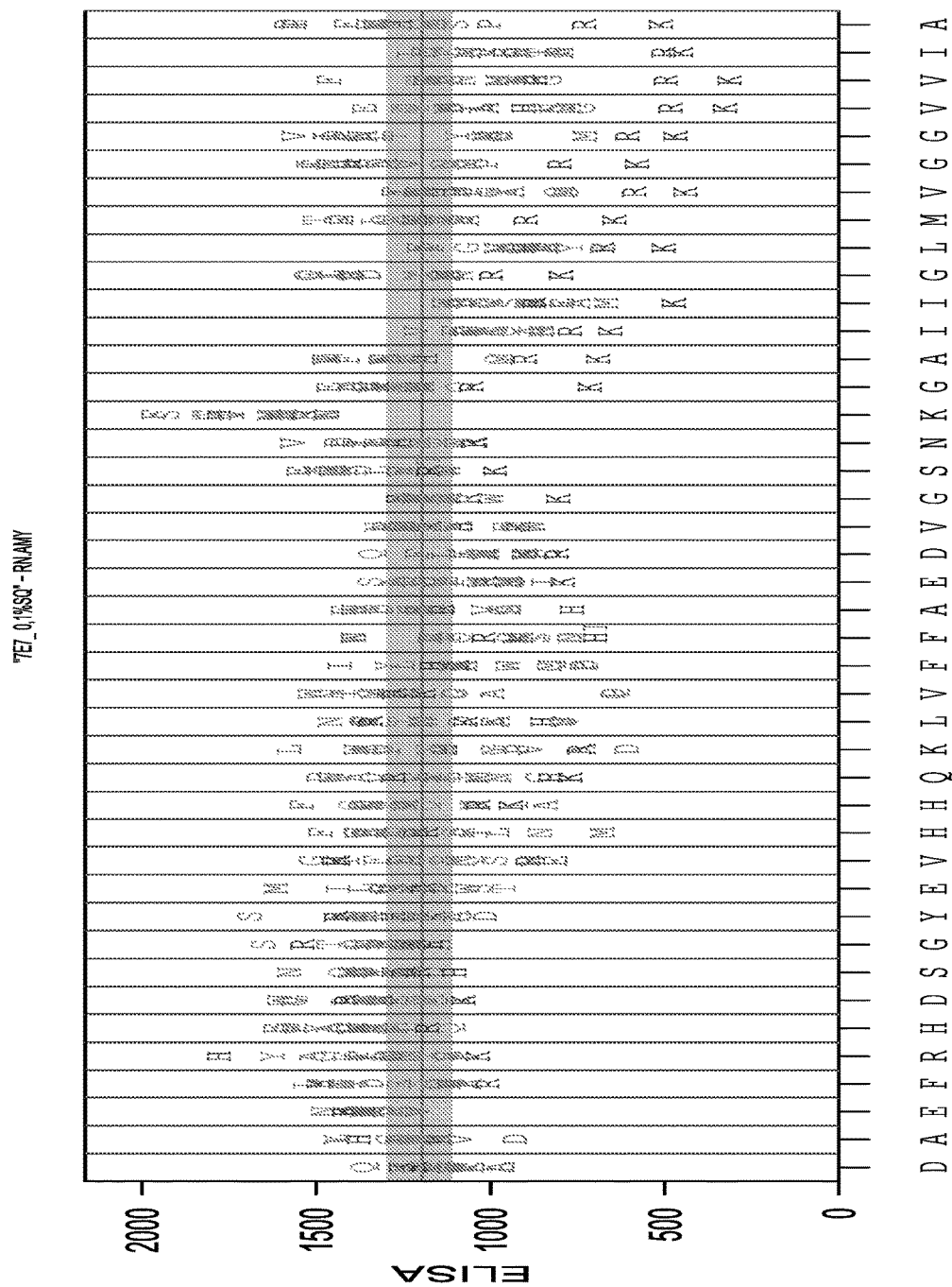

FIG. 27 illustrates non-specific decrease of binding of 7E7 when residues in the range between V12 and V24 are replaced. A trend toward decreased binding can be observed when extra positive charges are introduced near the C-terminus of the original peptide sequence.

Figure 28:
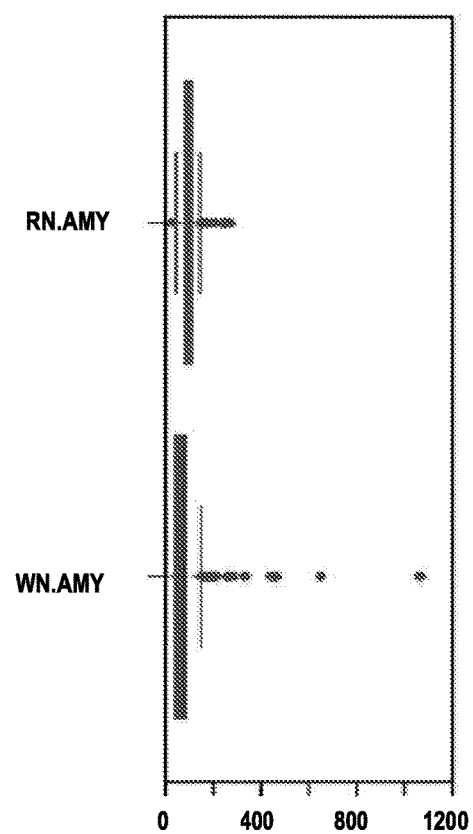

FIG. 28 illustrates box plot graphs of raw data of the 6C2 mAb screen. The bottom and top of the boxes are the 25$^{th}$ and 75$^{th}$ percentile of the data. The band near the middle of the box is the 50$^{th}$ percentile (the median). The whiskers are at 1.5 the inter-quantile range, and indication of statistical outliers within the dataset.

Figure 29:
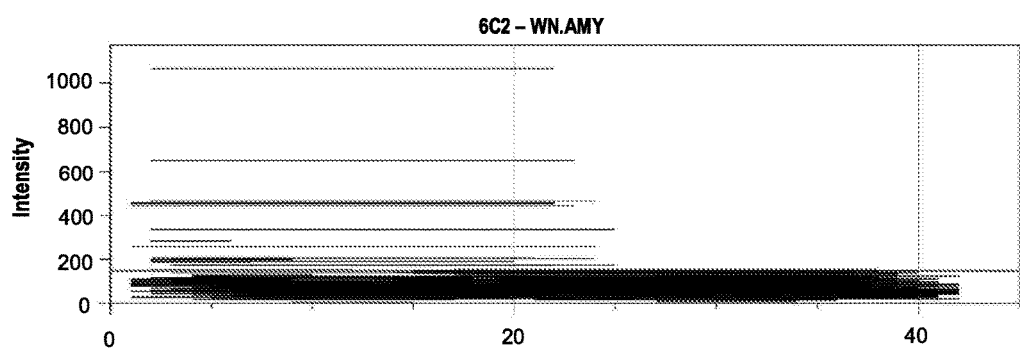

FIG. 29 illustrates the binding affinity results of 6C2, showing a contiguous series from A2 to E22 is needed.

DETAILED DESCRIPTION OF THE INVENTION

Amyloid-beta protein aggregation and the formation of amyloid plaques is a molecular hallmark for Alzheimer's disease (AD). Accordingly, it presents a viable target for the study of such a disease (or for any neurodegenerative disease state associated with Aβ aggregation). Alternatively, it presents a viable target for a method of diagnosing, monitoring, studying, and/or treating a patient diagnosed with such a disease.

In certain non-limiting aspects, the present invention relates to isolated antibodies that specifically interact with and show measurable affinity to one or more epitopes of one or more Aβ protein isoforms, particularly the epitopes discussed herein, referred to generally herein as "anti-Aβ antibodies." Such antibodies may be used for the identification of and/or modulation of Aβ protein activity, aggregation or amyloidosis, to study its effects on cell function and, in certain embodiments, for the treatment, prevention, diagnosis, and/or monitoring of a disease or condition associated with the Aβ protein expression, aggregation, or amyloidosis. In certain embodiments, the anti-Aβ antibodies may be administered to a subject to treat or prevent a neurodegenerative disease state characterized by or associated with Aβ aggregation or amyloidosis, including particularly Alzheimer's disease, and/or for preventing the formation of amyloid plaques by the Aβ protein, which is a symptom of the disease. In certain embodiments, the anti-Aβ antibodies may be used to diagnosis and/or monitor such neurodegenerative diseases by monitoring the formation and concentration of amyloid plaques in a patient and/or the concentration of soluble Aβ protein in the patient.

As used herein, the terms "amyloid-beta proteins" or "amyloid-beta protein isoforms" refer to any form or fragment of the Aβ protein. In certain aspects, however, the form of Aβ protein is expressed in the human brain and contains amino acids 1-40 and/or 1-42. As used herein, such isoforms are defined, as follows:

```
Aβ(1-40):
                                              (SEQ ID NO: 1)
DAEFRHDSGYEVHHQKLVFFAEDVGSNKGAIIGLMVGGVV

Aβ(1-42):
                                              (SEQ ID NO: 2)
DAEFRHDSGYEVHHQKLVFFAEDVGSNKGAIIGLMVGGVVIA.
```

The present invention, however, is not limited to these forms and may include any variant, natural or synthetic, or mutated sequence that exhibits the properties of an amyloid-beta protein (particularly those included in Aβ aggregation or amyloidosis) in or around a targeted cell or cell population that are discussed herein or otherwise known in the art.

The targeted epitope(s) of the anti-A13 antibodies include any one or more peptide sequences of a Aβ isoform against which one or more antibodies of the present invention will specifically bind with measurable affinity. Anti-A antibodies in certain aspects bind only to monomeric forms of the Aβ isoform, particularly though not exclusively Aβ(1-40) and/or Aβ(1-42). In further aspects, the anti-Aβ antibodies bind only to oligomeric forms of the Aβ isoform, particularly though not exclusively Aβ(1-40) and/or Aβ(1-42). In even further aspects, the anti-Aβ antibodies bind only to an aggregated tetrameric form of the AB isoform, particularly though not exclusively Aβ(1-40) and/or Aβ(1-42).

Such sequences may include active or non-active regions of the protein and include either linear epitopes and/or conformation epitopes, as defined herein. In certain aspects, they include one or more regions where the binding of the antibodies results in a measurable reduction of the Aβ protein activity in the host cell, aggregation, or amyloidosis. To this end, in certain aspects, the epitope is at a position of the protein where the binding of the antibody modifies protein activity, and in certain aspects self-assembly, aggregation into amyloid-plaques, or amyloidosis, such as active site blocking, steric hindrance, allosteric inhibition, or the like.

In certain embodiments, the epitope is a linear epitope having the sequence VHHQKLVFFAEDV (SEQ ID NO: 3), which resides at residues 12-24 of the Aβ 1-40 and 1-42 isoforms. In further embodiments, the anti-Aβ antibodies bind to such an epitope under conditions where at least the asparagine residue at position 27 of the Aβ(1-40) and/or Aβ(1-42) has not undergone post translational modification, specifically deamidation. In further embodiments, the anti-Aβ antibodies, or fragments thereof, bind to such epitopes when the Aβ(1-40) and/or Aβ(1-42) is present in a soluble, monomeric form.

In certain embodiments, the epitope is a linear epitope or a conformational epitope having or contained within the sequence AEFRHDSGYEVHHQKLVFFAE (SEQ ID NO: 4), which resides at residues 2-22 of the Aβ 1-40 and 1-42 isoforms. In further embodiments, the anti-Aβ antibodies bind to such an epitope under conditions where at least the asparagine residue at position 27 of the Aβ(1-40) and/or Aβ(1-42) has not undergone post translational modification, specifically deamidation. In even further embodiments, the anti-Aβ antibodies, or fragments thereof, bind to such epitopes when the Aβ(1-40) and/or Aβ(1-42) is present in an oligomeric form. In even further embodiments, the anti-Aβ antibodies, or fragments thereof, bind to such epitopes when the Aβ(1-40) and/or Aβ(1-42) is present in an aggregated tetrameric form.

The epitopes of the present invention are not limited to the exact sequence within SEQ ID NO: 3 or SEQ ID NO: 4 and may include any sequence having at least 70% homology, 80% homology, 90% homology or 99% homology, or any homology where measurable binding affinity to the epitope is detected, particularly binding affinities consistent (i.e within 25%, 20%/a, 10%, 5%, 1%, or the like) with the results provided herein.

In certain embodiments, the anti-Aβ antibodies of the present invention include two identical heavy chains and two light chains containing one or more of the antigen binding domains identified herein. The light chain includes one variable domain ($V_L$) and one constant domain ($C_L$). The heavy chain also includes one variable domain ($V_H$) and, depending on the class or isotype of antibody, three or four constant domains ($C_{H1}$, $C_{H2}$, $C_{H3}$ and $C_{H4}$). Isotypes include, but are not limited to, IgA, IgD, IgE, IgG, and IgM, with IgA and IgG further subdivided into subclasses or subtypes. In certain non-limiting inventions, the isotype of the present invention is IgG, which includes one or a combination of its sub-types (e.g. IgG1, IgG2, IgG3, and IgG4).

The paired heavy chain constant domains are generally understood to define the Fc region of the antibody. Based on its sequence, it provides the antibody with one or more of the isotypes discussed above. The Fc region is associated with Fc receptor binding, activation of complement-mediated cytotoxicity and antibody-dependent cellular-cytotoxicity. To this end, it is at least partially responsible for eliciting immunological reactivity.

The $V_L$ and $V_H$ domains of the antibody are generally defined as the "Fv" region and constitute the antigen-binding site. A single chain Fv (scFv) includes a protein containing a $V_L$ domain and a $V_H$ domain on one polypeptide chain, wherein the N terminus of one domain and the C terminus of the other domain are joined by a flexible linker. A "Fab" region refers to the portion of the antibody including the $V_L$-$C_L$ (i.e, a light chain) and $V_H$-$C_H$ (also designated "Fd").

Present within each $V_L$ and $V_H$ domain of the Fv region of the antibody are eight framework regions (FR) and six total complementarity-determining regions (CDRs). Four FRs and three CDRs are found in each $V_L$ chain and the $V_H$ chain. The four FR regions (FR1, FR2, FR3, and FR4) are relatively conserved, while the CDR regions (CDR1, CDR2, and CDR3) represent the hypervariable portion of the antibody primarily responsible for the recognition and binding of the targeted epitope sequence. Typically, the FR and CDRs regions are arranged from $NH_2$ terminus to the COOH terminus of the antibody as follows: FR1, CDR1, FR2, CDR2, FR3, CDR3, FR4.

In certain aspects, the anti-A1 antibodies of the present invention include isolated monoclonal antibodies 7E7 and/or 6C2, as defined herein. In further embodiments, the present invention relates to a hybridoma that produces or secretes an anti-Aβ antibody, including but in no way limited to hybridoma h7E7 (which secrets 7E7), and h6C2 (which secretes 6C2). Hybridoma h7E7 also refers to the hybridoma deposited with the American Type Culture Collection on Feb. 24, 2015, as described more fully herein. Hybridoma h6C2 also refers to the hybridoma deposited with the American Type Culture Collection on Jun. 16, 2015, as described more fully herein.

The following Tables 1 and 2 provide the amino acid sequences of the variable light chain and variable heavy chain of the 7E7 antibody:

TABLE 1

Variable Light Chain Sequences

7E7 DVVMTQTPLSLPVSLGDQASISCRSGQSLVHRNGNTYLHWYLQKPG
    QSPKLLIYKVSNRFSGVPDRFSGSGTGTDFTLKISRVEAEDLGVYFC
    SQSTHVPFTFGSGTKLEIK (SEQ ID NO: 5)

TABLE 2

Variable Heavy Chain Sequences

7E7 EVKLVESGGGLVQPGSSQRLSCATSGFTFTDYYMSWVRQPPGKALE
    WLGFIRNKTKRYTTEYSASVKGRFTISRDNSQSILYLQMNTLRAEDS
    ATYYCARDDPYARFAYWGQGTLVTVSA (SEQ ID NO: 6)

The following Tables 3 and 4 provide the amino acid sequences of the variable light chain and variable heavy chain of the 6C2 antibody:

TABLE 3

Variable Light Chain Sequences

6C2 DVVMTQTPLTLSVTIGQPASISCKSSQSLLDSDGKTYLNWLLQRPG
QSPKRLIFLVSKLDSGVPDRFTGSGSGTDFTLKISSVEAEDLGIY
YCWQGTHFPWTFGGGTKLEIK (SEQ ID NO: 42)

TABLE 4

Variable Heavy Chain Sequences

6C2 EVQLQQSGPELVKPGASVKISCKASGYSFTGYFLSWVKQSHGRSLEW
IGRINPYNGHTFYNQKFKDKATLTVDKSSTTAHMELLSLTSEDSAVY
YCAGSDSWGQGTTLTVSS (SEQ ID NO: 43)

The following Tables 5-7 (7E7 antibody) and Tables 8-10 (6C2 antibody) provide the amino acid sequences of the variable light chain CDRs and the variable heavy chain CDRs, respectively. Table 5 (7E7) and Table 8 (6C2) provide the variable light chain CDR sequences according to both the Chothia and Kabat Method. Table 6 (7E7) and Table 9 (6C2) provide the variable heavy chain CDR sequences according to the Chothia Method. See Chothia et al., "Canonical structures for the hypervariable regions of immunoglobulins," J. Mol. Biol., 1987, Aug. 20; 196(4): 901-917, the contents of which are incorporated by reference herein in its entirety. Table 7 (7E7) and Table 10 (6C2) provide the variable heavy chain CDR sequences according to the Kabat Method. See Kabat et al., "Sequences of Proteins of Immunological Interest," U.S. Department of Health and Human Services, 1983, the contents of which are incorporated by reference herein in its entirety.

TABLE 5

Variable Light Chain CDR Sequences - Chothia & Kabat Method

| CDR1 | CDR2 | CDR3 |
|---|---|---|
| 7E7 RSGQSLVHRNGNTYLH (SEQ ID NO: 7) | KVSNRFS (SEQ ID NO: 8) | SQSTHVPFT (SEQ ID NO: 9) |

TABLE 6

Variable Heavy Chain CDR Sequences - Chothia Method

| CDR1 | CDR2 | CDR3 |
|---|---|---|
| 7E7 GFTFTDY (SEQ ID NO: 10) | RNKTKRYT (SEQ ID NO: 11) | DDPYARFAY (SEQ ID NO: 12) |

TABLE 7

Variable Heavy Chain CDR Sequences - Kabat Method

| CDR1 | CDR2 | CDR3 |
|---|---|---|
| 7E7 DYYMS (SEQ ID NO: 13) | FIRNKTKRYTTEYSASVKG (SEQ ID NO: 14) | DDPYARFAY (SEQ ID NO: 12) |

TABLE 8

Variable Light Chain CDR Sequences - Chothia & Kabat Method

| CDR1 | CDR2 | CDR3 |
|---|---|---|
| 6C2 KSSQSLLDSDGKTYLN (SEQ ID NO: 28) | LVSKLDS (SEQ ID NO: 29) | WQGTHFPWT (SEQ ID NO: 30) |

TABLE 9

Variable Heavy Chain CDR Sequences - Chothia Method

| CDR1 | CDR2 | CDR3 |
|---|---|---|
| 6C2 GYSFTGY (SEQ ID NO: 31) | NPYNGH (SEQ ID NO: 32) | SDS |

TABLE 10

Variable Heavy Chain CDR Sequences - Kabat Method

| CDR1 | CDR2 | CDR3 |
|---|---|---|
| 6C2 GYFLS (SEQ ID NO: 33) | RINPYNGHTFYNQKFKD (SEQ ID NO: 34) | SDS |

The anti-Aβ antibodies of the present invention may include the foregoing variable light chain, variable heavy chain, and/or CDR peptide sequences exactly or may be sufficiently homologous or substantially the same as one of the foregoing sequences, so as to exhibit measurable binding affinity to the Aβ protein, including to one or more of the epitopes identified herein and in certain particular embodiments to monomeric forms of the 1-40 and/or 1-42 isoforms and/or oligomeric forms of the peptides. Substantially the same amino acid sequence or sufficiently homologous is defined herein as a sequence with at least 70%, at least about 80%, at least about 90%, at least about 95% or at least about 99% homology or identity to a compared amino acid sequence, as determined by the FASTA search method in accordance with Pearson and Lipman, 1988, Proc. Natl. Acad. Sci. USA 85:2444-2448, the contents of which are incorporated herein by reference. Anti-Aβ antibodies of the present invention may be provided as naturally occurring antibodies, bivalent fragments such as (Fab')$_2$, monovalent fragments such as Fab, single chain antibodies, single chain Fv (scFv), single domain antibodies, multivalent single chain antibodies, diabodies, triabodies, and the like that bind with measurable affinity to the targeted antigen or epitopes. In any of the above embodiments, the variant of the antibody or antibody fragment of the invention may comprise one, two or three conservatively modified amino acid substitutions. In any of the above embodiments, the antibody or antibody fragment of the invention may comprise a human heavy chain constant region or a variant thereof, wherein the variant comprises up to 20 conservatively modified amino acid substitutions; and/or a human light chain constant region or a variant thereof, wherein the variant comprises up to 20 conservatively modified amino acid substitutions. In some embodiments, the variant may comprise up to 10 conservatively modified amino acid substitutions. In some embodiments, the variant may comprise up to 5 conservatively modified amino acid substitutions. In some embodiments, the variant may comprise up to 3 conservatively modified amino acid substitutions. In any of the above embodiments, the human heavy chain constant region or variant thereof may be, but is in no way limited to, the IgG isotype (e.g., IgG, IgG2, IgG3, and IgG4 sub-types), IgA isotype (e.g., IgA1, IgA2 subtypes), IgD isotype, IgE isotype, or IgM isotype.

Embodiments of the invention include the entire antibody, a fragment or substantially homologous fragment of the monoclonal antibody 7E7. Any such entire antibody, fragment of substantially homologous fragment (such as, but not limited to, a substantially homologous fragment containing one or more conservative amino acid substitutions) being derived from the 7E7 antibody, and any such fragment or substantially homologous fragment including but not limited to one, two, three, four, five or all six CDRs (as determined by either the Kabat and/or Chothia methodology, as described herein, as for example each of three CDRs from the variable light chain and/or each of three CDRs from the variable heavy chain) from the variable light chain and/or the variable heavy chain of the monoclonal antibody 7E7. Additional embodiments include the entire antibody, a fragment or substantially homologous fragment of the monoclonal antibody 6C2, with any such entire antibody, fragment or substantially homologous fragment (such as, but not limited to, a substantially homologous fragment containing one or more conservative amino acid substitutions) being derived from the 6C2 antibody, and any such fragment or substantially homologous fragment including but not limited to one, two, three, four, five or all six CDRs (as determined by either the Kabat and/or Chothia methodology, as described herein, as for example each of three CDRs from the variable light chain and/or each of three CDRs from the variable heavy chain) from the variable light chain and/or the variable heavy chain of the monoclonal antibody 6C2. Fragments may include, but are not limited to, one or a portion of the variable light and/or heavy chain sequences or CDR regions of 7E7 and/or 6C2, or may be substantially homologous to such sequences. Again, any such antibody may take the form of a human monoclonal antibody, a humanized antibody, a chimeric antibody, affinity matured antibody, mutated antibody or any such antibody generated by methodology as known in the art.

Another embodiment of the invention relates to hybridoma h7E7, as well as the mAb 7E7, as produced or secreted from h7E7.

Another embodiment of the invention relates to hybridoma h6C2, as well as the mAb 6C2, as produced or secreted from h6C2.

Another embodiment of the invention relates to a human monoclonal antibody, a humanized antibody, a chimeric antibody, affinity matured antibody, mutated antibody or any such antibody generated by methodology as known in the art which comprises the variable light chain, the variable heavy chain, or both the variable light chain and variable heavy chain of the 7E7 mAb (as secreted from h7E7), including but not limited to the entire respective variable light or heavy chain, a fragment thereof or a substantially homologous fragment thereof from 7E7, and any such fragment or substantially homologous fragment including but not limited to one, two, three, four, five or all six CDRs (as determined by either the Kabat and/or Chothia methodology, as described herein, as for example each of three CDRs from the variable light chain and/or each of three CDRs from the variable heavy chain) from the variable light chain and/or the variable heavy chain of the monoclonal antibody 7E7. An additional embodiment of the invention relates to a human monoclonal antibody, a humanized antibody, a chimeric antibody, affinity matured antibody, mutated antibody or any such antibody generated by methodology as known in the art which comprises the variable light chain, the variable heavy chain, or both the variable light chain and variable heavy chain of the 6C2 mAb (as secreted from h6C2), including but not limited to the entire respective variable light or heavy chain, a fragment thereof or a substantially homologous fragment thereof from 6C2, and any such fragment or substantially homologous fragment including but not limited to one, two, three, four, five or all six CDRs (as determined by either the Kabat and/or Chothia methodology, as described herein, as for example each of three CDRs from the variable light chain and/or each of three CDRs from the variable heavy chain) from the variable light chain and/or the variable heavy chain of the monoclonal antibody 6C2. Again, any such fragments may include one or a portion of the variable light and heavy chain sequences or CDR regions of 7E7 and/or 6C2, or may be substantially homologous to such sequences. Again, any such antibody may take the form of a human antibody, a humanized antibody, a chimeric antibody, an affinity matured antibody, a mutated antibody, or any such antibody generated by methodology as known in the art.

Also included within the present invention are the isolated nucleic acid molecules encoding the amino acid sequences (or fragments thereof) above, which may include the $V_H$ and/or $V_L$ regions and/or CDRs of the 7E7 and/or 6C2 antibodies. The Variable Light and Heavy Chain DNA sequences for the 7E7 antibody are as follows in Tables 11 and 12, while the Variable Light and Heavy Chain DNA sequences for the 6C2 antibody are as follows in Tables 13 and 14.

TABLE 11

Variable Light Chain DNA Sequences

7E7 GATGTTGTGATGACCCAAACTCCACTCTCCCTGCCTGTCAGTCTTGG
    AGATCAAGCCTCCATCTCTTGCAGATCTGGTCAGAGCCTTGTACACA
    GAAATGGAAACACCTATTTACATTGGTACCTGCAGAAGCCAGGCCA
    GTCTCCAAAGCTCCTGATCTACAAAGTTTCCAACCGATTTTCTGGG
    GTCCCAGACAGGTTCAGTGGCAGTGGAACAGGGACAGATTTTACA
    CTCAAGATCAGCAGAGTGGAGGCTGAGGATCTGGGAGTTTATTTC
    TGCTCTCAAAGTACACATGTTCCATTCACGTTCGGCTCGGGGAC
    AAAGTTGGAAATAAAA (SEQ ID NO: 15)

TABLE 12

Variable Heavy Chain DNA Sequences

7E7 GAGGTGAAGCTGGTGGAGTCTGGAGGAGGCTTGGTACAGCCTGGGA
    GTTCTCAGAGACTCTCCTGTGCAACTTCTGGGTTCACCTTCACTGA
    CTACTACATGAGCTGGGTCCGCCAGCCTCCAGGAAAGGCACTTGA
    GTGGTTGGGTTTTATTAGAAACAAAACTAAACGTTACACAACAGAAT
    ACAGTGCATCTGTGAAGGGTCGGTTCACCATCTCCAGAGATAATT
    CCCAAAGCATCCTCTATCTTCAAATGAACACCCTGAGAGCTGAGG
    ACAGTGCCACTTATTACTGTGCAAGAGATGATCCGTACGCACGGT
    TTGCTTACTGGGGCCAAGGGACTCTGGTCACTGTCTCTGCA
    (SEQ ID NO: 16)

TABLE 13

Variable Light Chain DNA Sequences

6C2 GATGTTGTGATGACCCAGACTCCACTCACTTTGTCGGTTACCATTG
    GACAACCAGCCTCCATCTCTTGCAAGTCAAGTCAGAGCCTCTTA
    GATAGTGATGGAAAGACATATTTGAATTGGTTGTTACAGAGCCAG
    GCCAGTCTCCAAAGCGCCTAATCTTTCTGGTGTCTAAACTGGACT
    CTGGAGTCCCTGACAGGTTCACTGGCAGTGGATCAGGGACAGATT
    TCACACTGAAAATCAGCAGCGTGGAGGCTGAGGATTTGGGAATTT

TABLE 13-continued

Variable Light Chain DNA Sequences

ATTATTGCTGGCAAGGTACACATTTTCCGTGGACGTTCGGTGGAG
GCACCAAGCTGGAAATCAAAC (SEQ ID NO: 44)

TABLE 14

Variable Heavy Chain DNA Sequences

6C2 GAGGTTCAGCTGCAGCAGTCTGGACCTGAACTGGTGAAGCCTGGG
GCTTCAGTGAAGATTTCCTGCAAGGCTTCTGGTTACTCATTTACTG
GCTACTTTTTGAGCTGGGTGAAGCAGAGCCATGGAAGGAGCCTT
GAGTGGATTGGACGTATTAATCCTTACAATGGTCATACTTTCTAC
AACCAGAAGTTCAAGGACAAGGCCACATTGACTGTTGACAAAT
CCTCTACCACAGCCCACATGGAGCTCCTGAGCCTGACATCTG
AGGACTCTGCAGTCTATTATTGTGCAGGATCTGACTCCTGGGG
CCAAGGCACCACTCTCACAGTCTCCTCA (SEQ ID NO: 45)

The DNA sequences for the Variable Light and Heavy Chain CDR sequences of the 7E7 antibody are as follows in Tables 15-17, while DNA sequences for the Variable Light and Heavy Chain CDR sequences of the 7E7 antibody are as follows in Tables 18-20. Tables 15 and 18, respectfully, provide the variable light chain CDR sequences according to both the Chothia and Kabat Method. Table 16 and 19, respectfully, provide the variable heavy chain CDR sequences according to the Chothia Method, defined above. Table 17 and 20 provide the variable heavy chain CDR sequences according to the Kabat Method, defined above.

TABLE 15

Variable Light Chain CDR Sequences - Chothia & Kabat Methods

| CDR1 | CDR2 | CDR3 |
|---|---|---|
| 7E7 AGATCTGGTCAGAGCC TTGTACACAGAAATGG AAACACCTATTTACAT (SEQ ID NO: 17) | AAAGTTTCCAA CCGATTTTCT (SEQ ID NO: 18) | TCTCAAAGTA CACATGTTC CATTCACG (SEQ ID NO: 19) |

TABLE 16

Variable Heavy Chain CDR Sequences - Chothia Method

| CDR1 | CDR2 | CDR3 |
|---|---|---|
| 7E7 GGGTTCACCTTCAC TGACTAC (SEQ ID NO: 20) | AGAAACAAAACTAAAC GTTACACA (SEQ ID NO: 21) | GATGATCCGTACGCA CGGTTTGCTTAC (SEQ ID NO: 22) |

TABLE 17

Variable Heavy Chain CDR Sequences - Kabat Method

| CDR1 | CDR2 | CDR3 |
|---|---|---|
| 7E7 GACTACTACATG AGC (SEQ ID NO: 23) | TTTATTAGAAACAAAAC TAAACGTTACACAACAG AATACAGTGCATCTGTG AAGGGT (SEQ ID NO: 24) | GATGATCCGTACGCA CGGTTTGCTTAC (SEQ ID NO: 22) |

TABLE 18

Variable Light Chain CDR Sequences - Chothia & Kabat Methods

| CDR1 | CDR2 | CDR3 |
|---|---|---|
| 6C2 AAGTCAAGTCAGAGCCT CTTAGATAGTGATGGAAAG ACATATTTGAAT (SEQ ID NO: 35) | CTGGTGTCTAAAC TGGACTCT (SEQ ID NO: 36) | TGGCAAGGTAC ACATTTTCCGTG GACG (SEQ ID NO: 37) |

TABLE 19

Variable Heavy Chain CDR Sequences - Chothia Method

| CDR1 | CDR2 | CDR3 |
|---|---|---|
| 6C2 GGTTACTCATTTAC TGGCTAC (SEQ ID NO: 38) | AATCCTTACAAT GGTCAT (SEQ ID NO: 39) | TCTGACTCT |

TABLE 20

Variable Heavy Chain CDR Sequences - Kabat Method

| CDR1 | CDR2 | CDR3 |
|---|---|---|
| 6C2 GGCTACTTTTTGAG C (SEQ ID NO: 40) | CGTATTAATCCTTACAAT GGTCATACTTTCTAC AACCAGAAGTTCAAG GACAAG (SEQ ID NO: 41) | TCTGACTCT |

The isolated nucleic acid molecule(s) (polynucleotides), encode a biologically relevant portion of 7E7 and/or 6C2, or affinity matured version or otherwise mutated version of 7E7 and/or 6C2 or other anti-Aβ antibodies discussed herein. To this end, the isolated nucleic acid molecules(s) may include one or more of the foregoing DNA sequences, a fragment of one or more of the foregoing sequences, or a nucleic acid sequence that at least 70% homologous, 80% homologous, 90% homologous or 99% homologous to one or more of the foregoing.

Nucleic acids of the present invention may be substantially free from other nucleic acids. For most cloning purposes, DNA is a preferred, but non-limiting, nucleic acid. One or a combination of the foregoing DNA molecules may be subcloned into an expression vector and subsequently transfected into a host cell of choice wherein the recombinant host cell provides a source for substantial levels of a relevant portion of the 7E7 and/or 6C2, or anti-Aβ antibody of the present invention, or the affinity matured version thereof. Such procedures may be used for a variety of utilities, such as generating scFvs or for co-expressing these $V_H$ and $V_L$ chains in a mammalian expression vector system which encodes human $C_H$ and $C_L$ regions, of for example, an IgG antibody.

The degeneracy of the genetic code is such that, for all but two amino acids, more than a single codon encodes a particular amino acid. This allows for the construction of synthetic DNA that encodes an antibody of the present invention where the nucleotide sequence of the synthetic DNA differs significantly from the nucleotide sequences disclosed herein, but still encodes such an antibody. Such synthetic DNAs are intended to be within the scope of the present invention. If it is desired to express such synthetic DNAs in a particular host cell or organism, the codon usage of such synthetic DNAs can be adjusted to reflect the codon usage of that particular host, thus leading to higher levels of expression of the an antibody of the present invention. In other words, this redundancy in the various codons which code for specific amino acids is within the scope of the present invention. Therefore, this invention is also directed to those DNA sequences which encode RNA comprising alternative codons which code for the eventual translation of the identical amino acid, as shown below: A=Ala=Alanine: codons GCA, GCC, GCG, GCU; C=Cys=Cysteine: codons UGC, UGU; D=Asp=Aspartic acid: codons GAC, GAU E=Glu=Glutamic acid: codons GAA, GAG; F=Phe=Phenylalanine: codons UUC, UUU; G=Gly-Glycine: codons GGA, GGC, GGG, GGU; H=His=Histidine: codons CAC, CAU; I=Ile=Isoleucine: codons AUA, AUC; AUU; K=Lys-Lysine: codons AAA, AAG; L=Leu=Leucine: codons UUA, UUG, CUA, CUC, CUG, CUU; M=Met=Methionine: codon AUG; N=Asp=Asparagine: codons GAU, GAC; P=Pro=Proline: codons CCA, CCC, CCG, CCU; Q=Gln=Glutamine: codons CAA, CAG; R=Arg=Arginine: codons AGA, AGG, CGA, CGC, CGG, CGU; S=Ser=Serine: codons AGC, AGU, UCA, UCC, UCG, UCU; T=Thr=Threonine: codons ACA, ACC, ACG, ACU; V=Val=Valine: codons GUA, GUC, GUG, GUU; W=Trp=Tryptophan: codon UGG; Y=Tyr=Tyrosine: codons UAC, UAU. Such recombinant expression vectors may then be stably or transiently transfected into an appropriate cell line for the generation of alternative antibody form.

The present invention notes the existence of codon redundancy which may result in differing DNA molecules expressing an identical antibody or portion thereof (e.g., alternative nucleic acid molecules encoding an identical scFv or a $V_H$ and/or $V_L$ portion of an IgG). For purposes of this specification, a sequence bearing one or more replaced codons will be defined as a degenerate variation. Another source of sequence variation may occur through RNA editing. Such RNA editing may result in another form of codon redundancy, wherein a change in the open reading frame does not result in an altered amino acid residue in the expressed protein. Also included within the scope of this invention are mutations either in the DNA sequence or the translated antibody which improve the ultimate physical properties of the expressed antibody. To this end, the present invention relates to (i) affinity matured versions of anti-Aβ antibodies, including but not limited to 7E7 and/or 6C2, and/or (ii) mutated forms of an anti-Aβ antibody, including but not limited to 7E7 and/or 6C2, including but not limited to one or more mutations in the CDR1, CDR2 and/or CDR3 regions as generated through known affinity maturation methodology and recombinant DNA techniques known for introducing site specific mutation. Such isolated or purified nucleic acid molecules will represent the $V_H$ and/or $V_L$ portions of the anti-Aβ antibody. These nucleic acids are substantially free from other nucleic acids and may be cloned in accordance with the foregoing.

The present invention also relates to recombinant vectors and recombinant hosts, both prokaryotic and eukaryotic, which contain nucleic acid molecules encoding the respective heavy and/or light regions (or fragments thereof) of an anti-Aβ antibody. These nucleic acid molecules, in whole or in part, can be linked with other DNA molecules (i.e, DNA molecules which encompass immunoglobulin genes used for generation of a recombinant human antibody) that are not naturally linked, to form "recombinant DNA molecules" which encode a respective human recombinant antibody. These vectors may be comprised of DNA or RNA. For most cloning purposes DNA vectors are preferred. Typical vectors include plasmids, modified viruses, bacteriophage, cosmids, yeast artificial chromosomes, and other forms of episomal or integrated DNA. It is within the purview of the skilled artisan to determine an appropriate vector for a particular gene transfer, generation of a recombinant human antibody or other use. Methods of subcloning nucleic acid molecules of interest into expression vectors, transforming or transfecting host cells containing the vectors, and methods of making substantially pure protein comprising the steps of introducing the respective expression vector into a host cell, and cultivating the host cell under appropriate conditions are well known. The antibody (such as an IgG recombinant human antibody) so produced may be harvested from the host cells in conventional ways. Any known expression vector may be utilized to practice this portion of the invention, including any vector containing a suitable promoter and other appropriate transcription regulatory elements. The resulting expression construct is transferred into a prokaryotic or eukaryotic host cell to produce recombinant protein. Expression vectors are defined herein as DNA sequences that are required for the transcription of cloned DNA and the translation of their rmRNAs in an appropriate host. Such vectors can be used to express eukaryotic DNA in a variety of hosts such as bacteria, blue green algae, plant cells, insect cells and animal cells. Specifically designed vectors allow the shuttling of DNA between hosts such as bacteria-yeast or bacteria-animal cells. An appropriately constructed expression vector should contain: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one which causes rmRNAs to be initiated at high frequency. Techniques for such manipulations can be found described in Sambrook, et al. (1989, Molecular Cloning. A Laboratory Manual; Cold Spring Harbor Laboratory, Cold Spring Harbor, N.Y.) are well known and available to the artisan of ordinary skill in the art. Expression vectors may include, but are not limited to, cloning vectors, modified cloning vectors, specifically designed plasmids or viruses. Commercially available mammalian expression vectors which may be suitable, include, but are not limited to, pcDNA3.neo (Invitrogen), pcDNA3.1 (Invitrogen), pCI-neo (Promega), pLITMUS28, pLITMUS29, pLITMUS38 and pLITMUS39 (New England Bioloabs), pcDNAI, pcDNA-Ianp (Invitrogen), pcDNA3 (Invitrogen), pMCIneo (Stratagene), pXTI (Stratagene), pSG5 (Stratagene), EBO pSV2-neo (ATCC 37593) pBPV-1(8-2) (ATCC 37110), pdBPV-MMTneo (342-12) (ATCC 37224), pRSVgpt (ATCC 37199), pRSVneo (ATCC 37198), pSV2-dhfr (ATCC 37146), pUCTag (ATCC 37460), and 1ZD35 (ATCC 37565). Also, a variety of bacterial expression vectors are available, including but not limited to pCR2.1 (Invitrogen), pET1 1a (Novagen), lambda gtl 1 (Invitrogen), and pKK223-3 (Pharmacia). In addition, a variety of fungal cell expression vectors may be used, including but not limited to pYES2 (Invitrogen) and *Pichia* expression vector (Invitrogen). Also, a variety of insect cell expression vectors may be used, including but are not limited to pBlueBacIII and pBlueBacHis2 (Invitrogen), and pAcG2T (Pharmingen).

Recombinant host cells may be prokaryotic or eukaryotic, including but not limited to, bacteria such as *E. coli*, fungal cells such as yeast, mammalian cells including, but not limited to, cell lines of bovine, porcine, monkey and rodent origin; and insect cells. Mammalian species which may be suitable, include but are not limited to, L cells L-M(TK-) (ATCC CCL1.3), L cells L-M (ATCC CCL 1.2), Saos-2

(ATCC HTB-85), 293 (ATCC CRL1573), Raji (ATCC CCL 86), CV-1 (ATCC CCL 70), COS-1 (ATCC CRL1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C1271 (ATCC CRL 1616), BS-C-1 (ATCC CCL 26), MRC-5 (ATCC CCL171) and CPAE (ATCC CCL 209).

The antibodies of the present invention may also be adapted or specifically engineered to form variants of the foregoing, including, but not limited to, a polyclonal, alternative monoclonal, chimeric, and/or humanized antibodies. Isolated or variant antibodies of the invention may include single variable domains (sVDs) and antigen binding proteins that comprise sVDs. sVD binding sites can be obtained from antigen specific Fv regions (which comprise both $V_H$ and $V_L$ domains). Often, it can be shown that the binding affinity and specificity of an Fv region is contributed primarily by one of the variable domains. Alternatively, the scFv can be obtained directly. Direct sources of sVDs include mammals (e.g., camelids) that naturally express antibodies containing only $V_H$ domain. Further, phage display libraries can be constructed to express only a single variable domain. For example, a human domain antibody phage display library is commercially available from Domantis (Cambridge, UK).

Chimeric antibodies may generally comprise variable domains of one antibody and constant domains of a different antibody. Typically, to minimize host immune responses against the antibody and to enhance host responses against the antibody target by retaining antibody effector functions, the constant domains of a chimeric antibody are taken from the same species to which the chimeric antibody will be administered.

Humanized antibodies are a form of a chimeric protein that are constructed such that the variable domains include one or more complementarity determining regions (CDRs) of non-human origin that are grafted to human framework regions. The non-human amino acid residues are often referred to as "import" residues, and are typically taken from an "import" variable domain. Humanization can be performed generally following the method of Winter and co-workers (Jones et al., 1986, Nature 321:522-525; Riechmann et al., 1988, Nature, 332:323-327; Verhoeyen et al., 1988, Science 239:1534-1536), by substituting rodent CDRs or CDR sequences for the corresponding sequences of a human antibody. Accordingly, such "humanized" antibodies are chimeric antibodies (see, e.g., U.S. Pat. No. 4,816,567) wherein substantially less than an intact human variable domain has been substituted by the corresponding sequence from a non-human species. In practice, humanized antibodies are typically human antibodies in which some CDR residues and possibly some FR residues are substituted by residues from analogous sites in non-human, for example, rodent antibodies. The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework. (FR) for the humanized antibody (Sims et al., 1987, J. Immunol. 151:2296; Chothia et al., 1987, J. Mol. Biol. 196:901). Another method uses a particular framework derived from the consensus sequence of all human antibodies of a particular subgroup of light or heavy chains. The same framework may be used for several different humanized antibodies (Carter et al., 1992, Proc. Natl. Acad. Sci. USA 89:4285; Presta et al., 1993, J. Immunol. 151:2623). To this end, and in certain embodiments, is may be generated by various means of recombinant DNA technology and non-human transgenics that are well known in the art. Such methodology is utilized to generate an antibody from one of the following origins: (i) a scFv or alternative antibody isolated from a combinatorial human antibody library; (ii) a partial or complete antibody generated from a respective expression vector stably or transiently transfected into a host cell, preferably a mammalian host cell (e.g., subcloning nucleotide sequences encoding $V_H$ and $V_L$ chains into an expression vector in conjunction with respective $C_H$ and $C_L$ nucleotide sequences, so as to promote expression of a predetermined form of antibody showing specificity to Aβ in accordance with the present teachings); and/or (iii) an antibody isolated from a non-human transgenic animal which contains human immunoglobulin genes, or by any other known methodology which relies of the recombinant 'mixing and matching' of human immunoglobulin gene sequences to other DNA sequences in order to generate the human recombinant antibody of interest.

A humanized construct is valuable for elimination of adverse immunogenic characteristics, for example, where an antigen binding domain from a non-human source is desired to be used for treatment in a human. Variable domains have a high degree of structural homology, allowing easy identification of amino acid residues within variable domains which correspond to CDRs and FRs.

Methods have been developed to preserve or to enhance affinity for such variant antibodies, particularly, though not exclusively, the chimeric and/or humanized forms. One way is to include in the recipient variable domain the foreign framework residues which influence the conformation of the CDR regions. A second way is to graft the foreign CDRs onto human variable domains with the closest homology to the foreign variable region. CDRs are most easily grafted onto different framework regions by first amplifying individual FR sequences using overlapping primers which include desired CDR sequences, and joining the resulting gene segments in subsequent amplification reactions. Grafting of a CDR onto a different variable domain can further involve the substitution of amino acid residues which are adjacent to the CDR in the amino acid sequence or packed against the CDR in the folded variable domain structure which affect the conformation of the CDR. Humanized variable domains of the invention therefore include human domains which comprise one or more non-human CDRs as well as such domains in which additional substitutions or replacements have been made to preserve or enhance binding characteristics.

It is of additional import that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e, the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the CDR residues are directly and most substantially involved in influencing antigen binding. Humanization of antibodies is a straightforward protein engineering task. Nearly all murine antibodies can be humanized by CDR grafting, resulting in the retention of antigen binding. See, Lo, Benny, K. C., editor, in Antibody Engineering: Methods and Protocols, volume 248, Humana Press, New Jersey, 2004. To this end, to merely reiterate, additional embodiments of the invention relate to human, humanized, chimeric, affinity matured, mutated, or other forms of anti-Aβ antibodies generated from a 7E7-based mAb or a 6C2-based mAb.

Antibodies of the present invention may also employ variable domains that have been made less immunogenic by replacing surface-exposed residues so as to make the antibody appear as self to the immune system. Antibodies have been modified by this process with no loss of affinity. Because the internal packing of amino acid residues in the vicinity of the antigen binding site remains unchanged, affinity is preserved. Substitution of surface-exposed residues according to the invention for the purpose of reduced immunogenicity does not mean substitution of CDR residues or adjacent residues which influence binding characteristics.

In any of the foregoing embodiments, the variable regions, CDRs, and constant regions incorporated into antibodies can be subject to in vitro or in vivo mutation and screening procedures in order to modify affinity and/or specificity. Thus, binding domains of the invention include those for which binding characteristics have been improved by mutating CDRs and/or FR regions by direct mutation, methods of affinity maturation, or chain shuffling. It is understood that amino acid residues that are primary determinants of binding of single domain antibodies can be within Kabat defined CDRs, but may include other residues as well. For sVDs, residues important for antigen binding can also potentially include amino acids that would otherwise be located at the interface of a $V_H$-$V_L$ heterodimer. Typically, phage display is used to screen such mutants to identify those having the desired binding characteristics (see, e.g., Yang et al., J. Mol. Biol., 254: 392-403 (1995)). Mutations can be made in a variety of ways. One way is to randomize individual residues or combinations of residues so that in a population of otherwise identical sequences, all twenty amino acids or a subset thereof are found at particular positions. Alternatively, mutations may be induced over a range of CDR residues by error prone PCR methods (see, e.g., Hawkins et al., J. Mol. Biol., 226: 889-896 (1992)). For example, phage display vectors containing heavy and light chain variable region genes may be propagated in mutator strains of E. coli (see, e.g., Low et al., J. Mol. Biol., 250: 359-368 (1996)). These methods of mutagenesis are illustrative of the many methods known to one of skill in the art.

Although the invention has been described with reference to certain embodiments, it will be understood by those skilled in the art that various changes may be made and equivalents may be substituted for elements thereof without departing from the scope of the invention. In addition, many modifications may be made to adapt to a particular situation or material to the teachings of the invention without departing from the essential scope thereof. Therefore, it is intended that the invention not be limited to the particular embodiments disclosed, but that the invention will include all embodiments falling within the scope of the appended claims or any claims later added.

In addition to the foregoing, the anti-Aβ antibodies of the present invention may be used alone or within compositions for a wide array uses. In certain aspects, antibodies and compositions containing antibodies of the present invention may be used for diagnosing and/or treating a patient diagnosed with a disease state characterized, at least in part, by Aβ activity, and in certain aspects by amyloidosis or the aggregation of Aβ protein. In further aspects, such antibodies may be used for detection of Aβ expression in a cell (including the isoforms present), screening for and selecting alternative Aβ binding compounds, or the like. The following elaborates on such uses, but is not to be considered limiting to the uses of the anti-Aβ antibodies of the present invention. To this end, one of skill in the art will readily appreciate that the antibodies of the present invention may be provided with any use otherwise known in the art.

Treatment Methods and Pharmaceutical Formulations

In certain aspects, the anti-Aβ antibodies of the present invention may be administered to a subject for treating, preventing, delaying, or otherwise monitoring onset of one or more symptoms associated with Alzheimer's disease, or any other neurodegenerative disease associated with Aβ activity, aggregation, or amyloidosis. Such symptoms can be, but are not limited to, the formation of amyloid plaques in the brain or central nervous system of the subject, particularly amyloid plaques that include one or both Aβ (1-40) and Aβ (1-42). The symptom may also, or alternatively, be an increase in Aβ protein concentration (particularly the 1-40 and/or 1-42 isoforms) in the subject's serum, blood, urine, or cerebrospinal fluid, as compared to a healthy subject not having the neurodegenerative disease. The symptom can also, or alternatively be a neurological symptom, such as, but not limited to, altered taste aversions, altered contextual fear conditioning, memory impairment, loss of motor function, and the like.

Non-limiting examples of such diseases include Alpha1-antitrypsin-deficiency, C1-inhibitor deficiency angioedema, Antithrombin deficiency thromboembolic disease, Kuru, Creutzfeld-Jacob disease/scrapie, Bovine spongiform encephalopathy, Gerstmann-Straussler-Scheinker disease, Fatal familial insomnia, Huntington's disease, Spinocerebellar ataxia, Machado-Joseph atrophy, Dentato-rubro-pallidoluysian atrophy, Frontotemporal dementia, Sickle cell anemia, Unstable hemoglobin inclusion-body hemolysis, Drug-induced inclusion body hemolysis, Parkinson's disease, Systemic AL amyloidosis, Nodular AL amyloidosis, Systemic AA amyloidosis, Prostatic amyloidosis, Hemodialysis amyloidosis, Hereditary (Icelandic) cerebral angiopathy, Huntington's disease, Familial visceral amyloidosis, Familial visceral polyneuropathy, Familial visceral amyloidosis, Senile systemic amyloidosis, Familial amyloid neuropathy, Familial cardiac amyloidosis, Alzheimer's disease, Down syndrome, Medullary carcinoma thyroid and Type 2 diabetes mellitus (T2DM). In a particular embodiment, said disease or disorder is an amyloidosis such as Alzheimer's disease.

The term "treatment," as noted above, refers to both therapeutic and prophylactic measures. Those in need of treatment include those already afflicted with the disease or disorder as well as those in which the disease or disorder is to be prevented. The subject to be treated may have been diagnosed as having the disease or disorder or may be predisposed or susceptible to the disease.

Administration of the anti-Aβ antibodies, or fragments thereof, may be alone or in combination with existing therapeutic regimens for the disease. With Alzheimer's disease, for example, the additional therapeutic regimens can include one or a plurality of agents, small molecules, or biologics otherwise known in the art. Those skilled in the art are readily able to determine standard dosages and scheduling for each of these regimens.

In certain aspects, the dosage regimen will be determined by an attending physician and clinical factors. As is well known in the medical arts, dosages for any one patient depends upon many factors, including the patient's size, body surface area, age, the particular compound to be administered, sex, time and route of administration, general health, and other drugs being administered concurrently. A typical dose can be, for example, in the range of 0.001 to 1000 μg (or of nucleic acid for expression or for inhibition of expression in this range); however, doses below or above this exemplary range are envisioned, especially considering the aforementioned factors. Generally, the dosage can range, e.g., from about 0.0001 to 100 mg/kg, and more usually 0.01 to 5 mg/kg (e.g., 0.02 mg/kg, 0.25 mg/kg, 0.5 mg/kg, 0.75 mg/kg, 1 mg/kg, 2 mg/kg, etc.), of the host body weight. For example dosages can be 1 mg/kg body weight or 10 mg/kg body weight or within the range of 1-10 mg/kg, or at least 1 mg/kg. Doses intermediate in the above ranges are also intended to be within the scope of the invention. Subjects can be administered such doses daily, on alternative days, weekly or according to any other schedule determined by empirical analysis. An exemplary treatment entails administration in multiple dosages over a prolonged period, for example, of at least six months. Additional exemplary treatment regimens entail administration once per every two weeks or once a month or once every 3 to 6 months. Exemplary dosage schedules include 1-10 mg/kg or 15 mg/kg on consecutive days, 30 mg/kg on alternate days or 60 mg/kg weekly. In some methods, two or more antibodies with different binding specificities are administered simultaneously, in which case the dosage of each antibody administered falls within the ranges indicated. Progress can be monitored by periodic assessment. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives can also be present such as, for example, antimicrobials, anti-oxidants, chelating agents, and inert gases and the like. Furthermore, the pharmaceutical composition of the invention can comprise further agents such as dopamine or psychopharmacologic drugs, depending on the intended use of the pharmaceutical composition.

In conjunction with one or more of the foregoing treatment regimes, a pharmaceutical composition comprising an effective amount one more of the anti-Aβ antibodies of the present invention, or an affinity matured version thereof, may be administered to provide a prophylactic or therapeutic treatment by inhibiting Aβ activity or, in particular, Aβ aggregation or amyloidosis. The antibody-based pharmaceutical composition of the present invention may be formulated by any number of strategies known in the art (e.g., see McGoff and Scher, 2000, *Solution Formulation of Proteins/Peptides*: In McNally, E. J., ed. *Protein Formulation and Delivery*. New York, N.Y.: Marcel Dekker; pp. 139-158; Akers and Defilippis, 2000, *Peptides and Proteins as Parenteral Solutions*. In: *Pharmaceutical Formulation Development of Peptides and Proteins*. Philadelphia, Pa.: Talyor and Francis; pp. 145-177; Akers, et al., 2002, *Pharm. Biotechnol.* 14:47-127). A pharmaceutically acceptable composition suitable for patient administration will contain an effective amount of the antibody in a formulation which both retains biological activity while also promoting maximal stability during storage within an acceptable temperature range. The pharmaceutical compositions can also include, depending on the formulation desired, pharmaceutically acceptable diluents, pharmaceutically acceptable carriers and/or pharmaceutically acceptable excipients, or any such vehicle commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution or the like. The amount of an excipient that is useful in the pharmaceutical composition or formulation of this invention is an amount that serves to uniformly distribute the antibody throughout the composition so that it can be uniformly dispersed when it is to be delivered to a subject in need thereof. It may serve to dilute the antibody to a concentration which provides the desired beneficial palliative or curative results while at the same time minimizing any adverse side effects that might occur from too high a concentration. It may also have a preservative effect. Thus, for the antibody having a high physiological activity, more of the excipient will be employed. On the other hand, for any active ingredient(s) that exhibit a lower physiological activity, a lesser quantity of the excipient will be employed. In general, the amount of excipient in the composition will be between about 50% weight (w) and 99.9% wt of the total composition. If the antibody exhibits a particularly low physiological activity, the amount of excipient could be as little as 1% wt. On the other hand, for an antibody that has a particularly high physiological activity, the amount of excipient may be between about 98.0% and about 99.9% wt. In addition, the antibody or antibodies may be administered in the form of a "chemical derivative" (a molecule that contains additional chemical moieties which are not normally a part of the base molecule). Such moieties may improve the solubility, half-life, absorption, etc. of the biological agent. Alternatively, these moieties may attenuate undesirable side effects of the antibody.

Pharmaceutical compositions can also include large, slowly metabolized macromolecules such as proteins, polysaccharides, polylactic acids, polyglycolic acids and copolymers (such as latex functionalized sepharose, agarose, cellulose, and the like), polymeric amino acids, amino acid copolymers, and lipid aggregates (such as oil droplets or liposomes). Additionally, these carriers can function as immunostimulating agents (i.e., adjuvants). For parenteral administration, agents of the invention can be administered as injectable dosages of a solution or suspension of the substance in a physiologically acceptable diluent with a pharmaceutical or physiologically acceptable carrier which can be a sterile liquid such as water oils, saline, glycerol, or ethanol. Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions.

The antibody formulation may be in liquid form or solid form. A solid formulation is generally lyophilized and brought into solution prior to administration for either single or multiple dosing. The formulations should not be exposed to extreme temperature or pH so as to avoid thermal denaturation. Thus, it is essential to formulate an antibody composition of the present invention within a biologically relevant pH range. A solution buffered to maintain a proper pH range during storage is indicated, especially for liquid formulations stored for longer periods of time between formulation and administration. To date, both liquid and solid formulations require storage at lower temperatures (usually 2-8° C.) in order to retain stability for longer periods. Formulated antibody compositions, especially liquid formulations, may contain a bacteriostat to prevent or minimize proteolysis during storage, including but not limited to effective concentrations (usually <1% w/v) of benzyl alcohol, phenol, m-cresol, chlorobutanol, methylparaben, and/or propylparaben. A bacteriostat may be contraindicated for some patients. Therefore, a lyophilized formulation may be reconstituted in a solution either containing or not containing such a component. Additional components may be added to either a buffered liquid or solid antibody formulation, including but not limited to sugars as a cryoprotectant (including but not necessarily limited to polyhydroxy hydrocarbons such as sorbitol, mannitol, glycerol and dulcitol and/or disaccharides such as sucrose, lactose, maltose or trehalose) and, in some instances, a relevant salt (including but not limited to NaCl, KCl or LiCl). Such antibody formulations, especially liquid formulations slated for long term storage, will rely on a useful range of total osmolarity to both promote long term stability at temperature of 2-8° C., or higher, while also making the formulation useful for parenteral injection. An effective range of total osmolarity (the total number of molecules in solution) is from about 200 mOs/L to about 800 mOs/L. It will be apparent that the amount of a cyroprotectant, such as sucrose or sorbitol, will depend upon the amount of salt in the formulation in order for the total osmolarity of the solution to remain within an appropriate range. Therefore a salt free formulation may contain from about 5% to about 25% sucrose, with a preferred range of sucrose from about 7% to about 15%, with an especially preferred sucrose concentration in a salt free formulation being from 10% to 12%. Alternatively, a salt free sorbitol-based formulation may contain sorbitol within a range from about 3% to about 12%, with a preferred range from about 4% to 7%, and an especially preferred range is from about 5% to about 6% sorbitol in a salt-free formulation. Salt-free formulations will of course warrant increased ranges of the respective cryoprotectant in order to maintain effective osmolarity levels. These formulation may also contain a divalent cation (including but not necessarily limited to $MgCl_2$, $CaCl_2$ and $MnCl_2$); and a non-32 ionic surfactant (including but not necessarily limited to Polysorbate-80 (Tween 80®), Polysorbate-60 (Tween 60®), Polysorbate-40 (Tween 40®) and Polysorbate-20 (Tween 20®), polyoxyethylene alkyl ethers, including but not limited to Brij 58®, Brij 35®, as well as others such as Triton X-100®, Triton X 114®, NP40®, Span 85 and the Pluronic series of non-ionic surfactants (e.g., Pluronic 121)). Any combination of such components, including probable inclusion of a bacteriostat, may be useful to fill the antibody-containing formulations of the present invention.

Numerous examples of various other carriers, diluents, excipients and the such are known in the art and are disclosed in references cited herein, as well as *Remington's Pharmaceutical Sciences* (18th ed.; Mack Publishing Company, Easton, Pa., 1990), the contents of which are incorporated herein by reference. Briefly, it will be appreciated that suitable carriers, excipients, and other agents may be incorporated to formulate the pharmaceutical compositions to provide improved transfer, delivery, tolerance, and the like. The methods of incorporating the biological agent and/or additional active ingredient(s) into the carrier are known to a person of ordinary skill in the art and depend on the nature of the biological agent and the nature of the carrier selected by a person practicing the current invention. Ionic binding, gel encapsulation or physical trapping inside the carrier, iontophoresis and soaking the carrier in a solution of the biological agent are suitable examples contemplated in formulating a pharmaceutical composition to be used to practice of the disclosed treatment methods. Alternatively, the carrier may be little more than a diluent for the biological agent. These formulations may include for example, powders, pastes, ointments, jelly, waxes, oils, lipids, anhydrous absorption bases, oil-in-water or water-in-oil emulsions, emulsions carbowax (polyethylene glycols of a variety of molecular weights), semi-solid gels, and semi-solid mixtures containing carbowax. The dosage regimen utilizing the compounds of the present invention is selected in accordance with a variety of factors including type, species, age, weight, sex and medical condition of the patient; the severity of the condition to be treated; the route of administration; the renal, hepatic and cardiovascular function of the patient; and the particular biological agent thereof employed. A physician or veterinarian of ordinary skill can readily determine and prescribe the effective amount of the drug required to prevent, counter or arrest the progress of the condition. Optimal precision in achieving concentrations of drug within the range that yields efficacy without toxicity requires a regimen based on the kinetics of the drug's availability to target sites. This involves a consideration of the distribution, equilibrium, and elimination of a drug. Any of the foregoing formulations may be appropriate in treatments and therapies in accordance with the present invention, provided that the active ingredient in the formulation is not inactivated by the formulation and the formulation is physiologically compatible.

The pharmaceutical compositions of the present invention may be administered to the host in any manner, strategy and/or combination available in the art in amounts sufficient to offer a therapeutic treatment by inhibiting, delaying, treating or reducing, Aβ protein activity, aggregation, use in the formation of associated plaques, and/or amyloidosis. These compositions may be provided to the individual by a variety of routes known in the art, especially parenteral routes, including but in no way limited to parenteral routes such as intravenous (IV), intramuscular (IM); or subcutaneous (SC) administration, with IV administration being the norm within the art of therapeutic antibody administration. These compositions may be administered as separate or multiple doses (i.e, administration of the antibody at staggered times by maintaining the sterile condition of the formulation through the treatment regime). The dosage regimen utilizing the compounds of the present invention is selected in accordance with a variety of factors including type, species, age, weight, sex and medical condition of the patient (such as a human patient); the severity of the condition to be treated; the route of administration; the renal, hepatic and cardiovascular function of the patient; and the particular antibody thereof employed. A physician or veterinarian of ordinary skill can readily determine and prescribe the effective therapeutic amount of the antibody. Optimal precision in achieving concentrations of antibody within the range that yields efficacy without toxicity requires a regimen based on the kinetics of the drug's availability to target sites. This involves a consideration of the distribution, equilibrium, and elimination of a drug. Antibodies described herein may be used alone at appropriate dosages. Alternatively, co-administration or sequential administration of other agents may be desirable. It will be possible to present a therapeutic dosing regimen for the antibodies of the present invention in conjunction with administration of alternative prophylactic or therapeutic regimes. An effective dosage regime will vary depending upon many different factors, including means of administration, target site, physiological state of the patient, whether the patient is human or an animal, other medications administered, and whether treatment is prophylactic or therapeutic. For administration of an anti-Aβ antibody, the dosage ranges from about 0.0001 to 100 mg/kg, and more usually 0.01 to 5 mg/kg of the host body weight.

Another aspect regarding delivery and dosage regimes for an anti-Aβ antibody composition of the present invention relates to drug delivery via parenteral routes, which may include non-injectable and injectable devices. Typically, injectable compositions are prepared as either liquid solutions or suspensions; solid forms suitable for solution in, or suspension in, liquid vehicles prior to injection can also be prepared. The preparation also can be emulsified or encapsulated in liposomes or microparticles such as polylactide, polyglycolide, or copolymer for enhanced adjuvant effect, as discussed above (see Langer, 1990, *Science* 249: 1527-1523; and Hanes, 1997, *Advanced Drug Delivery Reviews* 28: 97-119). The agents of this invention can be administered in the form of a depot injection or implant preparation which can be formulated in such a manner as to permit a sustained or pulsatile release of the active ingredient.

Vaccine

In certain embodiments, the foregoing pharmaceutical composition(s) can be formulated as a vaccine, for example, if the pharmaceutical composition of the invention includes an anti-Aβ antibody or binding fragment, derivative or variant thereof for passive immunization. To this end, the present anti-Aβ antibodies and their equivalents will be particularly useful as a vaccine for the prevention or amelioration of neurodegenerative disease states, or any diseases, associated with Aβ activity, aggregation, the formation of amyloid plaques, and/or amyloidosis, particularly those discussed herein, and in certain preferred embodiments Alzheimer's disease.

Aβ Detection/Diagnosis Assays

The anti-Aβ antibodies described herein may be used as the basic reagents in a number of different immunoassays to determine the presence of a Aβ isoform in a tissue sample. Generally speaking, the antibodies can be employed in any type of immunoassay, whether qualitative or quantitative. This includes both the two-site sandwich assay and the single site immunoassay of the non-competitive type, as well as in traditional competitive binding assays. One embodiment of interest, for ease of detection, and its quantitative nature, is the sandwich or double antibody assay, of which a number of variations exist, all of which are intended to be encompassed by this portion of the present invention. For example, in a typical forward sandwich assay, unlabeled antibody (e.g. a first anti-Aβ antibody) is immobilized on a solid substrate, e.g., microtiter plate wells, and the sample to be tested is brought into contact with the bound molecule. After a suitable period of incubation, for a period of time sufficient to allow formation of an antibody-antigen binary complex, a second antibody (e.g. a second anti-Aβ antibody with a different target epitope than the first), labeled with a reporter molecule capable of inducing a detectable signal, is then added and incubation is continued allowing sufficient time for binding with the antigen at a different site and the formation of a ternary complex of antibody-antigen-labeled antibody. Any unreacted material is washed away, and the presence of the antigen is determined by observation of a signal, which may be quantitated by comparison with a control sample containing known amounts of antigen. Variations on the forward sandwich assay include the simultaneous assay, in which both sample and antibody are added simultaneously to the bound antibody, or a reverse sandwich assay in which the labeled antibody and sample to be tested are first combined, incubated and added to the unlabeled surface bound antibody. These techniques are well known to those skilled in the art, and the possibility of minor variations will be readily apparent. As used herein, "sandwich assay" is intended to encompass all variations on the basic two-site technique.

For the sandwich assays of the present invention, the only limiting factor is that both antibodies have different binding specificities for the Aβ protein. Thus, a number of possible combinations are possible. As a more specific example, in a typical forward sandwich assay, a primary antibody is either covalently or passively bound to a solid support. The solid surface is usually glass or a polymer, the most commonly used polymers being cellulose, polyacrylamide, nylon, polystyrene, polyvinylchloride or polypropylene. The solid supports may be in the form of tubes, beads, discs or microplates, or any other surfaces suitable for conducting an immunoassay. The binding processes are well known in the art. Following binding, the solid phase-antibody complex is washed in preparation for the test sample. An aliquot of the body fluid to be tested is then added to the solid phase complex and incubated at 25° C. for a period of time sufficient to allow binding of any Aβ protein present to the antibody. The second antibody is then added to the solid phase complex and incubated at 25° C. for an additional period of time sufficient to allow the second antibody to bind to the primary antibody-antigen solid phase complex. The second antibody is linked to a reporter molecule, the visible signal of which is used to indicate the binding of the second antibody to any antigen in the sample. By "reporter molecule," as used in the present specification is meant a molecule which by its chemical nature, provides an analytically detectable signal which allows the detection of antigen-bound antibody. Detection must be at least relatively quantifiable, to allow determination of the amount of antigen in the sample, this may be calculated in absolute terms, or may be done in comparison with a standard (or series of standards) containing a known normal level of antigen.

The most commonly used reporter molecules in this type of assay are either enzymes or fluorophores. In the case of an enzyme immunoassay an enzyme is conjugated to the second antibody, often by means of glutaraldehyde or periodate. As will be readily recognized, however, a wide variety of different conjugation techniques exist, which are well known to the skilled artisan. Commonly used enzymes include horseradish peroxidase, glucose oxidase, beta-galactosidase and alkaline phosphatase, among others. The substrates to be used with the specific enzymes are generally chosen for the production, upon hydrolysis by the corresponding enzyme, of a detectable color change. For example, p-nitrophenyl phosphate is suitable for use with alkaline phosphatase conjugates; for peroxidase conjugates, 1,2-phenylenediamine or toluidine are commonly used. It is also possible to employ fluorogenic substrates, which yield a fluorescent product rather than the chromogenic substrates noted above. In all cases, the enzyme-labeled antibody is added to the first antibody-Aβ protein complex and allowed to bind to the complex, and then the excess reagent is washed away. A solution containing the appropriate substrate is then added to the tertiary complex of antibody-antigen-labeled antibody. The substrate reacts with the enzyme linked to the second antibody, giving a qualitative visual signal, which may be further quantitated, usually spectrophotometrically, to give an evaluation of the amount of antigen that is present in the serum sample.

Additionally, fluorescent compounds, such as fluorescein or rhodamine, may be chemically coupled to antibodies without altering their binding capacity. When activated by illumination with light of a particular wavelength, the fluorochrome-labeled antibody absorbs the light energy, inducing a state of excitability in the molecule, followed by emission of the light at a characteristic longer wavelength. The emission appears as a characteristic color visually detectable with a light microscope. As in the enzyme immunoassay (EIA), the fluorescent-labeled antibody is allowed to bind to the first antibody-Aβ protein complex. After washing the unbound reagent, the remaining ternary complex is then exposed to light of the appropriate wavelength, and the fluorescence observed indicates the presence of the antigen. Immunofluorescence and EIA techniques are both very well established in the art and are particularly preferred for the present method. However, other reporter molecules, such as radioisotopes, chemiluminescent or bioluminescent molecules may also be employed. It will be readily apparent to the skilled artisan how to vary the procedure to suit the required use.

In another embodiment, the sample to be tested may be used in a single site immunoassay wherein it is adhered to a solid substrate either covalently or noncovalently. An unlabeled anti-Aβ antibody of the present invention is brought into contact with the sample bound on the solid substrate. After a suitable period of incubation, for a period of time sufficient to allow formation of an antibody-antigen binary complex a second antibody, labeled with a reporter molecule capable of inducing a detectable signal, is then added and incubation is continued allowing sufficient time for the formation of a ternary complex of antigen-antibody-labeled antibody. For the single site immunoassay, the second antibody may be a general antibody (i.e, zenogeneic antibody to immunoglobulin, particularly anti-(IgM and IgG) linked to a reporter molecule) that is capable of binding an antibody that is specific for Aβ.

In accordance with the foregoing, the anti-Aβ antibodies of the present invention can be used in a method for the diagnosis of a disorder in an individual by obtaining a body fluid sample from the tested individual which can be a blood sample, a lymph sample or any other body fluid sample and contacting the body fluid sample with an antibody of the instant invention under conditions enabling the formation of antibody-antigen complexes. The level of such complexes is then determined by methods known in the art, a level significantly higher than that formed in a control sample indicating the disease in the tested individual. In the same manner, the specific antigen bound by the antibodies of the invention can also be used. Thus, the present invention relates to an in vitro immunoassay comprising the binding molecule, e.g., antibody or antigen-binding fragment thereof of the invention.

In this context, the present invention also relates to means specifically designed for this purpose. For example, an antibody-based array can be used, which is for example loaded with anti-Aβ antibodies of the present invention which specifically recognize Aβ, in particular monomeric and/or oligomeric forms of either or both the 1-40 and 1-42 isoforms. Design of microarray immunoassays is summarized in Kusnezow et al, 2006, Mol. Cell Proteomics 5: 1681-1696. Accordingly, the present invention also relates to microarrays loaded with Aβ binding molecules identified in accordance with the present invention.

In one embodiment, the present invention relates to a method of diagnosing a neurodegenerative disease or amyloidosis in a subject, the method comprising determining the presence of Aβ (particularly monomeric and/or oligomeric forms of either or both the 1-40 and 1-42 isoforms) and/or pathologically modified and/or aggregated Aβ in a sample from the subject to be diagnosed with at least one antibody of the present invention, an Aβ binding fragment thereof or an Aβ-binding molecule having substantially the same binding specificities of any one thereof, wherein the presence of pathologically modified and/or aggregated Aβ is indicative of a neurodegenerative disease or amyloidosis and an increase of the level of the pathologically modified and/or aggregated Aβ in comparison to the level of the physiological Aβ forms is indicative for progression of a neurodegenerative disease or amyloidosis in said subject.

The subject to be diagnosed can be asymptomatic or preclinical for the disease. In one embodiment, the control subject has a neurodegenerative disease or amyloidosis, or similar disease state characterized by Aβ activity or aggregation, as mentioned above, wherein a similarity between the level of pathologically modified and/or aggregated Aβ and the reference standard indicates that the subject to be diagnosed has such a disease. Alternatively, or in addition as a second control the control subject does not have such a disease, wherein a difference between the level Aβ and/or of pathologically modified and/or aggregated Aβ and the reference standard indicates that the subject to be diagnosed has the disease. In one embodiment, the subject to be diagnosed and the control subject(s) are age-matched. The sample to be analyzed can be any body fluid suspected to contain pathologically modified and/or aggregated Aβ, for example a blood, CSF, or urine sample.

The level Aβ and/or of pathologically modified and/or aggregated Aβ can be assessed by any suitable method known in the art comprising, e.g., analyzing Aβ by one or more techniques chosen from Western blot, immunoprecipitation, enzyme-linked immunosorbent assay (ELISA), radioimmunoassay (RIA), fluorescent activated cell sorting (FACS), two-dimensional gel electrophoresis, mass spectroscopy (MS), matrix-assisted laser desorption/ionization-time of flight-MS (MALDI-TOF), surface-enhanced laser desorption ionization-time of flight (SELDI-TOF), high performance liquid chromatography (HPLC), fast protein liquid chromatography (FPLC), multidimensional liquid chromatography (LC) followed by tandem mass spectrometry (MS/MS), and laser densitometry. In one embodiment, said in vivo imaging of Aβ comprises positron emission tomography (PET), single photon emission tomography (SPECT), near infrared (NIR) optical imaging or magnetic resonance imaging (MRJ).

In further embodiments, the anti-Aβ antibodies of the present invention may be used to study the aggregation of Aβ proteins or pathogenic modification of such proteins and its role in the progression of one or more neurodegenerative diseases, including Alzheimer's disease. In certain non-limiting embodiments, the differential binding of such antibodies, can be used to study and differentiate which Aβ isoforms are involved in the formation of amyloid beta deposits or plaques and what roles each isoforms plays in the formation of these structures. Methods associated with such use include those discussed herein, and otherwise know in the art.

In conjunction with such embodiments, the present invention also includes a kit for detecting Aβ protein (particularly monomeric and/or oligomeric forms of the 1-40 and/or 1-42 isoforms) that includes (1) an antibody or a fragment thereof, capable of specifically binding in vitro to an epitope of a Aβ protein; and, (2) a reagent that binds, directly, or indirectly, to said antibody or the fragment thereof. Such a kit provides a pharmaceutical or diagnosticising one or more containers filled with one or more of the above described ingredients, e.g. anti-Aβ antibody, binding fragment, derivative or variant thereof, polynucleotide, vector or cell of the present invention. Associated with such container(s) can be a notice in the form prescribed by a governmental agency regulating the manufacture, use or sale of pharmaceuticals or biological products, which notice reflects approval by the agency of manufacture, use or sale for human administration. In addition or alternatively the kit comprises reagents and/or instructions for use in appropriate diagnostic assays. The composition, e.g. kit of the present invention is of course particularly suitable for the risk assessment, diagnosis, prevention and treatment of a disorder which is accompanied with the presence of Aβp, and in particular applicable for the treatment of one or more of the disease states provided herein that are characterized by Aβ activity, aggregation, or amyloidosis.

Drug Screening Assay

In further embodiments, the anti-Aβ antibodies of the present invention may be used in methods of screening for and selecting compounds which may act as an inhibitor of Aβ activity in a cell or otherwise may be used to prevent, reduce, treat, or otherwise monitor the presence of Aβ protein aggregation or amyloidosis. Such methodology comprises utilizing an antibody with anti-Aβ affinity in various antibody/peptide/test compound interaction assays in order to select a compound which modulates Aβ activity/aggregation or amyloidosis. The compound may be a non-proteinaceous organic or inorganic molecule, a peptide (e.g., as a potential prophylactic or therapeutic peptide vaccine), a protein, DNA (single or double stranded) or RNA (such as siRNA or shRNA). It will become evident upon review of the disclosure and teachings of this specification that any such peptide or small molecule which effectively competes with an anti-Aβ antibody of the present invention for binding to the epitope of the Aβ, represents a possible lead compound relating to prophylactic or therapeutic treatment of a disease state characterized by Aβ expression, overexpression, or aggregation, particularly amyloidosis. To this end, interaction assays may be utilized for the purpose of high throughput screening to identify compounds that occupy or interact with the Aβ epitopes and displace the antibody.

Various antibody/antigen-based assays known in the art may be used in accordance with the foregoing, including, but not limited to, an ELISA assay, a radioimmune assay, a Western blot analysis, any homogenous assay relying on a detectable biological interaction not requiring separation or wash steps (e.g., see AlphaScreen from PerkinElmer) and/or SPR-based technology (e.g., see BIACore)). Compounds and/or peptide vaccine candidates identified through use of an anti-Aβ antibody may be detected by a variety of assays. The assay may be a simple "yes/no" assay to determine whether there is a change in the ability to form the known antibody/antigen complex, or may be made quantitative in nature by utilizing an assay such as an ELISA based assay, a homogenous assay, or an SPR-based assay. To this end, the present invention relates to any such assay, regardless of the known methodology employed, which measures the ability of a test compound to compete with an anti-Aβ antibody of the present invention.

The following are examples supporting the foregoing invention. They are not to be construed as limiting to the invention.

EXAMPLES

Example 1—Generation of Anti-Amyloid Beta mAbs

For each of Aβ 1-38, Aβ 1-40, and Aβ 1-42, rubredoxin-β-amyloid fusion protein expressing E. Coli cells were generated in accordance with the procedures disclosed in PCT International Application Publication No. WO 2000/39310, the contents of which are incorporated by reference herein. Five grams (5 g) of the rub-Aβ expressing cells were isolated and combined with 150 mL of Cell Lysis Buffer (10 mM Tris pH 7.4) in a 250 mL plastic beaker and stirred until all of the cells were in solution. A Fisher Scientific Cell Dismembrator was used to perform cell lysis. The sonicator was set to 80% power and the cells were sonicated 7 times for 30 seconds with 1 minute breaks in between each sonication. After cell lysis, 2.0M imidazole was added to give a final concentration of 5.0 mM in the sample. Sodium chloride (NaCl) powder was then added to give a final concentration of 0.5M in the sample.

The resulting solution was then split equally between four 50 mL Beckman centrifuge bottles. The bottles were then centrifuged to speed of 12,000 rpm, temperature of 8-12° C., at a time of 15 minutes. The supernatant from the four bottles were then pooled together in a 250 mL beaker.

The contents of the supernatant were then separated using a 5 mL Nickel Affinity Column and the elution was dialyzed and separated in a Sepharose Column. The rubredoxin-beta amyloid protein was then isolated and concentrated.

For the generation of the mAbs, 1.0 mg vials of lyophilized rub-Aβ 1-38, 1-40, and 1-42 (referred to, generally, herein as beta-amyloid or Aβ) were hydrated in 1.0 mL of 1.0% $NH_4OH$ and sonicated until the solutions were clear. Twenty (20) μL of each solution was diluted separately into 10 mL of TBS pH0.0 and gently inverted several times to mix. To create the experimental conditions of 100 ng target antigen, 50 μL of the diluted beta-amyloid was added to the wells of a 96-well Nunc MaxiSorp plate. This amount of antigen was added in triplicate (50 μL was added to three separate wells for each antibody being tested in each assay). Quantities of target antigen were tested to a maximum of 250 ng, and to a minimum of ten nanograms. Each antigen was prepared in a way that required the addition of exactly 50 μL of antigen mixture to each well, so each target quantity was mixed separately. Three wells per antibody being tested were left empty at this stage of the assay and later serve as negative controls to ensure positive signals were not the result of non-specific binding. Once all experimental wells had received antigen solution the plates were wrapped in foil and placed at 2-8° C. for 15 hours.

After 15 hours the wells of the plates were washed three times with TBST (TBS with 0.1% Tween 20) pH 7.4. Following the third wash, the wells (including those left empty in the first step) were filled with 250 µL TBS with 3% BSA Fraction V (Fisher#BP1605-100). The plate was then incubated at 37° C. for 1 hour. After one hour the wells were emptied and rinsed three times with 250 µL TBST.

The solution for primary antibody dilution was made in 100 mL amounts of the same buffer used to wash out the wells, which was TBST, but 1.0 gram of BSA Fraction V was also dissolved for a final concentration of 1% BSA. 10 mL of this solution was placed into seven separate 50 mL Falcon tubes, and each antibody was then separately added for a final concentration of 0.45 µg/mL. That concentration, 0.45 µg/mL, was the equivalent of a 1:1000 dilution, which was the antibody with the highest initial concentration of all that were screened.

50 µL of the antibody mixture was added to each well, and the plates were incubated at 37° C. for one hour. During this time a 1:5,000 secondary antibody mixture was made. This consisted of 10 mL TBST with 1% BSA, and 2 µL of Goat Anti-Mouse IgG (H+L) HRP Conjugate (BioRad#170-6516). After one hour the plates were washed three times with TBST, and then 50 µL of secondary antibody solution was added to each well. This was allowed to incubate at room temperature for one hour, and then the wells were washed a total of five times with TBST. Finally 100 µL of 1-Step TMB Substrate (Thermo Scientific #34028) was added to each well and allowed to incubate at room temperature for five minutes followed by the addition of 100 µL 2M Sulfuric Acid. Optical density (OD) readings were then taken at 450 nm (see, e.g., FIGS. 1-19, 21, 23, 25). FIGS. 1-8 provide the initial ELISA screen results of the mAbs tested.

Figure 1:
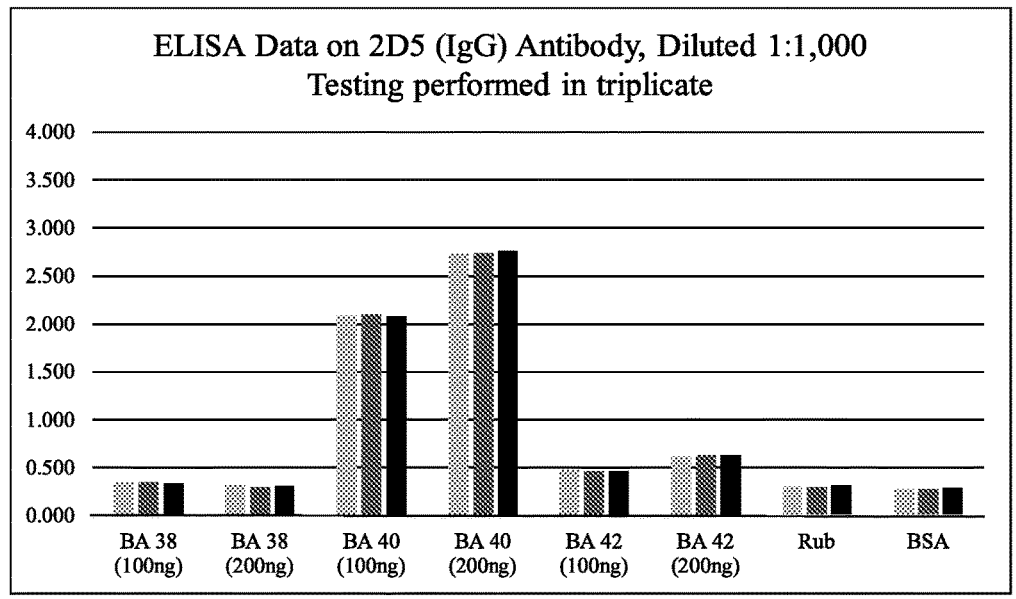
FIG. 1 provides a graphic illustration of the ELISA data for mAb 2D5 on rub-Aβ 1-38, rub-Aβ 1-40, and rub-Aβ 1-42. Testing was performed (and results provided) in triplicate for each dilution. (y-axis=$OD_{450\ nm}$).
Figure 2:
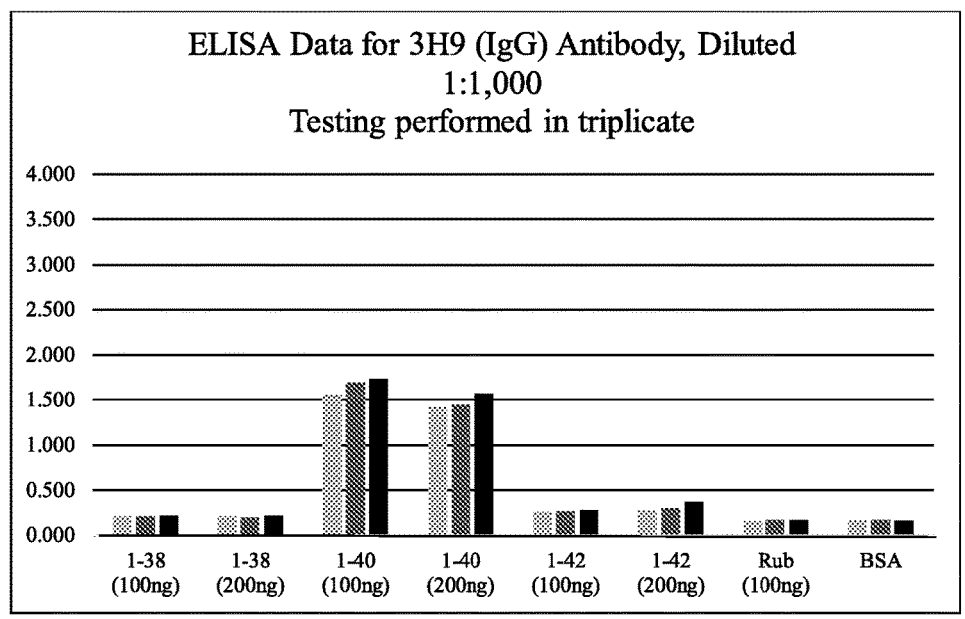
FIG. 2 provides a graphic illustration of the ELISA data for mAb 3H9 on rub-Aβ 1-38, rub-Aβ 1-40, and rub-Aβ 1-42. Testing was performed (and results provided) in triplicate for each dilution. (y-axis=$OD_{450\ nm}$).
Figure 3:
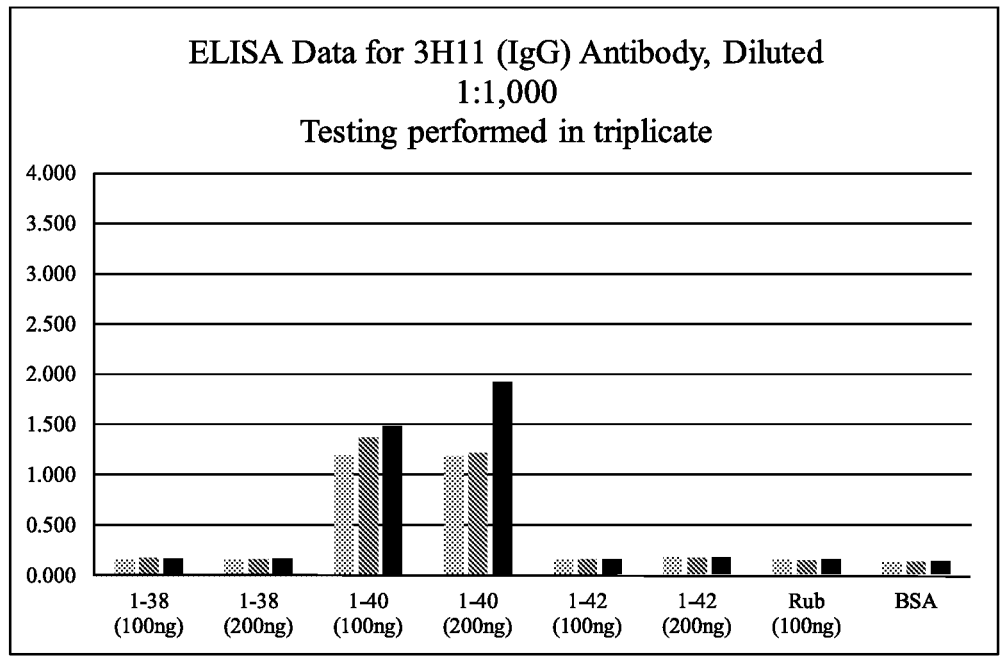
FIG. 3 provides a graphic illustration of the ELISA data for mAb 3H11 on rub-Aβ 1-38, rub-Aβ 1-40, and rub-Aβ 1-42. Testing was performed (and results provided) in triplicate for each dilution. (y-axis=$OD_{450\ nm}$).
Figure 4:
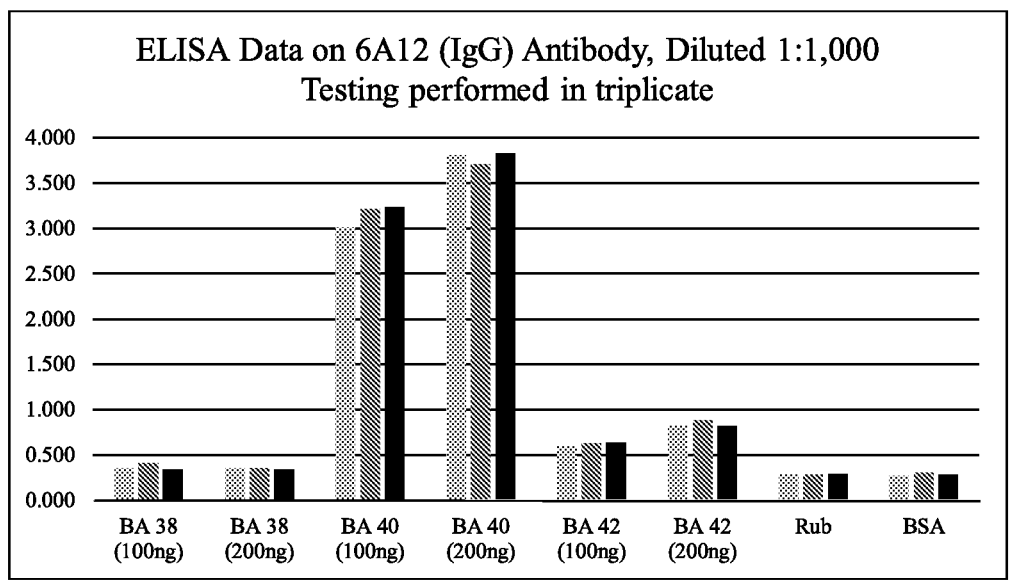
FIG. 4 provides a graphic illustration of the ELISA data for mAb 6A12 on rub-Aβ 1-38, rub-Aβ 1-40, and rub-Aβ 1-42. Testing was performed (and results provided) in triplicate for each dilution. (y-axis=$OD_{450\ nm}$).
Figure 5:
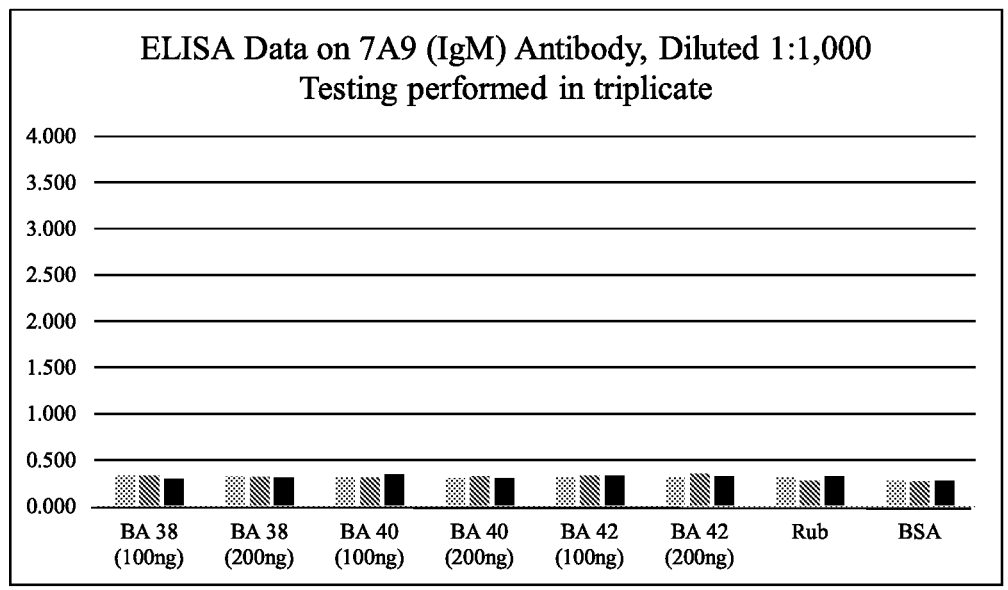
FIG. 5 provides a graphic illustration of the ELISA data for mAb 7A9 on rub-Aβ 1-38, rub-Aβ 1-40, and rub-Aβ 1-42. Testing was performed (and results provided) in triplicate for each dilution. (y-axis=$OD_{450\ nm}$).
Figure 6:
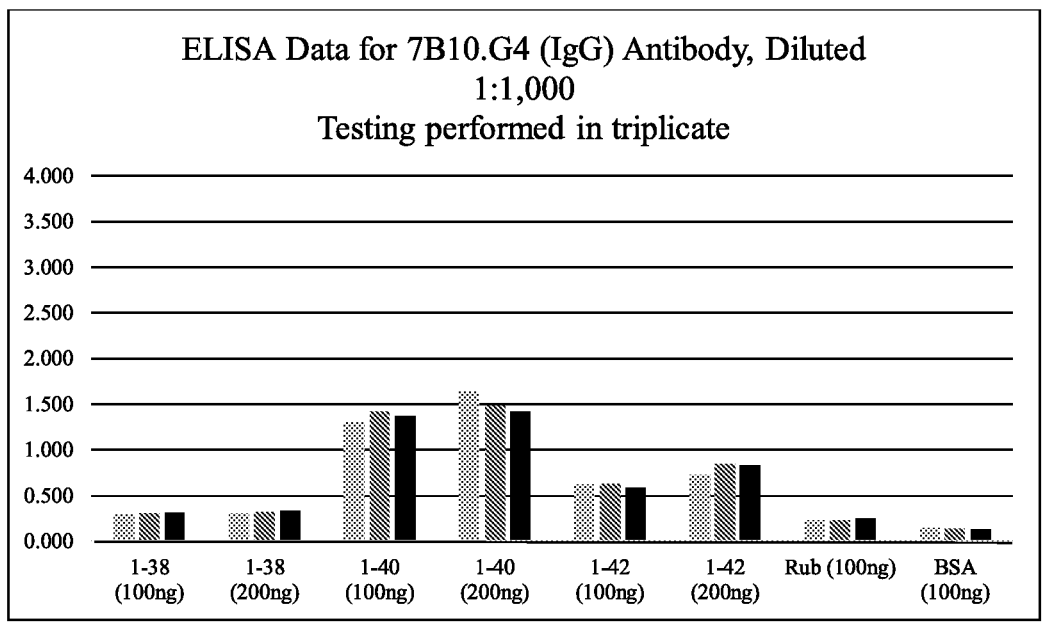
FIG. 6 provides a graphic illustration of the ELISA data for mAb 7B10.G4 on rub-Aβ 1-38, rub-Aβ 1-40, and rub-Aβ 1-42. Testing was performed (and results provided) in triplicate for each dilution. (y-axis=$OD_{450\ nm}$).
Figure 7:
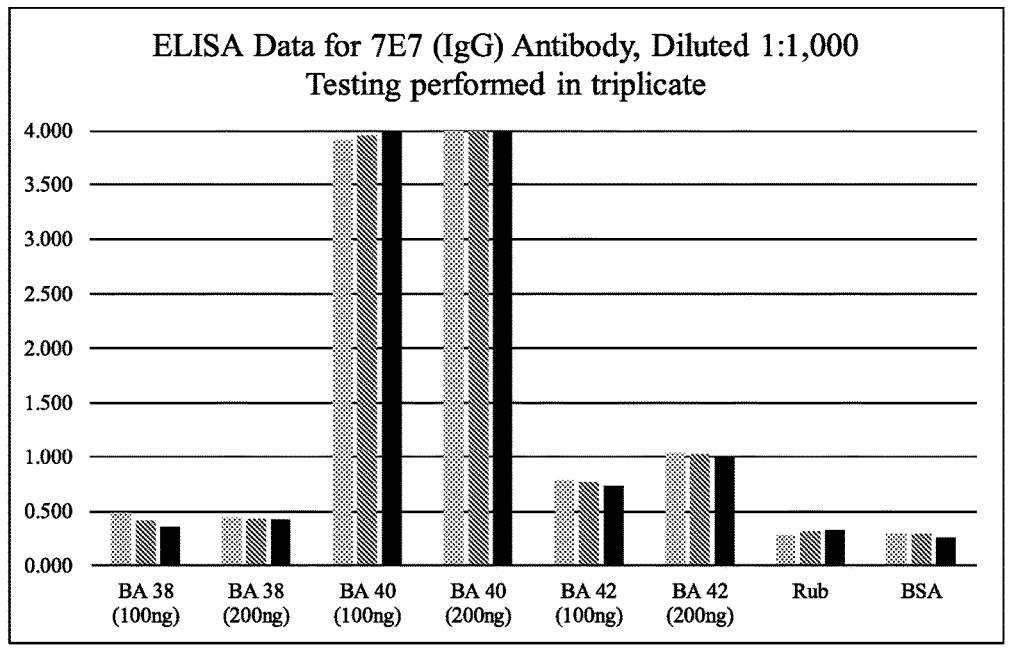
FIG. 7 provides a graphic illustration of the ELISA data for mAb 7E7 on rub-Aβ 1-38, rub-Aβ 1-40, and rub-Aβ 1-42. Testing was performed (and results provided) in triplicate for each dilution. (y-axis=$OD_{450\ nm}$).
Figure 8:
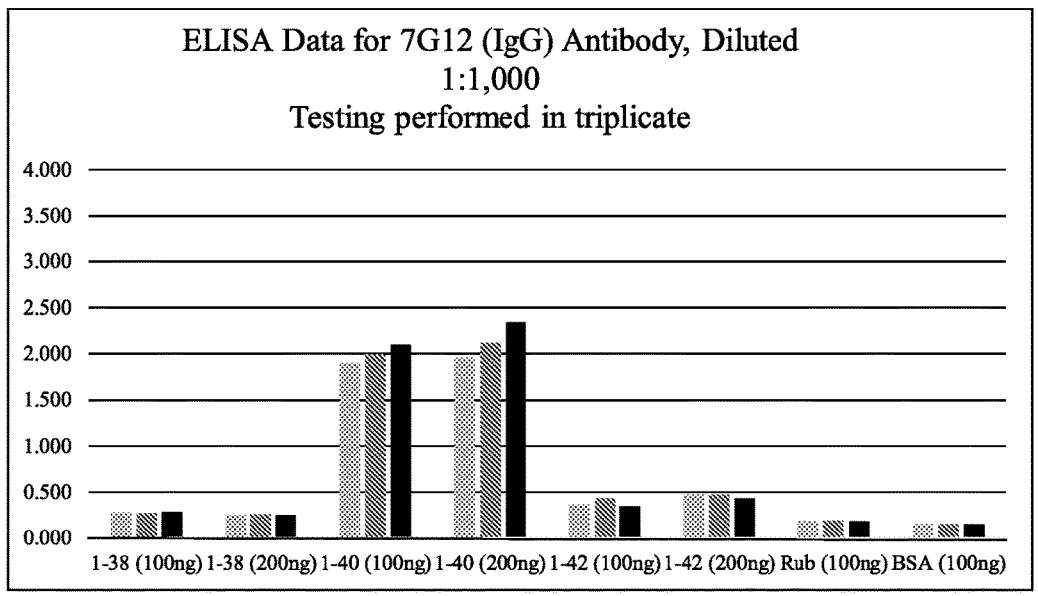
FIG. 8 provides a graphic illustration of the ELISA data for mAb 7G12 on rub-Aβ 1-38, rub-Aβ 1-40, and rub-Aβ 1-42. Testing was performed (and results provided) in triplicate for each dilution. (y-axis=$OD_{450\ nm}$).

Antibody 7E7 was primarily chosen for further study, in addition to 3H11 (FIG. 3) and 7G12 (FIG. 8).

Example 2—mAb 7E7—Antigen Binding Conditions

Figure 9:
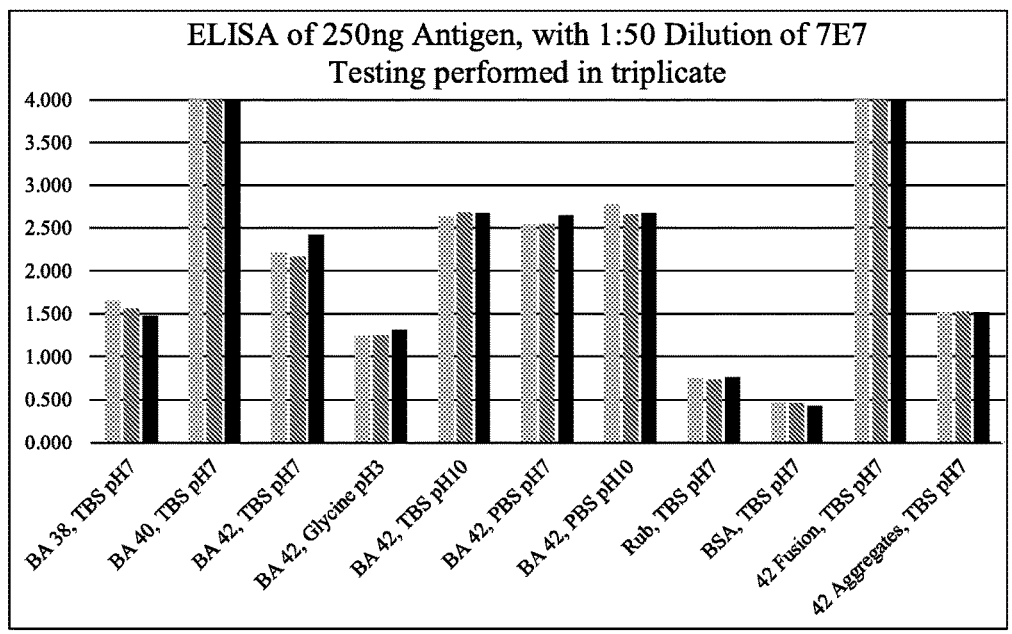
FIG. 9 provides a graphic illustration of the ELISA data for mAb 7E7 on rub-Aβ 1-38, rub-Aβ 1-40, and rub-Aβ 1-42 under varying binding conditions at a dilution of 1:50. Testing was performed (and results provided) in triplicate for each composition. (y-axis=$OD_{450\ nm}$).
Figure 10:
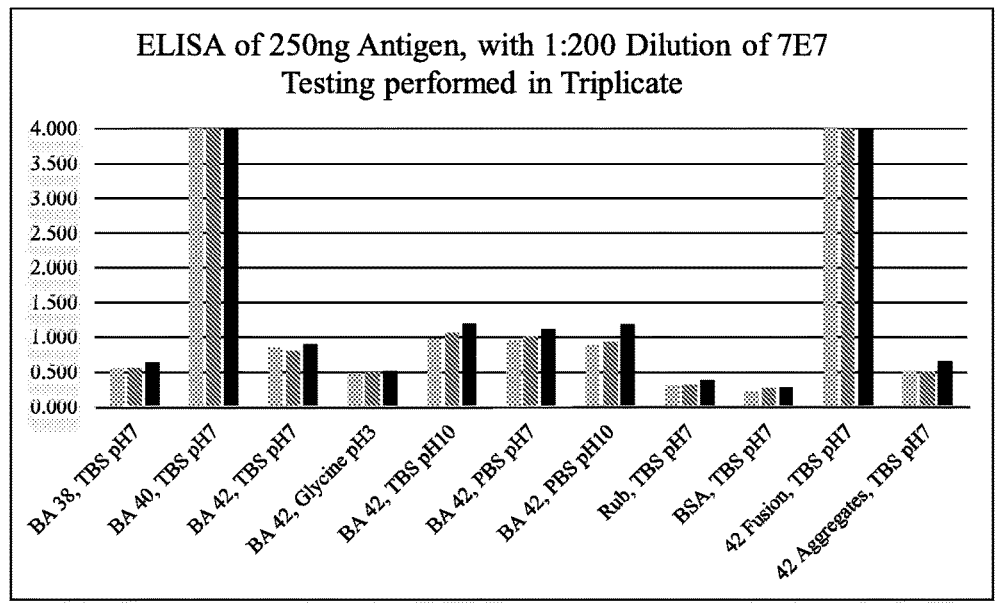
FIG. 10 provides a graphic illustration of the ELISA data for mAb 7E7 on rub-Aβ 1-38, rub-Aβ 1-40, and rub-Aβ 1-42 under varying binding conditions at a dilution of 1:200.

Tests were conducted to determine why the 7E7 mAb, which was raised against 1-42 Rubredoxin Fusion, bound so strongly to an Aβ-1-40 peptide and not an Aβ 1-42 peptide. These peptides were bound to plates in buffers at different pH values in an attempt to see if Aβ 1-42 simply needed the right conditions to actually be bound to the plate. Larger quantities of both antigen and antibody were used as well. In the end, as shown in FIGS. 9 and 10, varying the buffers and pH did not resolve this binding discrepancy.

FIG. 11 illustrates similar ELISA results which were performed to test the limits of how much 7E7 could be diluted. As shown, mAb 7E7 showed a stronger interaction with Aβ 1-40 than with Aβ-1-42.

ELISA testing on 7E7 in TBS with a pH of 10.0 was then performed using various fragments of Aβ 1-40 and Aβ 1-42 peptide. As positive test controls, these results were compared with the following known antibodies: 6E10 (Covance# SIG-39320), 4G8 (Covance# SIG-39220), and 11A50-B10 (Covance#39146). Results are shown in FIGS. 12-15, and FIG. 16 provides comparative values (averaged) for each of these figures.

Example 3—mAb 7E7—Antigen Charge for Binding

In conjunction with the testing above, and in an effort to resolve the low binding affinity to Aβ 1-42, ELISA testing of 7E7 to varying lots of Aβ 1-40 and Aβ 1-42 was performed. The results of these tests are illustrated in FIG. 17, which at first glance illustrates inconsistent binding to the target peptide. After purifying the peptide and testing samples all along the way in an ELISA assay, however, it was determined that 7E7 binds strongly and consistently with peptides that have not been allowed to cross through its isoelectric point, which is at a pH of 5.3. The majority of the purification of beta amyloid takes place at a pH well above the isoelectric point, but in the final step of the process the peptide is lyophilized in trifluoroacetic acid. When this step is removed from the process, thus removing crossing through the isoelectric point, the resulting peptide was highly reactive with 7E7, as evident by lot numbers of FIG. 17 with high binding affinities.

Peptide prepared in this manner was then tested by binding in different buffers, for example the same $NH_4OH$ which is used to dissolve the peptide when it is in lyophilized form. Results from that assay are shown in FIGS. 18 and 19. These results show a trend towards stronger interaction with 7E7 the closer the peptide is allowed to get to the isoelectric point without actually crossing through it. Thus it appears 7E7 binds peptide that undergoes a conformational change which may bring the peptide closer to being on the verge of aggregation. 6E10 is run alongside 7E7 to show that the same amount of peptide is being bound in all of the wells.

While not intending to be bound by theory, it is believed that at a pH below Aβ's isoelectric point asparagine residue at position 27 of either or both the Aβ(1-40) and Aβ(1-42) undergo irreversible deamidation. While outside of the epitope for 7E7, it is believed that the change caused by this deamidation impacts the availability of the epitope for 7E7 binding. As noted above, much of the purification process used for isolating the Aβ peptide occurred at a high pH, but lyophilization occurs at a low pH which is conducive for deamidation. When this low pH step was removed, it is believed that deamidation was prevented and the binding site for 7E7 remained available.

Example 4—mAb 7E7—Antigen Form for Binding

Western blots were performed to determine the extent of 7E7 binding to human Beta-Amyloid, specifically to determine if the antibody binds to Aβ aggregates, Aβ monomer, or both. This procedure applies to any Aβ peptide or peptide fragment which is composed of up to and including 40 or 42 amino acids. Before beginning the assay the vials of Aβ to be used were treated with 1,1,1,3,3,3-Hexafluoro-2-propanol (Aldrich Chemistry #105228-100G) (also known as HFIP) at a rate of 150 µL HFIP per 0.5 mg peptide). Once the HFIP was added to the lyophilized pellet the vials were sonicated for exactly one minute, or until the solution was clear. Once the dissolved peptide had taken on a clear appearance, the HFIP was gently evaporated out of each vial by passing Argon gas directly into the vial with the rubber stopper open just enough to allow the gasses and fumes to escape. When the inside of the vials was free of any remaining liquid, the remaining peptide is dissolved with 1% Ammonium Hydroxide at a rate which yields a peptide concentration of 1 mg/mL. 10 µL of this solution was mixed with 90 µL of Milli-Q water, and from that 100 µL mixture 20 µL was added to 50 µL XT Sample Buffer (Bio-Rad #161-0791) and 130 µL Milli-Q water for a final sample volume of 200 µL. No 2-Mercaptoethanol was added, and the samples were not heated. Furthermore the vials were not mixed via vortex as it has been shown to speed up aggregation of Aβ peptides. Instead the mixture was gently mixed by using a pipette.

Twenty (20) µL of each sample was loaded in duplicate on a 12% Bis-Tris Criterion XT Precast Gel (Bio-Rad #345-

0117) with 12+2 lanes. A total of six experimental samples were run in duplicate on each one of these gels. Sample 1 was loaded in lanes 1, and 7; Sample 2 was loaded in lanes 2, and 8; and so on up to six samples. Three (3) μL of Western C Standards (Bio-Rad #161-0376) was added to the well to the left of lane 1 that is designated for molecular weight markers. The second of these weight marker designated wells was immediately to the right of lane 12, and to it was added 5 μL of Precision Plus Protein Dual Xtra Standards (Bio-Rad #161-0377). This gel loading scheme used so that the left half (lanes 1-6) can be used for the blotting procedure, and the right half (lanes 7-12) can be silver stained to ensure that the target protein is present before running the transfer. The gel was run in 1× XT MES Running Buffer, which was made by mixing 950 mL Milli-Q water with XT MES Running Buffer, 20× (Bio-Rad #161-0789). A constant 200 Volts is applied for exactly 45 minutes.

Once the run was complete the gel was cut in half between lanes six and seven. The half with lanes 1-6 were placed in the western blot transfer buffer (50 mM Tris/40 mM Glycine/1.3 mM SDS/20% Methanol) and gently rocked for 5-10 minutes. The other half of the gel was stained using the Pierce Silver Stain Kit (Thermo Scientific #24612). The gel half with lanes 1-6 was then used in the transfer process, in which the peptides were transferred onto a PVDF membrane with a pore size not to exceed 0.2 Micron. This was done using a semi-dry transfer system from Bio-Rad (Bio-Rad #170-3940), and the conditions necessary for full transfer were 17 Volts for 17 minutes. Following the transfer, the PVDF membrane was incubated in 75 mL blocking buffer (50 mM Tris/150 mM NaCl/3.0% BSA, pH 7.4) for one hour at 25° C., or overnight at 4° C. 100 mL Wash Buffer, which is 50 mM Tris/150 mM NaCl/0.1% Tween 20, was used to wash the membrane three times for five minutes (15 minutes total) before applying the primary antibody.

Primary antibody 7E7 was prepared at a dilution of 1:1,000 in 50 mL of wash buffer containing 1% BSA (Fisher #BP1605-100), and it was incubated with the membrane for 1 hour at 25° C. The membrane was then washed three times with 100 mL wash buffer (50 mM Tris/150 mM NaCl/0.1% Tween 20) for five minutes per wash. The secondary antibody solution was then prepared using 50 mL wash buffer containing 1% BSA and 10 μL Goat Anti-Mouse IgG (H+L) HRP-Conjugate (Bio-Rad #170-6516), which gives a 1:5,000 Dilution. To ensure the protein standards are visible during the final step this solution also required the addition of 2.5 μL Precision Protein StrepTactin-HRP Conjugate (Bio-Rad #161-380). The membrane was incubated in the secondary antibody solution for one hour at 25° C. followed by 3, 5 minute rinses with 100 mL wash buffer.

In order to image the membranes, 8 mL of Pierce ECL Western Blotting Substrate (Thermo Scientific #32106) was poured on the membranes and incubated for one minute at 25° C. The membrane was then removed from the substrate solution and covered with one layer of plastic film. The blot was imaged by exposing it to GE Hyperfilm ECL (Item #45-001-507) for up to 5 minutes.

FIG. 20 illustrates the results of this procedure. More specifically, it shows a silver stained Bio-Rad 12% Bis-Tris Criterion XT Precast Gel on the left, and on the right is the corresponding western blot of the same samples with 7E7 as the primary antibody. Sample 1 is Beta-Amyloid 1-40 prepared without crossing the pI. The same conditions of peptide preparation apply to sample 3, which is Beta-Amyloid 1-42 that has not crossed through its pI. Sample 2 on the other hand is Beta Amyloid 1-42 that was prepared using the original protocol and then dried after having crossed through the pI. 7E7 binds only to the Beta-Amyloid Monomer, and there is absolutely no cross reaction with the low weight aggregates or any of the higher weight aggregates and oligomers. Furthermore 7E7 only binds to certain Beta-Amyloid monomers of both 1-40 and 1-42.

FIG. 21 illustrates the trend from ELISA data of 7E7 against samples that were obtained during an assay which forces aggregation of 1-42. The values on the X-Axis represent time, and as can be seen the amount of monomer decreases as expected during aggregation.

FIG. 22 illustrates Thioflavin T results from the same aggregation assay. There is an inverse relationship between the traditional Thioflavin T assay and an assay using 7E7 to detect the aggregation rate of beta amyloid. The 1-42 peptide was first resuspended in either 0.05% NH4OH, or 5 mM Tris. The peptide was then placed into either PBS or TBS, and the reaction mixtures were then incubated for three hours at 37° C. Samples were taken every 15 minutes to obtain this data.

Example 5—7E7 mAb Sequencing

Approximately $3.0 \times 10^6$ hybridoma cells, per clone, were collected and washed via centrifugation. Total RNA was extracted and mRNA was subsequently purified from the pelleted cells. The mRNA was then converted to cDNA utilizing reverse transcriptase.

Specifically designed degenerate primer sets (Novagen User Protocol TB326 Rev C 0308, www.emdmillipore.com; I=Inosine) are used to amplify both the heavy and light chain variable regions from the cDNA pool. The exact degenerate primers combinations utilized were chosen on the basis of the antibody isotype (both heavy and light chain isotypes) and are provided below.

```
IgG-VH3'
                                          (SEQ ID NO: 25)
(5'-CC CAAGCTTCCAGGGRCCARKGGATARACIGRTGG-3')

Igκ-VL3'
                                          (SEQ ID NO: 26)
(5'-CCCAAGCTTACTGGATGGTGGGAAGAT-GGA-3')

Igλ-VL3'
                                          (SEQ ID NO: 27)
(5'-CCCAAGCTTAGCTCYTCWG-WGGAIGGYGGRAA-3')
```

The amplified PCR products are gel purified and subsequently extracted. The isolated variable domains are ligated into vectors followed by transformation and plasmid isolation. The final plasmids are sequenced to determine the DNA code of the variable regions. The final sequences were obtained:

```
Variable Heavy Chain Protein Sequence for 7E7:
                                          (SEQ ID NO: 6)
EVKLVESGGGLVQPGSSQRLSCATSGFTFTDYYMSW

VRQPPGKALEWLGFIRNKTKRYTTEYSASVKGRFTIS

RDNSQSILYLQMNTLRAEDSATYYCARDDPYARFAY

WGQGTLVTVSA

Variable Heavy Chain DNA Sequence of 7E7:
                                          (SEQ ID NO: 16)
GAGGTGAAGCTGGTGGAGTCTGGAGGAGGCTTGGT
```

-continued

```
ACAGCCTGGGAGTTCTCAGAGACTCTCCTGTGCAA

CTTCTGGGTTCACCTTCACTGACTACTACATGAGCT

GGGTCCGCCAGCCTCCAGGAAAGGCACTTGAGTGG

TTGGGTTTTATTAGAAACAAAACTAAACGTTACAC

AACAGAATACAGTGCATCTGTGAAGGGTCGGTTCA

CCATCTCCAGAGATAATTCCCAAAGCATCCTCTATC

TTCAAATGAACACCCTGAGAGCTGAGGACAGTGCC

ACTTATTACTGTGCAAGAGATGATCCGTACGCACG

GTTTGCTTACTGGGGCCAAGGGACTCTGGTCACTGT

CTCTGCA

Variable Light Chain Protein Sequence for 7E7:
                                    (SEQ ID NO: 5)
DVVMTQTPLSLPVSLGDQASISCRSGQSLVHRNGNTY

LHWYLQKPGQSPKLLIYKVSNRFSGVPDRFSGSGTGT

DFTLKISRVEAEDLGVYFCSQSTHVPFTFGSGTKLEIK

Variable Light Chain DNA Sequence of 7E7:
                                    (SEQ ID NO: 15)
GATGTTGTGATGACCCAAACTCCACTCTCCCTGCCT

GTCAGTCTTGGAGATCAAGCCTCCATCTCTTGCAGA

TCTGGTCAGAGCCTTGTACACAGAAATGGAAACAC

CTATTTACATTGGTACCTGCAGAAGCCAGGCCAGT

CTCCAAAGCTCCTGATCTACAAAGTTTCCAACCGAT

TTTCTGGGGTCCCAGACAGGTTCAGTGGCAGTGGA

ACAGGGACAGATTTTACACTCAAGATCAGCAGAGT

GGAGGCTGAGGATCTGGGAGTTTATTTCTGCTCTCA

AAGTACACATGTTCCATTCACGTTCGGCTCGGGGA

CAAAGTTGGAAATAAAA
```

Example 6—7E7 CDR Regions

The complementarity determining regions (CDR) within the heavy and light chains for the Beta Amyloid 7E7 antibody was determined using the Chothia Method (Chothia et al., (1987) JMB 196, 901-917) and Kabat Method (Kabat et al., U.S. Department of Health and Human Services, "Sequences of Proteins of Immunological Interest", 1983). These are the most utilized numbering systems to annotate the CDRs of monoclonal antibodies. Below are a series of tables and sequences defining the CDRs in the heavy and light chains of the 7E7 antibody:

```
Heavy Chain Protein Sequence for 7E7:
                                    (SEQ ID NO: 6)
EVKLVESGGGLVQPGSSQRLSCATSGFTFTDYYMSW

VRQPPGKALEWLGFIRNKTKRYTTEYSASVKGRFTIS

RDNSQSILYLQMNTLRAEDSATYYCARDDPYARFAY

WGQGTLVTVSA

Light Chain Protein Sequence for 7E7:
                                    (SEQ ID NO: 5)
DVVMTQTPLSLPVSLGDQASISCRSGQSLVHRNGNTY

LHWYLQKPGQSPKLLIYKVSNRFSGVPDRFSGSGTGT

DFTLKISRVEAEDLGVYFCSQSTHVPFTFGSGTKLEIK
```

TABLE 21

Chothia Heavy Chain CDR Analysis for 7E7

| | Sequence | Residues | Length |
|---|---|---|---|
| CDR-H1 | GFTFTDY (SEQ ID NO: 10) | 26-32 | 7 |
| CDR-H2 | RNKTKRYT (SEQ ID NO: 11) | 52-59 | 8 |
| CDR-H3 | DDPYARFAY (SEQ ID NO: 12) | 101-109 | 9 |

TABLE 22

Kabat Heavy Chain CDR Analysis for 7E7

| | Sequence | Residues | Length |
|---|---|---|---|
| CDR-H1 | DYYMS (SEQ ID NO: 13) | 31-35 | 5 |
| CDR-H2 | FIRNKTKRYTTEYSASVKG (SEQ ID NO: 14) | 50-68 | 19 |
| CDR-H3 | DDPYARFAY (SEQ ID NO: 12) | 101-109 | 9 |

TABLE 23

Chothia and Kabat Light Chain CDR Analysis for 7E7

| | Sequence | Residues | Length |
|---|---|---|---|
| CDR-L1 | RSGQSLVHRNGNTYLH (SEQ ID NO: 7) | 24-39 | 16 |
| CDR-L2 | KVSNRFS (SEQ ID NO: 8) | 55-61 | 7 |
| CDR-L3 | SQSTHVPFT (SEQ ID NO: 9) | 94-102 | 9 |

```
Sequence 1: Beta Amyloid 7E7 Heavy Chain with
Chothia CDRs Underlined
                                    (SEQ ID NO: 6)
EVKLVESGGGLVQPGSSQRLSCATSGFTFTDYYMSW

VRQPPGKALEWLGFIRNKTKRYTTEYSASVKGRFTIS

RDNSQSILYLQMNTLRAEDSATYYCARDDPYARFAY

WGQGTLVTVSA

Sequence 2: Beta Amyloid 7E7 Heavy Chain with
Kabat CDRs Underlined
                                    (SEQ ID NO: 6)
EVKLVESGGGLVQPGSSQRLSCATSGFTFTDYYMSW

VRQPPGKALEWLGFIRNKTKRYTTEYSASVKGRFTIS

RDNSQSILYLQMNTLRAEDSATYYCARDDPYARFAY

WGQGTLVTVSA

Sequence 3: Beta Amyloid 7E7 Light Chain with
Chothia and Kabat CDRs Underlined
```

-continued (SEQ ID NO: 5)
DVVMTQTPLSLPVSLGDQASISC<u>RSGQSLVHRNGNTY</u>

<u>LHWYLQKPGQSPKLLIY</u><u>KVSNRFS</u>GVPDRFSGSGTGT

DFTLKISRVEAEDLGVYFC<u>SQSTHVPFT</u>FGSGTKLEIK

Example 7—7E7 Epitope Mapping

To reconstruct discontinuous epitopes of the target molecule, a library of structured peptides was synthesized. This was done using Pepscan's proprietary Chemically Linked Peptides on Scaffolds (CLIPS) technology. CLIPS technology allows to structure peptides into single loops, double loops, triple loops, sheet-like folds, helix-like folds, and combinations thereof. CLIPS templates were coupled to side-chain thiol groups of cysteine residues. The side-chains of (multiple) cysteines in the peptides were coupled to one or two CLIPS templates. More specifically, a 0.5 mM solution of the T2 CLIPS template 1,3-bis (bromomethyl) benzene was dissolved in ammonium bicarbonate (20 mM, pH 7.9)/acetonitrile 1:1 (v/v). This solution was added to the peptide arrays. The CLIPS template binds to the side-chains of two cysteines as present in the solid-phase bound peptides of the arrays (455 well-plate with 3 µl wells). The peptide arrays were gently shaken for 30 to 60 minutes while completely covered in the aforementioned solution. Finally, the peptide arrays were washed extensively with an excess of $H_2O$, and sonicated in a disrupt-buffer containing 1% SDS/0.1% beta-mercaptoethanol in PBS (pH 7.2) at 70° C. for 30 minutes, followed by sonication in $H_2O$ for another 45 minutes. The T3 CLIPS carrying peptides were prepared likewise but now with three cysteines.

The binding of antibody to each of the synthesized peptides was tested in a PEPSCAN-based ELISA. In this assay, the peptide arrays were incubated with primary antibody solution (overnight at 4° C.). After washing, the peptide arrays were incubated with a 1/1000 dilution of an antibody peroxidase conjugate (SBA, cat. nr. 2010-05) for one hour at 25° C. After washing, the peroxidase substrate 2,2'-azino-di-3-ethylbenzthiazoline sulfonate (ABTS) and 2 µl/ml of 3% H2O2 were added. After one hour, the color development was measured. The color development was quantified with a charge coupled device (CCD) camera and an image processing system.

The values obtained from the CCD camera ranged from 0 to 3000 mAU, similar to a standard 96-well plate ELISA-reader. The results were quantified and stored into the Peplab database. Occasionally, a well may contain an air-bubble resulting in a false positive value. To avoid this issue, cards were manually inspected, and any values caused by an air-bubble are scored as 0.

To assess the quality of the synthesized peptides, a separate set of positive and negative control peptides was synthesized in parallel. Such peptide sets were screened with antibody 57.9 (ref. Posthumus et al., J. Virol. 1990, 64: 3304-3309).

Antibody binding depends on a combination of factors, which include the concentration of the antibody, and also the amount and nature of competing proteins in the ELISA buffer. The pre-coating conditions (i.e the specific treatment of the peptide arrays prior to incubation with the experimental sample) also affect the binding of the antibody. Detailed conditions for the screening are summarized in Table 24. For the ELISA buffer and the pre-conditioning (SQ), the values depicted in the Table indicate the relative amount of competing protein (i.e a combination of horse serum and ovalbumin).

TABLE 24

| | Screening Conditions | | |
|---|---|---|---|
| Sample | Dilution | Sample buffer | Preconditioning |
| 7E7 | 1 ug/ml | 0.1% SQ | 0.1% SQ |
| 7E7 | 10 ug/ml | 0.1% SQ | 0.1% SQ |

The 7E7 mAb was tested under low stringency conditions, as illustrated in FIG. 26, no clear or unequivocal common core that is essential for the binding of this antibody. Only short stretches near the N- and C-termini of the 42-mer sequence display significantly less binding. 7E7 also showed increased binding when the C-terminal stretch of the Aβ peptide was omitted.

In a similar vein, there was no single amino acid replacement that abolished binding to the peptide mimic (see FIG. 27). Again, some loss of binding was seen for replacements in the stretch between residues V12 and V24. Taken together with the window-net data (i.e Peptide Set 2), these results suggest that the core epitope recognized by 7E7 resides within the V12-V24 region of the peptide sequence—i.e VHHQKLVFFAEDV (SEQ ID NO: 3).

Example 8—6C2 mAb

In conjunction with the experiments above and using the same techniques, mAb 6C2 was also discovered as binding to the Aβ 1-40 and Aβ 1-42 proteins. Much like 7E7, it also reacts best with peptide that has not crossed through the isoelectric point. Shown in FIG. 23 are ELISA results with 7E7 and 6C2 tested against 1-42 prepared in the same manner as described above. From each batch, peptide was tested that had not been concentrated, and some was also tested that had been concentrated by roto-vap.

Unlike 7E7, however, 6C2 does not bind to Aβ monomer; rather, it binds strongly to aggregated tetramer, which are four monomers stuck together. This much is illustrated in FIG. 24, which provides an SDS-PAGE gel containing samples from this aggregation assay of 1-42. The oligomers bound by 6C2 are labeled. Note the increase in oligomers unable to travel through the bottom of the wells at the top of the gel. This is due to their weight. Therefore the ELISA data gathered from testing it against aggregating 1-42 samples is similar to the curve generated from the Thioflavin T samples. (FIG. 25).

Example 9—6C2 Epitope Mapping

To reconstruct discontinuous epitopes of the target molecule, a library of structured peptides was synthesized. This was done using Pepscan's proprietary Chemically Linked Peptides on Scaffolds (CLIPS) technology. CLIPS technology allows to structure peptides into single loops, double loops, triple loops, sheet-like folds, helix-like folds, and combinations thereof. CLIPS templates were coupled to side-chain thiol groups of cysteine residues. The side-chains of (multiple) cysteines in the peptides were coupled to one or two CLIPS templates. More specifically, a 0.5 mM solution of the T2 CLIPS template 1,3-bis (bromomethyl) benzene was dissolved in ammonium bicarbonate (20 mM, pH 7.9)/acetonitrile 1:1 (v/v). This solution was added to the peptide arrays. The CLIPS template binds to the side-chains of two cysteines as present in the solid-phase bound peptides of the arrays (455 well-plate with 3 µl wells). The peptide arrays were gently shaken for 30 to 60 minutes while completely covered in the aforementioned solution. Finally, the peptide arrays were washed extensively with an excess of $H_2O$, and sonicated in a disrupt-buffer containing 1% SDS/0.1% beta-mercaptoethanol in PBS (pH 7.2) at 70° C. for 30 minutes, followed by sonication in $H_2O$ for another 45 minutes. The T3 CLIPS carrying peptides were prepared likewise but now with three cysteines.

The binding of antibody to each of the synthesized peptides was tested in a PEPSCAN-based ELISA. In this assay, the peptide arrays were incubated with primary antibody solution (overnight at 4° C.). After washing, the peptide arrays were incubated with a 1/1000 dilution of an antibody peroxidase conjugate (SBA, cat. nr. 2010-05) for one hour at 25° C. After washing, the peroxidase substrate 2,2'-azino-di-3-ethylbenzthiazoline sulfonate (ABTS) and 2 µl/ml of 3% $H_2O_2$ were added. After one hour, the color development was measured. The color development was quantified with a charge coupled device (CCD) camera and an image processing system.

The values obtained from the CCD camera range from 0 to 3000 mAU, similar to a standard 96-well plate ELISA-reader. The results were quantified and stored into the Peplab database. Occasionally, a well may contain an air-bubble resulting in a false positive value. To avoid this issue, cards were manually inspected, and any values caused by an air-bubble are scored as 0.

To assess the quality of the synthesized peptides, a separate set of positive and negative control peptides was synthesized in parallel. Such peptide sets were screened with antibody 57.9 (ref. Posthumus et al., J. Virol. 1990, 64: 3304-3309).

Antibody binding depends on a combination of factors, which include the concentration of the antibody, and also the amount and nature of competing proteins in the ELISA buffer. The pre-coating conditions (i.e the specific treatment of the peptide arrays prior to incubation with the experimental sample) also affect the binding of the antibody. Detailed conditions for the screening are summarized in Table 25, below. For the ELISA buffer and the pre-conditioning (SQ), the values depicted in the Table indicate the relative amount of competing protein (i.e a combination of horse serum and ovalbumin). P/T indicates a PBS/Tween mix without competing protein.

TABLE 25

Screening Conditions

| Sample | Dilution | Sample buffer | Preconditioning |
|--------|----------|---------------|-----------------|
| 6C2    | 5 ug/ml  | P/T           | 1% SQ           |

FIG. 28 provides box plot graphs of the raw data of the antibody screening. Each box plot corresponds to a dataset, and indicates the average ELISA signal, the distribution of ELISA signals, and the outliers within such dataset. Depending on the experiment conditions (e.g. amount of antibody, blocking strength, etc.), different distributions of ELISA data are obtained. The bottom and top of the boxes are the $25^{th}$ and $75^{th}$ percentile of the data. The band near the middle of the box is the $50^{th}$ percentile (the median). The whiskers are at 1.5 the inter-quantile range, and indication of statistical outliers within the data set.

6C2 was tested under moderate stringency conditions, and did not bind reliably to the peptides in the 42-mer repnet (Set2). However it did bind under these conditions to the midsize peptides in the windownet (Set1). FIG. 29 illustrates such results. Specifically, 6C2 tested on Peptide Set 1 (i.e window-net), showing increased binding when the C-terminal stretch is omitted from the sequence. For reliable binding a contiguous series from A2 to E22 is needed.

Collectively, such data demonstrates that the 6C2 mAb binds Aβ most efficiently when the stretch A2-E22 is present in the peptides. This is a long stretch for an epitope. While not intending to be bound by theory, it is likely this either reflects that secondary structure is of importance, which is conferred by residues this far apart in the primary sequence. Such an observation would be consistent with binding of this antibody to elongated beta sheets, as are thought to be formed in fibrillar aggregates. Alternatively this antibody recognizes a discontinuous epitope. This might be the case for an anti-oligomer antibody, but would not fit with a model of Aβ in an elongated beta sheet.

Example 10—6C2 mAb Sequencing

DNA sequence analysis of the light and heavy variable chains of the 6C2 monoclonal antibody were identified via standard RACE methodology. Total RNA was extracted from h6C2 hybridoma cells, where the mRNA was denatured and converted to cDNA utilizing reverse transcriptase. cDNA was amplified via a 5' RACE reaction and correctly sized PCR products corresponding to the light and heavy variable regions were subcloned in TOPO-based expression vectors, amplified, subject to gel electrophoresis, extracted, purified and subject to sequence analysis by standard methodology.

```
Variable Heavy Chain Protein Sequence for 6C2:
                                (SEQ ID NO: 43)
EVQLQQSGPELVKPGASVKISCKASGYSFTGYFLSWV

KQSHGRSLEWIGRINPYNGHTFYNQKFKDKATLTVD

KSSTTAHMELLSLTSEDSAVYYCAGSDSWGQGTTLT

VSS

Variable Heavy Chain DNA Sequence of 6C2:
                                (SEQ ID NO: 45)
GAGGTTCAGCTGCAGCAGTCTGGACCTGAACTGGT

GAAGCCTGGGGCTTCAGTGAAGATTTCCTGCAAGG

CTTCTGGTTACTCATTTACTGGCTACTTTTTGAGCTG

GGTGAAGCAGAGCCATGGAAGGAGCCTTGAGTGG

ATTGGACGTATTAATCCTTACAATGGTCATACTTTC

TACAACCAGAAGTTCAAGGACAAGGCCACATTGAC

TGTTGACAAATCCTCTACCACAGCCCACATGGAGC

TCCTGAGCCTGACATCTGAGGACTCTGCAGTCTATT

ATTGTGCAGGATCTGACTCCTGGGGCCAAGGCACC

ACTCTCACAGTCTCCTCA

Variable Light Chain Protein Sequence for 6C2:
                                (SEQ ID NO: 42)
DVVMTQTPLTLSVTIGQPASISCKSSQSLLDSDGKTYL

NWLLQRPGQSPKRLIFLVSKLDSGVPDRFTGSGSGTD
```

-continued

FTLKISSVEAEDLGIYYCWQGTHFPWTFGGGTKLEIK

Variable Light Chain DNA Sequence of 6C2:
(SEQ ID NO: 44)
GATGTTGTGATGACCCAGACTCCACTCACTTTGTCG

GTTACCATTGGACAACCAGCCTCCATCTCTTGCAAG

TCAAGTCAGAGCCTCTTAGATAGTGATGGAAAGAC

ATATTTGAATTGGTTGTTACAGAGGCCAGGCCAGT

CTCCAAAGCGCCTAATCTTTCTGGTGTCTAAACTGG

ACTCTGGAGTCCCTGACAGGTTCACTGGCAGTGGA

TCAGGGACAGATTTCACACTGAAAATCAGCAGCGT

GGAGGCTGAGGATTTGGGAATTTATTATTGCTGGC

AAGGTACACATTTTCCGTGGACGTTCGGTGGAGGC

ACCAAGCTGGAAATCAAAC

Example 11—6C2 CDR Regions

The complementarity determining regions (CDR) within the heavy and light chains for 6C2 were also determined using the Chothia Method (Chothia et al., (1987) JMB 196, 901-917) and Kabat Method (Kabat et al., U.S. Department of Health and Human Services, "Sequences of Proteins of Immunological Interest", 1983). The tables below define the respective CDRs in the heavy and light chains of 6C2:

Heavy Chain Protein Sequence for 6C2:
(SEQ ID NO: 43)
EVQLQQSGPELVKPGASVKISCKASGYSFTGYFLSWV

KQSHGRSLEWIGRINPYNGHTFYNQKFKDKATLTVD

KSSTTAHMELLSLTSEDSAVYYCAGSDSWGQGTTLT

VSS

Light Chain Protein Sequence for 6C2:
(SEQ ID NO: 42)
DVVMTQTPLTLSVTIGQPASISCKSSQSLLDSDGKTYL

NWLLQRPGQSPKRLIFLVSKLDSGVPDRFTGSGSGTD

FTLKISSVEAEDLGIYYCWQGTHFPWTFGGGTKLEIK

TABLE 26

Chothia Heavy Chain CDR Analysis for 6C2

| | Sequence | Residues | Length |
|---|---|---|---|
| CDR-H1 | GYSFTGY (SEQ ID NO: 31) | 26-32 | 7 |
| CDR-H2 | NPYNGH (SEQ ID NO: 32) | 52-57 | 6 |
| CDR-H3 | SDS | 99-101 | 3 |

TABLE 27

Kabat Heavy Chain CDR Analysis for 6C2

| | Sequence | Residues | Length |
|---|---|---|---|
| CDR-H1 | GYFLS (SEQ ID NO: 33) | 31-35 | 5 |
| CDR-H2 | RINPYNGHTFYNQKFKD (SEQ ID NO: 34) | 50-66 | 17 |
| CDR-H3 | SDS | 99-101 | 3 |

TABLE 28

Chothia and Kabat Light Chain CDR Analysis for 6C2

| | Sequence | Residues | Length |
|---|---|---|---|
| CDR-L1 | KSSQSLLDSDGKTYLN (SEQ ID NO: 28) | 24-39 | 16 |
| CDR-L2 | LVSKLDS (SEQ ID NO: 29) | 55-61 | 7 |
| CDR-L3 | WQGTHFPWT (SEQ ID NO: 30) | 94-102 | 9 |

Sequence 1: Beta Amyloid 6C2 Heavy Chain with Chothia CDRs Underlined
(SEQ ID NO: 43)
EVQLQQSGPELVKPGASVKISCKAS<u>GYSFTGY</u>FLSWV KQSHGRSLEWIGRI<u>NPYNGH</u>TFYNQKFKDKATLTVD KSSTTAHMELLSLTSEDSAVYYCAG<u>SDS</u>WGQGTTLT

VSS

Sequence 2: Beta Amyloid 6C2 Heavy Chain with Kabat CDRs Underlined
(SEQ ID NO: 43)
EVQLQQSGPELVKPGASVKISCKASGYSFT<u>GYFLS</u>WV KQSHGRSLEWIG<u>RINPYNGHTFYNQKFKD</u>KATLTVD KSSTTAHMELLSLTSEDSAVYYCAG<u>SDS</u>WGQGTTLT

VSS

Sequence 3: Beta Amyloid 6C2 Light Chain with Chothia and Kabat CDRs Underlined
(SEQ ID NO: 42)
DVVMTQTPLTLSVTIGQPASISC<u>KSSQSLLDSDGKTYL</u>

<u>N</u>WLLQRPGQSPKRLIF<u>LVSKLDS</u>GVPDRFTGSGSGTD

FTLKISSVEAEDLGIYYC<u>WQGTHFPWT</u>FGGGTKLEIK

DEPOSIT OF HYBRIDOMA CELL LINES

The following hybridoma was deposited with the American Type Culture Collection (ATCC, Manassas, Va.) on Feb. 24, 2015, and assigned the following ATCC designation:

1. Hybridoma h7E7 producing mAb 7E7 was assigned ATCC designation PTA-122040, and designated as strain "Beta Amyloid 7E7."

The following hybridoma was deposited with the American Type Culture Collection (ATCC, Manassas, Va.) on Jun. 16, 2015, and assigned the following ATCC designation:

1. Hybridoma h6C2 producing mAb 6C2 was assigned ATCC designation PTA-122245, and designated as strain "Beta Amyloid 6C2."

What is claimed is:

1. An isolated antibody or fragment thereof that specifically interacts and shows measurable affinity to an epitope of at least one amyloid-beta protein isoform, the isolated antibody or fragment comprising variable light chain complementarity determining regions that are SEQ ID NO: 7—CDR 1; SEQ ID NO: 8—CDR 2; and SEQ ID NO: 9—CDR 3, and further comprising variable heavy chain complementarity determining regions that are SEQ ID NO: 10—CDR 1; SEQ ID NO: 11—CDR 2; and SEQ ID NO: 12, or in the alternative SEQ ID NO: 13—CDR 1; SEQ ID NO: 14—CDR 2; and SEQ ID NO: 12—CDR 3.

2. The isolated antibody or fragment thereof of claim 1, wherein the amyloid-beta protein isoform is selected from the group consisting of monomeric Aβ(1-40) and monomeric Aβ(1-42).

3. The isolated antibody or fragment thereof of claim 1, wherein the isolated antibody or fragment thereof binds to an epitope of the amyloid-beta protein isoform having the sequence VHHQKLVFFAEDV (SEQ ID NO: 3), where at least an asparagine residue at position 27 of the amyloid-beta protein isoform has not undergone deamidation.

4. The isolated antibody of claim 3, wherein the amyloid-beta protein isoform is monomeric.

5. The isolated antibody or fragment thereof of claim 1, wherein said antibody is selected from the group consisting of a monoclonal antibody, a recombinant antibody, a chimeric antibody, and a humanized antibody.

6. The isolated antibody or fragment thereof of claim 1, wherein said antibody is raised in a mammal.

7. A pharmaceutical formulation comprising an antibody or fragment thereof, of claim 1 and a pharmaceutically acceptable carrier.

8. A recombinant vector comprising a polynucleotide encoding an antibody, or fragment thereof, of claim 1.

9. A host cell comprising the recombinant vector of claim 8.

10. A method of modulating amyloid beta activity in a cell comprising administering to a mammal in need thereof an effective amount of the antibody, or fragment thereof, of claim 1.

11. A method of modulating amyloid beta aggregation in a cell comprising administering to a mammal in need thereof an effective amount of the antibody, or fragment thereof, of claim 1.

12. A method of modulating amyloid beta amyloidosis in a cell comprising administering to a mammal in need thereof an effective amount of the antibody, or fragment thereof, of claim 1.

13. A method of treating a amyloidosis in a subject in need thereof, comprising administering a therapeutically effective amount of the antibody, or fragment thereof, of claim 1 to the subject.

14. A method of detecting the progression of amyloidosis in a human patient, comprising:
  (a) obtaining a biological sample from the patient;
  (b) contacting the biological sample with an antibody, or fragment thereof, of claim 1;
  (c) detecting the level of binding of a monomeric amyloid beta protein in the biological sample with the antibody, or fragment thereof, of claim 1; and
  (d) comparing the level of detected monomeric amyloid protein to a reference standard indicating the level of the monomeric amyloid protein in one or more control subjects.

15. The method of claim 14, wherein the amyloidosis is Alzheimer's disease.

16. The method of claim 14 wherein the monomeric amyloid-beta protein isoform is selected from the group consisting of monomeric Aβ(1-40) and monomeric Aβ(1-42).

17. The method of claim 14 wherein the isolated antibody or fragment thereof binds to an epitope of the monomeric amyloid-beta protein having the sequence VHHQKLVFFAEDV (SEQ ID NO: 3), where at least an asparagine residue at position 27 of the monomeric amyloid-beta protein has not undergone deamidation.

18. The method of claim 17 wherein the monomeric amyloid-beta protein isoform is selected from the group consisting of monomeric Aβ(1-40) and monomeric Aβ(1-42).

19. An isolated antibody or fragment thereof that specifically interacts and shows measurable binding affinity to an epitope of at least one amyloid-beta protein isoform, the isolated antibody or fragment comprising a variable light chain having an amino acid sequence of at least 90% identity to SEQ ID NO: 5, and a variable heavy chain having an amino acid sequence of at least 90% identity to SEQ ID NO: 6.

20. The isolated antibody or fragment thereof of claim 19, wherein the amyloid-beta protein isoform is selected from the group consisting of monomeric Aβ(1-40) and monomeric Aβ(1-42).

21. The isolated antibody or fragment thereof of claim 19, wherein the isolated antibody or fragment thereof binds to an epitope of the amyloid-beta protein isoform having the sequence VHHQKLVFFAEDV (SEQ ID NO: 3), where at least an asparagine residue at position 27 of the amyloid-beta protein isoform has not undergone deamidation.

22. The isolated antibody, or fragment thereof, of claim 21, wherein the amyloid-beta protein isoform is monomeric.

23. The isolated antibody or fragment thereof of claim 19, wherein said antibody is selected from the group consisting of a monoclonal antibody, a recombinant antibody, a chimeric antibody, and a humanized antibody.

24. A pharmaceutical formulation comprising an antibody, or fragment thereof, of claim 19 and a pharmaceutically acceptable carrier.

25. A recombinant vector comprising a polynucleotide encoding an antibody, or fragment thereof, of claim 19.

26. A host cell comprising the recombinant vector of claim 25.

27. A method of treating amyloidosis in a subject in need thereof, comprising administering a therapeutically effective amount of the antibody, or fragment thereof, of claim 19 to the subject.

28. A method of modulating amyloid beta activity in a cell comprising administering to a mammal in need thereof an effective amount of the antibody, or fragment thereof, of claim 19.

29. A method of modulating amyloid beta aggregation in a cell comprising administering to a mammal in need thereof an effective amount of the antibody, or fragment thereof, of claim 19.

30. A method of modulating amyloid beta amyloidosis in a cell comprising administering to a mammal in need thereof an effective amount of the antibody, or fragment thereof, of claim 19.

31. A hybridoma which is hybridoma h7E7, deposited with the American Type Culture Collection (ATCC) on Feb. 24, 2015, and assigned ATCC designation PTA-122040.

32. An isolated monoclonal antibody secreted from the hybridoma of claim 31.

* * * * *

SEQUENCE LISTING

<160> NUMBER OF SEQ ID NOS: 45

<210> SEQ ID NO 1
<211> LENGTH: 40
<212> TYPE: PRT
<213> ORGANISM: Homo sapiens

<400> SEQUENCE: 1

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
        35                  40

<210> SEQ ID NO 2
<211> LENGTH: 42
<212> TYPE: PRT
<213> ORGANISM: Homo sapiens

<400> SEQUENCE: 2

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 3
<211> LENGTH: 13
<212> TYPE: PRT
<213> ORGANISM: Homo sapiens

<400> SEQUENCE: 3

Val His His Gln Lys Leu Val Phe Phe Ala Glu Asp Val
1               5                   10

<210> SEQ ID NO 4
<211> LENGTH: 21
<212> TYPE: PRT
<213> ORGANISM: Homo sapiens

<400> SEQUENCE: 4

Ala Glu Phe Arg His Asp Ser Gly Tyr Glu Val His His Gln Lys Leu
1               5                   10                  15

Val Phe Phe Ala Glu
            20

<210> SEQ ID NO 5
<211> LENGTH: 112
<212> TYPE: PRT
<213> ORGANISM: Mus musculus

<400> SEQUENCE: 5

Asp Val Val Met Thr Gln Thr Pro Leu Ser Leu Pro Val Ser Leu Gly
1               5                   10                  15

Asp Gln Ala Ser Ile Ser Cys Arg Ser Gly Gln Ser Leu Val His Arg
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro

```
                  50                  55                  60

Asp Arg Phe Ser Gly Ser Gly Thr Gly Thr Asp Phe Thr Leu Lys Ile
 65                  70                  75                  80

Ser Arg Val Glu Ala Glu Asp Leu Gly Val Tyr Phe Cys Ser Gln Ser
                 85                  90                  95

Thr His Val Pro Phe Thr Phe Gly Ser Gly Thr Lys Leu Glu Ile Lys
                100                 105                 110

<210> SEQ ID NO 6
<211> LENGTH: 120
<212> TYPE: PRT
<213> ORGANISM: Mus musculus

<400> SEQUENCE: 6

Glu Val Lys Leu Val Glu Ser Gly Gly Gly Leu Val Gln Pro Gly Ser
  1               5                  10                  15

Ser Gln Arg Leu Ser Cys Ala Thr Ser Gly Phe Thr Phe Thr Asp Tyr
                 20                  25                  30

Tyr Met Ser Trp Val Arg Gln Pro Pro Gly Lys Ala Leu Glu Trp Leu
             35                  40                  45

Gly Phe Ile Arg Asn Lys Thr Lys Arg Tyr Thr Thr Glu Tyr Ser Ala
 50                  55                  60

Ser Val Lys Gly Arg Phe Thr Ile Ser Arg Asp Asn Ser Gln Ser Ile
 65                  70                  75                  80

Leu Tyr Leu Gln Met Asn Thr Leu Arg Ala Glu Asp Ser Ala Thr Tyr
                 85                  90                  95

Tyr Cys Ala Arg Asp Asp Pro Tyr Ala Arg Phe Ala Tyr Trp Gly Gln
                100                 105                 110

Gly Thr Leu Val Thr Val Ser Ala
        115                 120

<210> SEQ ID NO 7
<211> LENGTH: 16
<212> TYPE: PRT
<213> ORGANISM: Mus musculus

<400> SEQUENCE: 7

Arg Ser Gly Gln Ser Leu Val His Arg Asn Gly Asn Thr Tyr Leu His
  1               5                  10                  15

<210> SEQ ID NO 8
<211> LENGTH: 7
<212> TYPE: PRT
<213> ORGANISM: Mus musculus

<400> SEQUENCE: 8

Lys Val Ser Asn Arg Phe Ser
  1               5

<210> SEQ ID NO 9
<211> LENGTH: 9
<212> TYPE: PRT
<213> ORGANISM: Mus musculus

<400> SEQUENCE: 9

Ser Gln Ser Thr His Val Pro Phe Thr
  1               5

<210> SEQ ID NO 10
<211> LENGTH: 7
```

```
<212> TYPE: PRT
<213> ORGANISM: Mus musculus

<400> SEQUENCE: 10

Gly Phe Thr Phe Thr Asp Tyr
1               5

<210> SEQ ID NO 11
<211> LENGTH: 8
<212> TYPE: PRT
<213> ORGANISM: Mus musculus

<400> SEQUENCE: 11

Arg Asn Lys Thr Lys Arg Tyr Thr
1               5

<210> SEQ ID NO 12
<211> LENGTH: 9
<212> TYPE: PRT
<213> ORGANISM: Mus musculus

<400> SEQUENCE: 12

Asp Asp Pro Tyr Ala Arg Phe Ala Tyr
1               5

<210> SEQ ID NO 13
<211> LENGTH: 5
<212> TYPE: PRT
<213> ORGANISM: Mus musculus

<400> SEQUENCE: 13

Asp Tyr Tyr Met Ser
1               5

<210> SEQ ID NO 14
<211> LENGTH: 19
<212> TYPE: PRT
<213> ORGANISM: Mus musculus

<400> SEQUENCE: 14

Phe Ile Arg Asn Lys Thr Lys Arg Tyr Thr Thr Glu Tyr Ser Ala Ser
1               5                   10                  15

Val Lys Gly

<210> SEQ ID NO 15
<211> LENGTH: 336
<212> TYPE: DNA
<213> ORGANISM: Mus musculus

<400> SEQUENCE: 15
gatgttgtga tgacccaaac tccactctcc ctgcctgtca gtcttggaga tcaagcctcc      60
atctcttgca gatctggtca gagccttgta cacagaaatg gaaacaccta tttacattgg     120
tacctgcaga agccaggcca gtctccaaag ctcctgatct acaaagtttc caaccgattt     180
tctggggtcc cagacaggtt cagtggcagt ggaacaggga cagatttac actcaagatc      240 agcagagtgg aggctgagga tctgggagtt tatttctgct ctcaaagtac acatgttcca     300
ttcacgttcg gctcggggac aaagttggaa ataaaa                                336

<210> SEQ ID NO 16
<211> LENGTH: 360
<212> TYPE: DNA
<213> ORGANISM: Mus musculus
```

<400> SEQUENCE: 16

| | | | | | |
|---|---|---|---|---|---|
| gaggtgaagc | tggtggagtc | tggaggaggc | ttggtacagc | ctgggagttc | tcagagactc | 60 |
| tcctgtgcaa | cttctgggtt | caccttcact | gactactaca | tgagctgggt | ccgccagcct | 120 |
| ccaggaaagg | cacttgagtg | gttgggtttt | attagaaaca | aaactaaacg | ttacacaaca | 180 |
| gaatacagtg | catctgtgaa | gggtcggttc | accatctcca | gagataattc | ccaaagcatc | 240 |
| ctctatcttc | aaatgaacac | cctgagagct | gaggacagtg | ccacttatta | ctgtgcaaga | 300 |
| gatgatccgt | acgcacggtt | tgcttactgg | ggccaaggga | ctctggtcac | tgtctctgca | 360 |

<210> SEQ ID NO 17
<211> LENGTH: 48
<212> TYPE: DNA
<213> ORGANISM: Mus musculus

<400> SEQUENCE: 17
agatctggtc agagccttgt acacagaaat ggaaacacct atttacat                48

<210> SEQ ID NO 18
<211> LENGTH: 21
<212> TYPE: DNA
<213> ORGANISM: Mus musculus

<400> SEQUENCE: 18
aaagtttcca accgattttc t                                             21

<210> SEQ ID NO 19
<211> LENGTH: 27
<212> TYPE: DNA
<213> ORGANISM: Mus musculus

<400> SEQUENCE: 19
tctcaaagta cacatgttcc attcacg                                       27

<210> SEQ ID NO 20
<211> LENGTH: 21
<212> TYPE: DNA
<213> ORGANISM: Mus musculus

<400> SEQUENCE: 20
gggttcacct tcactgacta c                                             21

<210> SEQ ID NO 21
<211> LENGTH: 24
<212> TYPE: DNA
<213> ORGANISM: Mus musculus

<400> SEQUENCE: 21
agaaacaaaa ctaaacgtta caca                                          24

<210> SEQ ID NO 22
<211> LENGTH: 27
<212> TYPE: DNA
<213> ORGANISM: Mus musculus

<400> SEQUENCE: 22
gatgatccgt acgcacggtt tgcttac                                       27

<210> SEQ ID NO 23
<211> LENGTH: 15
<212> TYPE: DNA

<213> ORGANISM: Mus musculus

<400> SEQUENCE: 23
gactactaca tgagc                                                      15

<210> SEQ ID NO 24
<211> LENGTH: 57
<212> TYPE: DNA
<213> ORGANISM: Mus musculus

<400> SEQUENCE: 24
tttattagaa acaaaactaa acgttacaca acagaataca gtgcatctgt gaagggt       57

<210> SEQ ID NO 25
<211> LENGTH: 35
<212> TYPE: DNA
<213> ORGANISM: Mus musculus
<220> FEATURE:
<221> NAME/KEY: modified_base
<222> LOCATION: (30)..(30)
<223> OTHER INFORMATION: I
<220> FEATURE:
<221> NAME/KEY: misc_feature
<222> LOCATION: (30)..(30)
<223> OTHER INFORMATION: n is a, c, g, or t

<400> SEQUENCE: 25
cccaagcttc cagggrccar kggataracn grtgg                                35

<210> SEQ ID NO 26
<211> LENGTH: 30
<212> TYPE: DNA
<213> ORGANISM: Mus musculus

<400> SEQUENCE: 26
cccaagctta ctggatggtg ggaagatgga                                      30

<210> SEQ ID NO 27
<211> LENGTH: 32
<212> TYPE: DNA
<213> ORGANISM: Mus musculus
<220> FEATURE:
<221> NAME/KEY: modified_base
<222> LOCATION: (24)..(24)
<223> OTHER INFORMATION: I
<220> FEATURE:
<221> NAME/KEY: misc_feature
<222> LOCATION: (24)..(24)
<223> OTHER INFORMATION: n is a, c, g, or t

<400> SEQUENCE: 27
cccaagctta gctcytcwgw gganggyggr aa                                   32

<210> SEQ ID NO 28
<211> LENGTH: 16
<212> TYPE: PRT
<213> ORGANISM: Mus musculus

<400> SEQUENCE: 28

Lys Ser Ser Gln Ser Leu Leu Asp Ser Asp Gly Lys Thr Tyr Leu Asn
1               5                   10                  15

<210> SEQ ID NO 29
<211> LENGTH: 7
<212> TYPE: PRT
<213> ORGANISM: Mus musculus

<400> SEQUENCE: 29

Leu Val Ser Lys Leu Asp Ser
1               5

<210> SEQ ID NO 30
<211> LENGTH: 9
<212> TYPE: PRT
<213> ORGANISM: Mus musculus

<400> SEQUENCE: 30

Trp Gln Gly Thr His Phe Pro Trp Thr
1               5

<210> SEQ ID NO 31
<211> LENGTH: 7
<212> TYPE: PRT
<213> ORGANISM: Mus musculus

<400> SEQUENCE: 31

Gly Tyr Ser Phe Thr Gly Tyr
1               5

<210> SEQ ID NO 32
<211> LENGTH: 6
<212> TYPE: PRT
<213> ORGANISM: Mus musculus

<400> SEQUENCE: 32

Asn Pro Tyr Asn Gly His
1               5

<210> SEQ ID NO 33
<211> LENGTH: 5
<212> TYPE: PRT
<213> ORGANISM: Mus musculus

<400> SEQUENCE: 33

Gly Tyr Phe Leu Ser
1               5

<210> SEQ ID NO 34
<211> LENGTH: 17
<212> TYPE: PRT
<213> ORGANISM: Mus musculus

<400> SEQUENCE: 34

Arg Ile Asn Pro Tyr Asn Gly His Thr Phe Tyr Asn Gln Lys Phe Lys
1               5                   10                  15

Asp

<210> SEQ ID NO 35
<211> LENGTH: 48
<212> TYPE: DNA
<213> ORGANISM: Mus musculus

<400> SEQUENCE: 35
aagtcaagtc agagcctctt agatagtgat ggaaagacat atttgaat          48

<210> SEQ ID NO 36
<211> LENGTH: 21
<212> TYPE: DNA
<213> ORGANISM: Mus musculus

<400> SEQUENCE: 36
ctggtgtcta aactggactc t                                              21

<210> SEQ ID NO 37
<211> LENGTH: 27
<212> TYPE: DNA
<213> ORGANISM: Mus musculus

<400> SEQUENCE: 37
tggcaaggta cacattttcc gtggacg                                        27

<210> SEQ ID NO 38
<211> LENGTH: 21
<212> TYPE: DNA
<213> ORGANISM: Mus musculus

<400> SEQUENCE: 38
ggttactcat ttactggcta c                                              21

<210> SEQ ID NO 39
<211> LENGTH: 18
<212> TYPE: DNA
<213> ORGANISM: Mus musculus

<400> SEQUENCE: 39
aatccttaca atggtcat                                                  18

<210> SEQ ID NO 40
<211> LENGTH: 15
<212> TYPE: DNA
<213> ORGANISM: Mus musculus

<400> SEQUENCE: 40
ggctactttt tgagc                                                     15

<210> SEQ ID NO 41
<211> LENGTH: 54
<212> TYPE: DNA
<213> ORGANISM: Mus musculus

<400> SEQUENCE: 41
cgtattaatc cttacaatgg tcatactttc tacaaccaga agttcaagga caag          54

<210> SEQ ID NO 42
<211> LENGTH: 112
<212> TYPE: PRT
<213> ORGANISM: Mus musculus

<400> SEQUENCE: 42

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Phe Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Ser Val Glu Ala Glu Asp Leu Gly Ile Tyr Tyr Cys Trp Gln Gly
                85                  90                  95

```
Thr His Phe Pro Trp Thr Phe Gly Gly Gly Thr Lys Leu Glu Ile Lys
            100                 105                 110
```

<210> SEQ ID NO 43
<211> LENGTH: 112
<212> TYPE: PRT
<213> ORGANISM: Mus musculus

<400> SEQUENCE: 43

```
Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Gly Tyr
            20                  25                  30

Phe Leu Ser Trp Val Lys Gln Ser His Gly Arg Ser Leu Glu Trp Ile
        35                  40                  45

Gly Arg Ile Asn Pro Tyr Asn Gly His Thr Phe Tyr Asn Gln Lys Phe
    50                  55                  60

Lys Asp Lys Ala Thr Leu Thr Val Asp Lys Ser Ser Thr Thr Ala His
65                  70                  75                  80

Met Glu Leu Leu Ser Leu Thr Ser Glu Asp Ser Ala Val Tyr Tyr Cys
                85                  90                  95

Ala Gly Ser Asp Ser Trp Gly Gln Gly Thr Thr Leu Thr Val Ser Ser
            100                 105                 110
```

<210> SEQ ID NO 44
<211> LENGTH: 336
<212> TYPE: DNA
<213> ORGANISM: Mus musculus

<400> SEQUENCE: 44

```
gatgttgtga tgacccagac tccactcact ttgtcggtta ccattggaca accagcctcc      60
atctcttgca agtcaagtca gagcctctta gatagtgatg aaagacata tttgaattgg      120 ttgttacaga gccaggccag tctccaaagc gcctaatctt tctggtgtct aaactggact     180
ctggagtccc tgacaggttc actggcagtg gatcagggac agatttcaca ctgaaaatca     240
gcagcgtgga ggctgaggat ttgggaattt attattgctg gcaaggtaca cattttccgt     300
ggacgttcgg tggaggcacc aagctggaaa tcaaac                                336
```

<210> SEQ ID NO 45
<211> LENGTH: 336
<212> TYPE: DNA
<213> ORGANISM: Mus musculus

<400> SEQUENCE: 45

```
gaggttcagc tgcagcagtc tggacctgaa ctggtgaagc ctggggcttc agtgaagatt      60
tcctgcaagg cttctggtta ctcatttact ggctactttt tgagctgggt gaagcagagc     120
catggaagga gccttgagtg gattggacgt attaatcctt acaatggtca tactttctac     180
aaccagaagt tcaaggacaa ggccacattg actgttgaca atcctctac cacagcccac      240 atggagctcc tgagcctgac atctgaggac tctgcagtct attattgtgc aggatctgac     300
tcctggggcc aaggcaccac tctcacagtc tcctca                                336
```